US011369295B2

(12) United States Patent
Lakowicz et al.

(10) Patent No.: US 11,369,295 B2
(45) Date of Patent: Jun. 28, 2022

(54) SILICONE HYDROGEL BASED FLUORESCENT ASSAY AND CONTACT LENS

(71) Applicant: University of Maryland, Baltimore, Baltimore, MD (US)

(72) Inventors: Joseph R. Lakowicz, Ellicott City, MD (US); Ramachandram Badugu, Ellicott City, MD (US); E. Albert Reece, Lutherville, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 698 days.

(21) Appl. No.: 16/319,179

(22) PCT Filed: Jul. 20, 2017

(86) PCT No.: PCT/US2017/043087
§ 371 (c)(1),
(2) Date: Jan. 18, 2019

(87) PCT Pub. No.: WO2018/017842
PCT Pub. Date: Jan. 25, 2018

(65) Prior Publication Data
US 2020/0229740 A1 Jul. 23, 2020

Related U.S. Application Data

(60) Provisional application No. 62/451,824, filed on Jan. 30, 2017, provisional application No. 62/364,444, filed on Jul. 20, 2016.

(51) Int. Cl.
*A61B 5/1495* (2006.01)
*A61B 5/145* (2006.01)
(Continued)

(52) U.S. Cl.
CPC ........ *A61B 5/1495* (2013.01); *A61B 5/14507* (2013.01); *A61B 5/14532* (2013.01);
(Continued)

(58) Field of Classification Search
CPC .............. A61B 5/1455; A61B 5/14556; A61B 5/14546; A61B 5/14507; A61B 5/14532; A61B 5/1495; A61B 5/6821; C07F 5/025
See application file for complete search history.

(56) References Cited

U.S. PATENT DOCUMENTS 6,319,540 B1    11/2001  Van Antwerp
6,681,127 B2 *   1/2004  March .................. A61B 5/1455
                                                         600/319
(Continued)

OTHER PUBLICATIONS

Lakowicz, J. R., Principles of Fluorescence Spectroscopy, 3rd Ed., 2006, pp. 142-167, Springer, New York.
(Continued)

*Primary Examiner* — Eric F Winakur
(74) *Attorney, Agent, or Firm* — Wolter Van Dyke Davis, PLLC; Eugene Molinelli; Martha Cassidy

(57) ABSTRACT

A material, article, system and method include a probe composition that includes a hydrophobic portion, a hydrophilic portion, an analyte-binding portion and a fluorophore portion. The analyte-binding portion is configured to bind to an analyte in an aqueous solution. The fluorophore portion is configured to change an optical property of fluorescent light emitted in response to incident excitation light when the probe composition changes between a first state in which the analyte is not bound to the analyte-binding portion and a second state in which the analyte binds to the analyte-binding portion. A material includes the probe composition and a silicone hydrogel substrate having a hydrogel network that allows flow of aqueous solution through the solution and a silicone network that occupies interstices of the
(Continued)

hydrogel network. A contact lens having the material enables remote detection of glucose concentration in tear fluid of a subject.

24 Claims, 36 Drawing Sheets

(51) Int. Cl.
　　　A61B 5/1455　　　(2006.01)
　　　C07F 5/02　　　　(2006.01)
　　　A61B 5/00　　　　(2006.01)
(52) U.S. Cl.
　　　CPC ...... *A61B 5/14546* (2013.01); *A61B 5/14556* (2013.01); *A61B 5/6821* (2013.01); *C07F 5/025* (2013.01)

(56) References Cited

U.S. PATENT DOCUMENTS

| | | | | |
|---|---|---|---|---|
| 6,766,183 | B2* | 7/2004 | Walsh | A61B 5/14532 600/317 |
| 8,385,998 | B2* | 2/2013 | Zhang | A61B 5/14532 600/319 |
| 8,569,502 | B2 | 10/2013 | Geddes et al. | |
| 9,222,941 | B2 | 12/2015 | Barwell et al. | |
| 2002/0119581 | A1 | 8/2002 | Daniloff et al. | |
| 2007/0030443 | A1 | 2/2007 | Chapoy et al. | |
| 2010/0305231 | A1 | 12/2010 | Kennedy | |
| 2011/0136929 | A1 | 6/2011 | Chow et al. | |
| 2012/0259188 | A1 | 10/2012 | Besling | |
| 2015/0080685 | A1 | 3/2015 | Markle et al. | |

OTHER PUBLICATIONS

Lakowicz, J. R., Principles of Fluorescence Spectroscopy, 3rd ed., 2006, pp. 129-131, Springer, New York.
Lakowicz, J. R., Principles of Fluorescence Spectroscopy, 3rd ed., 2006, pp. 627-630, Springer, New York.
Lakowicz, J. R. Principles of Fluorescence Spectroscopy, 3rd ed., 2006, pp. 211, Springer, New York.
Extended European Search Report, in application No. 17831876.2, dated Dec. 11, 2019, pp. 1-12.
Search Report for corresponding Chinese Patent Application No. 2017800576357, dated Jun. 2, 2021.
ISA/US, "International Search Report and Written Opinion for the corresponding PCT application PCT/US2017/43087", dated Nov. 22, 2017, pp. 1-10.
James et al., Novel saccharide-photoinduced electron transfer sensors based on the interaction of boronic acid and amine, J. Am. Chem. Soc., 1995, pp. 8982-8987 vol. 117.
Montalti et al., Energy transfer from a fluorescent hydrogel to a hosted fluorophore, Langmuir, 2006, pp. 2299-2303, vol. 22.
Kanekiyo and Takayoshi, A Multicolor saccharide sensing chip created via layer-by-layer adsorption of boronic-acid-containing polymer, Procedia Engineering, 2012, pp. 1153-1156, vol. 47.
Zenkl and Klimant, Fluorescent acrylamide nanoparticles for boronic acid based sugar sensing—from probes to sensors, Microchim. Acta., 2009, pp. 123-131, vol. 166.
Yang et al., Towards the real-time monitoring of glucose in tear fluid: Holographic glucose sensors with reduced interference from lactate from pH, Biosen. Bioelectron., 2008, pp. 899-905, vol. 23.
Alexeev et al., Photonic crystal glucose-sensing material for non-invasive monitoring of glucose in tear fluid, Clin. Chem., 2004, pp. 2353-1360, vol. 50.
Arimori et al., Modular fluorescence sensors for saccharides, Chem. Commun., 2001, pp. 1836-1837.
Bagudu et al., Development of Smart Contact Lenses for Ophthalmic Glucose Monitoring.

Bagudu et al., Fluorescence sensors for monosaccharides based on the 6-methylquinolinium nucleus and boronic acid moiety: potential application to ophthalmic diagnostics, Talanta, 2005, pp. 762-768, vol. 65.
Dewey et al., Calculation of Fluorescence Resonance Energy Transfer On Surfaces, Biophys. J. © Biophysical Society, 1980, pp. 1023-1036, vol. 32.
Dicesare et al., Evaluation of Two Synthetic Glucose Probes for Fluorescence-Lifetime-Based Sensing, Analytical Biochemistry, 2001, pp. 154-160, vol. 294.
Lakowicz et al.,. Transient Effects in Fluorescence Quenching Measured by 2-GHz Frequency-Domain Fluorometry, J Phys Chem., 1987, pp. 3277-3285.
Eftink et al., Intramolecular fluorescence quenching in covalent acrylamide-indole adducts, Photochemistry and Photobiology, 1989, pp. 725-729, vol. 49.
Lakowicz et al., Optical sensing of pH and pC0, using phase-modulation fluorimetry and resonance energy transfer, Analytica Chemica Acta, 1993, pp. 179-186, vol. 272.
Lakowicz and Szmacinski, Fluorescence lifetime-based sensing of pH, Ca2+, KS and glucose, Sensors and Actuators B, 1993, pp. 133-143, vol. 11.
Lakowicz et al., Plasmon-controlled fluorescence: a new paradigm in fluorescence spectroscopy, Analyst., 2008, pp. 1308-1346, vol. 133.
Haidekker et al., Fluid shear stress increases membrane fluidity in endothelial cells: a study with DCVJ fluorescence, Am J Physiol Heart Circ Physiol, 2000, pp. H1401-H1406, vol. 278.
Hill R.M, Silicone surfactants—new developments, Current Opinion in Colloid And Interface Science, 2002, pp. 255-261, vol. 7.
Horgan et al., Crosslinking of phenylboronic acid receptors as a means of glucose selective holographic detection, Biosensors and Bioelectronics, 2006, pp. 1838-1845, vol. 21.
Huang et al., The Cost-Effectiveness of Continuous Glucose Monitoring in Type 1 Diabetes, Diabetes Care, 2010, pp. 1269-1274, vol. 33.
Iwaki et al., Antibodies for Fluorescent Molecular Rotors, Biochemistry, 1993, pp. 7589-7592, vol. 32.
Joshi et al., Radiation Boundary Conditions in Collisional Quenching of Fluorescence; Determination By Frequency-Domain Fluorometry, Chemical Physics Letters, 1987, pp. 200-207, vol. 135(3).
Kim et al., AFM and SFG studies of pHEMA-based hydrogel contact lens surfaces in saline solution: adhesion, friction, and the presence of non-crosslinked polymer chains at the surface, Biomaterials, 2002, pp. 1657-1666, vol. 23.
Lingley et al., A single-pixel wireless contact lens display, J. Micromech. Microeng., 2011, pp. 125014, vol. 21.
Luensmann and Jones, Albumin adsorption to contact lens materials: A review, Contact Lens & Anterior Eye, 2008, pp. 179-187, vol. 31.
Mccanna et al., Rabbit Models of Contact Lens-Associated Corneal Hypoxia: A Review of the Literature, Eye & Contact Lens, 2008, pp. 160-165, vol. 34.
Miller et al., Evidence of a Strong Association BetweenFrequencyofSelf-Monitoring of Blood Glucose and Hemoglobin A1c Levels in T1D Exchange Clinic Registry Participants, Diabetes Care, 2013, pp. 2009-2014, vol. 36.
Mulla et al., 3-Methoxycarbonyl-5-nitrophenyl boronic acid: high affinity diol recognition at neutral pH, Bioorganic & Medicinal Chemistry Letters, 2004, pp. 25-27, vol. 14.
Nad and Pal, Electron Transfer from Aromatic Amines to Excited Coumarin Dyes: Fluorescence Quenching and Picosecond Transient Absorption Studies, J. Phys. Chem. A, 2000, pp. 673-680, vol. 104.
Panchuck-Voloshina et al., Alexa Dyes, a Series of New Fluorescent Dyes that Yield Exceptionally Bright, Photostable Conjugates, The Journal of Histochemistry & Cytochemistry, 1999, pp. 1179-1188, vol. 47.
Phillips and James, Boronic Acid Based Modular Fluorescent Sensors for Glucose, Journal of Fluorescenc, 2004, pp. 549-559, vol. 14.
Rantamaki et al., Human Tear Fluid Lipidome: From Composition to Function, PLOS One, 2011, pp. e19553, vol. 6.

(56) References Cited

OTHER PUBLICATIONS

Shamsi et al., Analysis and Comparison of Proteomic Profiles of Tear Fluid from Human, Cow, Sheep, and Camel Eyes, IOVS, 2011, pp. 9156-9165, vol. 52.
Springsteen and Wang, A detailed examination of boronic acid-diol complexation, Tetrahedron, 2002, pp. 5291-5300, vol. 58.
Szmacinski and Lakowicz, Optical Measurements of pH Using Fluorescence Lifetimes and Phase-Modulation Fluorometry, Anal Chem., 1993, pp. 1668-1674, vol. 65.
Szmacinski and Lakowicz, Possibility of simultaneously measuring low and high calcium concentrations using Fura-2 and lifetime-based sensing, Cell Calcium, 1995, pp. 64 75, vol. 18.
Thyrhaug et al., Excited state kinetics of anthracene-bridge-aniline intramolecular exciplexes, Photochemical & Photobiological Sciences, 2014, pp. 1093-1105, vol. 13.
Wagner, The Use of Coumarins as Environmentally-Sensitive Fluorescent Probes of Heterogeneous Inclusion Systems, Molecules, 2009, pp. 210-237, vol. 14.
Whitaker et al., Spectral and Photophysical Studies of Benzo[c]xanthene Dyes: Dual Emission pH Sensors, Analytical Biochemistry, 1991, pp. 330-344, vol. 194.
Wolber and Hudson, An Analytic Solution To the Forster Energy Transfer Problem in Two Dimensions, Biophys. J. © Biophysical Society, 1979, pp. 197-210, vol. 28.
Choudhury et al., Directing Fluorescence with Plasmonic and Photonic Structures, Acc. Chem. Res., 2015, pp. 2171-2180, vol. 48.
Gebhardt et al., Glucose sensing in transdermal body fluid collected under continuous vacuum pressure via microspores in the stratum corneum, Diabetes Technol. Ther., 2001, pp. 81-90, vol. 3.
Kiistala, Suction blister device for separation of viable epidermis from dermis, J. Invest. Dermatol., 1968, pp. 129-137, vol. 50.
Tierney et al., Clinical evaluation of the GlucoWatch biographer: a continual, non-invasive glucose monitor for patients with diabetes, Biosens. Bioelectron., 2001, pp. 621-629, vol. 16.
Rhee et al., Clinical experience of an iontrophoresis-based glucose monitoring system, J. Korean Med. Sci., 2007, pp. 70-73, vol. 22.
The Diabetes Research in Children Network (Direcnet) Study Group, Accuracy of the GlucoWatch G2 biographer and the continuous glucose monitoring system during hypoglycemia. Experience of the Diabetes Research in Children Network (DirecNet), Diabetes Care, 2004, pp. 722-726, vol. 27.
Pickup et al., Fluorescence based glucose sensors, Biosen. Bioelectron., 2005, pp. 2555-2565, vol. 20.
Schultz et al., Affinity sensor: A new technique for developing implantable sensors for glucose and mother metabolites, Diabetes Care, 1982, pp. 245-253, vol. 5.
Cummins et al., Optimization of a Concanavalin A-based glucose sensor using fluorescence anisotropy, Anal. Chem., 2013, pp. 5397-5904, vol. 85.
Boss et al., A viscosity-dependent affinity sensor for continuous monitoring of glucose in biological fluids, Biosensors and Bioelectron., 2011, pp. 223-228, vol. 30.
Fabrice et al., The accuracy of dynamic contour tonometry over soft contact lenses, Opt. Vis. Sci., 2013, pp. 125-130, vol. 90.
Peng et al., A new biosensor for glucose determition in serum based on up-converting fluorescence resonance anergy transfer, Biosensors and Bioelectron, 2011, pp. 414-420, vol. 28.
Aloraefy et al., In vitro evaluation of fluorescence glucose biosensor response, Sensors, 2014, pp. 12127-12148, vol. 14.
Lee et al., A graphene-based electrochemical device with thermoresponsive microneedles for diabetes monitoring and therapy, Nature Nano., 2016, pp. 556-574, vol. 11.
Lee et al., A patch type non-enzymatic biosensor based on 3D SUS micro-needle electrode array for minimally invasive continuous glucose monitoring, Sensors Actuators B. Chem., 2016, pp. 1144-1151, vol. 222.
Baca et al., Tear glucose analysis for the noninvasive detection and monitoring of diabetes mellitus, Ocular Surface, 2007, pp. 280-293, vol. 5.
Lane et al., Tear glucose dynamics in diabetes mellitus, Curr. Eye Res., 2006, pp. 895-901, vol. 31.
Sen and Sarin, Tear glucose levels in normal people and in diabetic patients, British J. Oph.,1980, pp. 693-695, vol. 64.
Yao et al., A contact lens with embedded sensor for monitoring tear glucose level, Biosen. Bioelectron., 2011, pp. 3290-3296, vol. 26.
Letko et al., UVA-light and riboflavin-mediated corneal collagen cross-linking, Int. Opth. Clinics., 2011, pp. 63-76, vol. 51.
Changyuan et al., Photophysical and photochemical processes of riboflavin (vitamin B2) by means of the transient absorption spectra in aqueous solution, Science in China, 2001, pp. 39-44, vol. 44.
Cullen, Photobiology of the Cornea, 2015, pp. 1-15, http://photobiology.info/Cullen.html.
Doutch et al., Ultraviolet light transmission through the human corneal stroma is reduced in the periphery, Biophys. J., 2012, pp. 258-1264, vol. 102.
Dicesare et al., Fluorescent probe for monosaccharides based on a functionalized boron-dipyrromethene with a boronic acid group, Tetrahedron Letts., 2001, pp. 9105-9108, vol. 42.
Wu and Brand, Resonance Energy Transfer: Methods and Applicaitons, Analytical Biochemistry, 1994, pp. 1-13, vol. 218.
Arimori et al., A modular fluorescence intramolecular energy transfer saccharide sensor, Organ. Letts., 2002, pp. 4249-4251, vol. 4.
Pickup et al., In vivo glucose sensing for diabetes management: progress towards non-invasive monitoring, BMJ, 1999, pp. 1-4, vol. 319.
Doutch et al., Ultraviolet light transmission through the human corneal stroma is reduced in the periphery, Biophys. J., 2012, pp. 1258-1264, vol. 102.
Osama et al., Corneal and retinal effects of ultraviolet B exposure in a soft contact lens mouse model, Invest. Opthal. Vis Sci., 2012, pp. 2403-2413, vol. 53.
Harris et al., Ultraviolet transmittance of the vistakon disposable contact lenses, Contact Lens Ant. Eye., 2000, pp. 10-15, vol. 23.
Rahmani et al.., Spectral transmittance of UV-blocking soft contact lenses: a comparative study, Cont. Lens Ant. Eye., 2014, pp. 451-454, vol. 37.
Arimori et al., Fluorescent internal charge transfer (ICT) saccharide sensor, Tetrahed. Letts., 2001, pp. 1553-4555, vol. 42.
Saruabh et al., Evaluation of sCMOS cameras for detection and localization of single Cy5 molecules, Optics Exp., 2012, pp. 7338-7349, vol. 20.
Seidel et al., Nucleobase-Specific Quenching of Fluorescent Dyes. 1. Nucleobase One-Electron Redox Potentials and Their Correlation with Static and Dynamic Quenching Efficiencies, J. Phys. Chem, 1996, pp. 5541-5553, vol. 100.
Lakowicz et al., Analysis of excited-state processes by phase-modulation fluourescence specrroscopy, Biophys Chem., 1982, pp. 117-132, vol. 16.
Della Rocca et al., Real-time fluorescence lifetime actuation for cell sorting using a CMOS SPAD silicon photomultiplier, Optics Letts., 2016, pp. 1-4.
Rae et al., A CMOS time-resolved fluorescence lifetime analysis micro-system, Sensors, 2009, pp. 9255-9274, vol. 9.
Li et al., Video-rate fluorescence lifetime imaging camera with CMOS single-photon avalanche diode arrays and high-speed imaging algorithm, J. Biomed Optics., 2011, pp. 096012-1/12, vol. 16.
Lakowicz et al., Fluorescence lifetime imaging of free and protein-bound NADH, Proc. Natl. Acad. Sci., 1992, pp. 1271-1275, vol. 89.
Lakowicz et al., Fluorescence lifetime imaging, Anal. Biochem., 1992, pp. 316-330, vol. 202.
Lakowicz, et al., Fluorescence lifetime imaging of calcium using Quin-2, Cell Calcium, 1992, pp. 131-147, vol. 13.
Lakowicz and Maliwal, Construction and performance of a variable-frequency phase-modulation fluorometer, Biophys. Chem., 1985, pp. 61-78, vol. 21.
Alcala et al., A multifrequency phase fluorometer using the harmonic content of a mode-locked laser, Inst. Sci. Tech., 1985, pp. 225-250, vol. 14.
Laczko et al., A 10 Ghz frequency-domain fluorometer, Rev. Sci. Instrum., 1990, pp. 2331-2337, vol. 61.

(56) References Cited

OTHER PUBLICATIONS

Gratton and Limkeman, A continuously variable frequency cross-correlation phase fluorometer with picosecond resolution, Biophys. J., 1983, pp. 315-324, vol. 44.

Fang et al., Progress in boronic acid-based fluorescent glucose sensors, J. Fluores., 2004, pp. 481-480, vol. 14.

Steiner et al., Optical methods for sensing glucose, Chem. Soc. Rev., 2011, pp. 4805-4839, vol. 40.

Gao et al., New boronic acid fluorescent reporter compounds. 2. A naphthalene-based on-off sensor functional at physiological pH, Org. Letts., 2003, pp. 4615-1618, vol. 5.

Kanekiyo and Tao, Selective glucose sensing utilizing complexation with fluorescent boronic acid on polycation, Chem. Letts., 2005, pp. 196-197, vol. 34.

Badugu et al., Ophthalmic glucose monitoring using disposable contact lenses, a review, J Fluoresc., 2004, pp. 617-633, vol. 14.

Badugu et al., A wavelength-ratiometric fluoride-sensitive probe based on the quinolinium nucleus and boronic acid moiety, Sensors and Actuators, 2005, pp. 103-110.

\* cited by examiner

500 SINGLE ION LENS

503 Cl⁻
505 Ca²⁺
507 Mg²⁺
509 pH
511 Na⁺
513 K⁺
515 GLUCOSE
501 MULTIPLE ION LENS

FIG. 7A
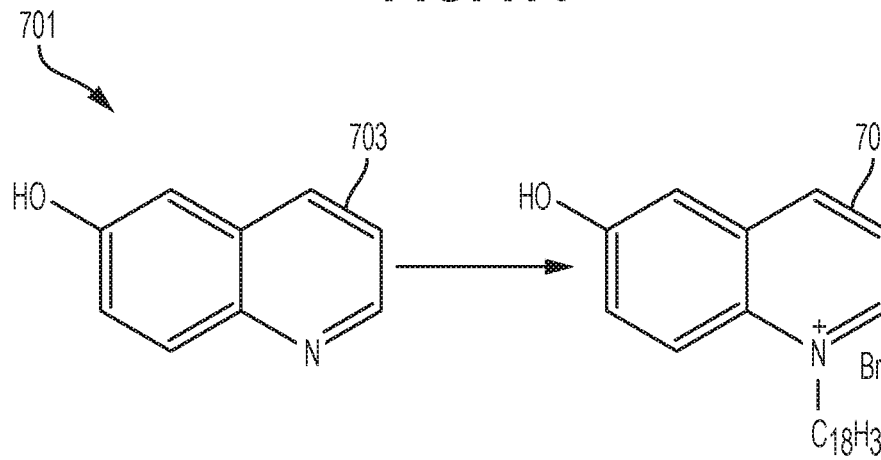
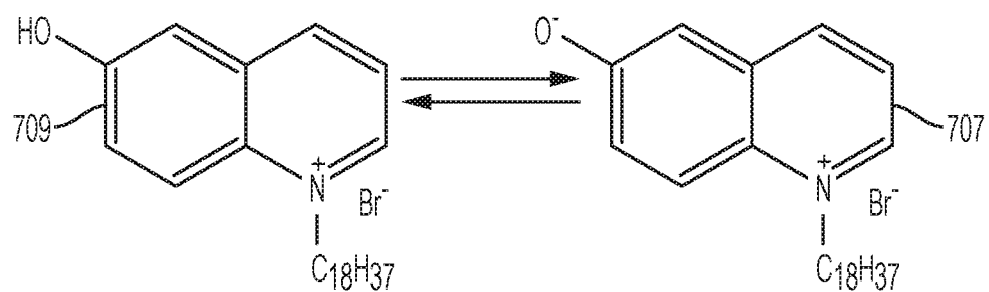
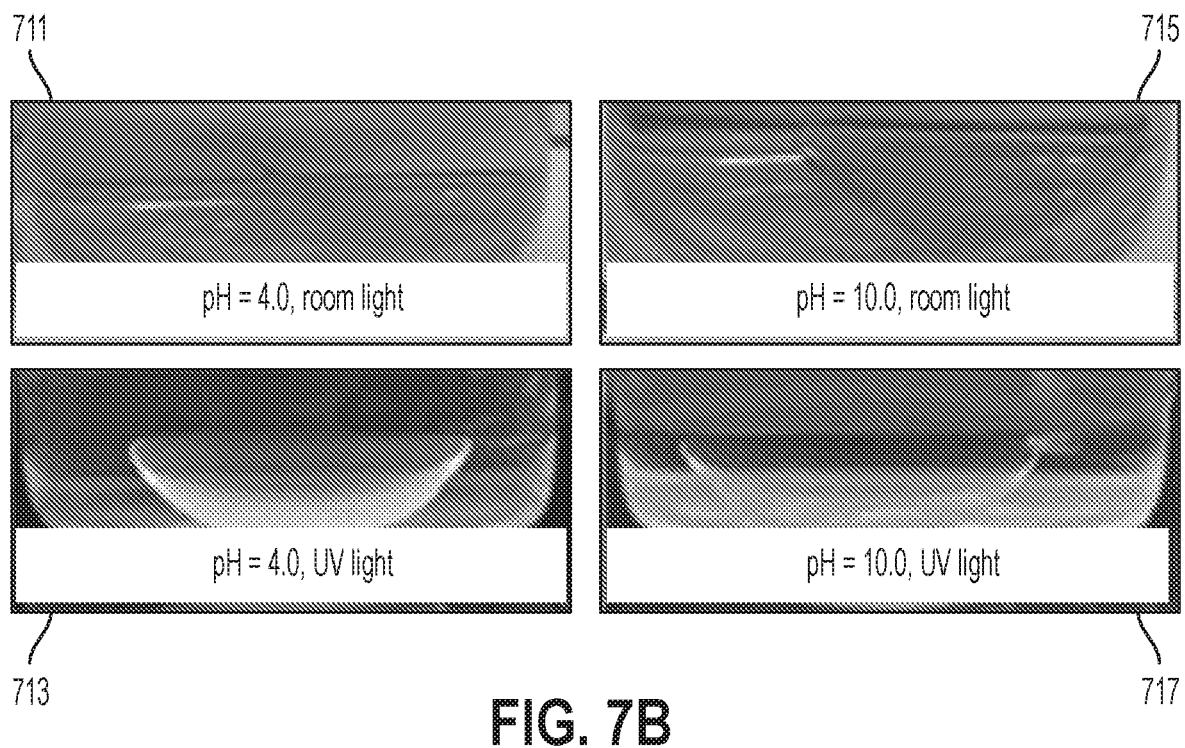
FIG. 7B

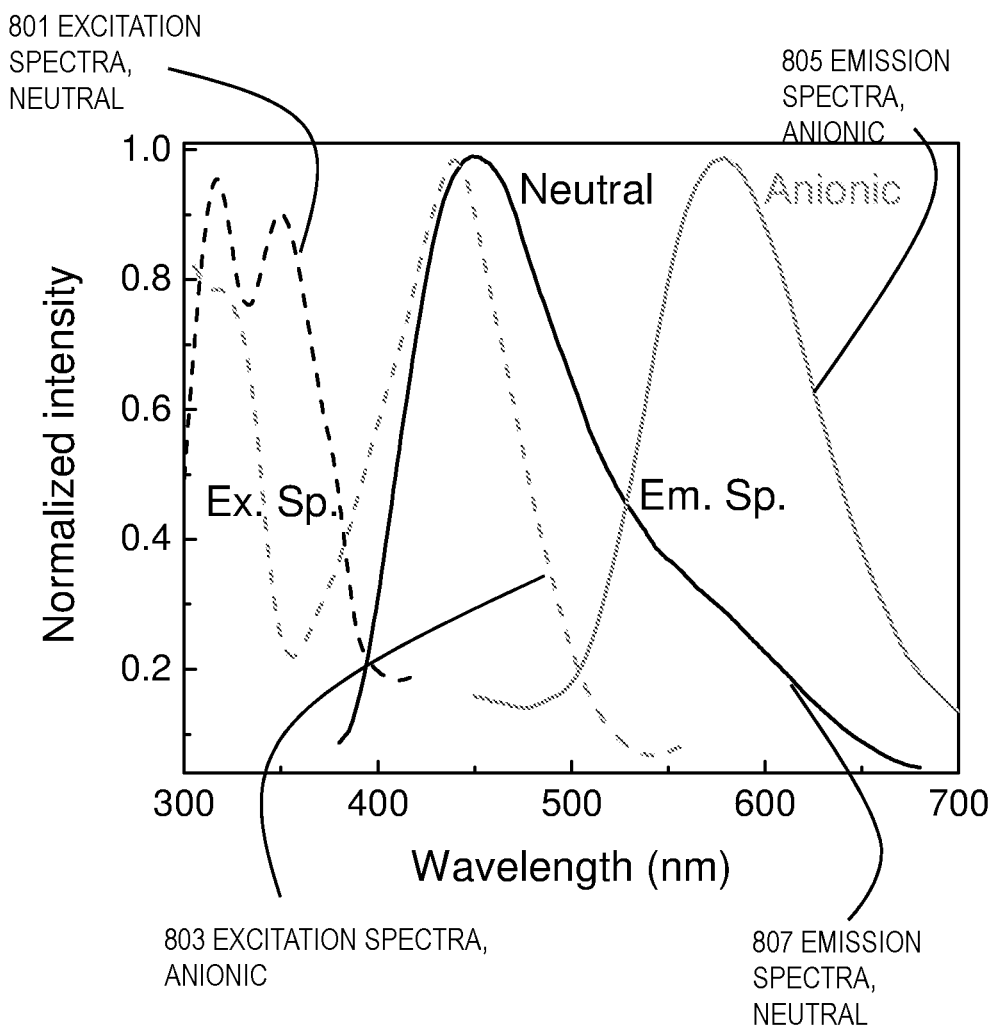

FIG. 28
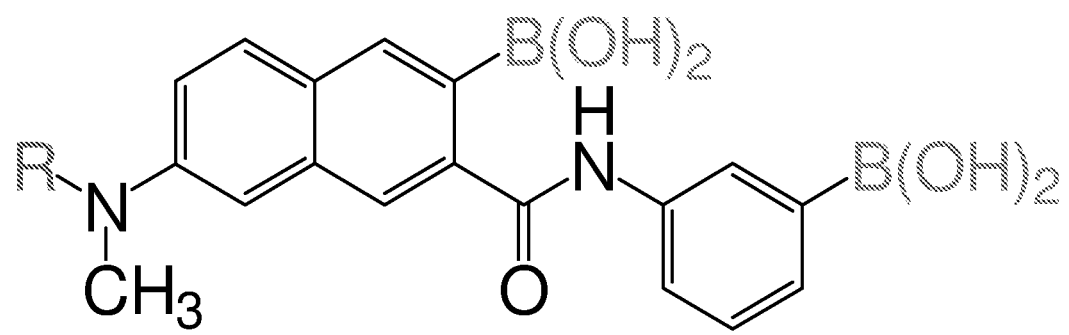
2801
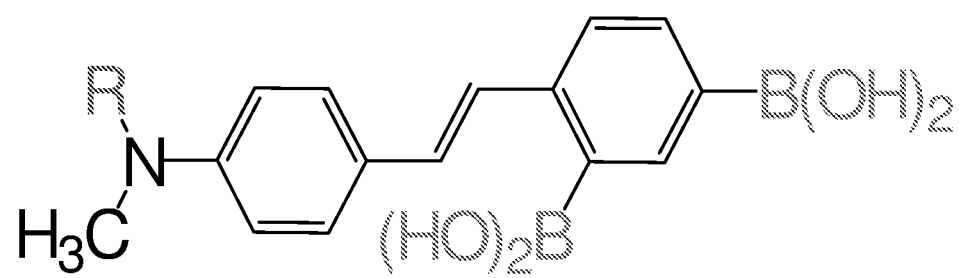
2803

FIG. 29
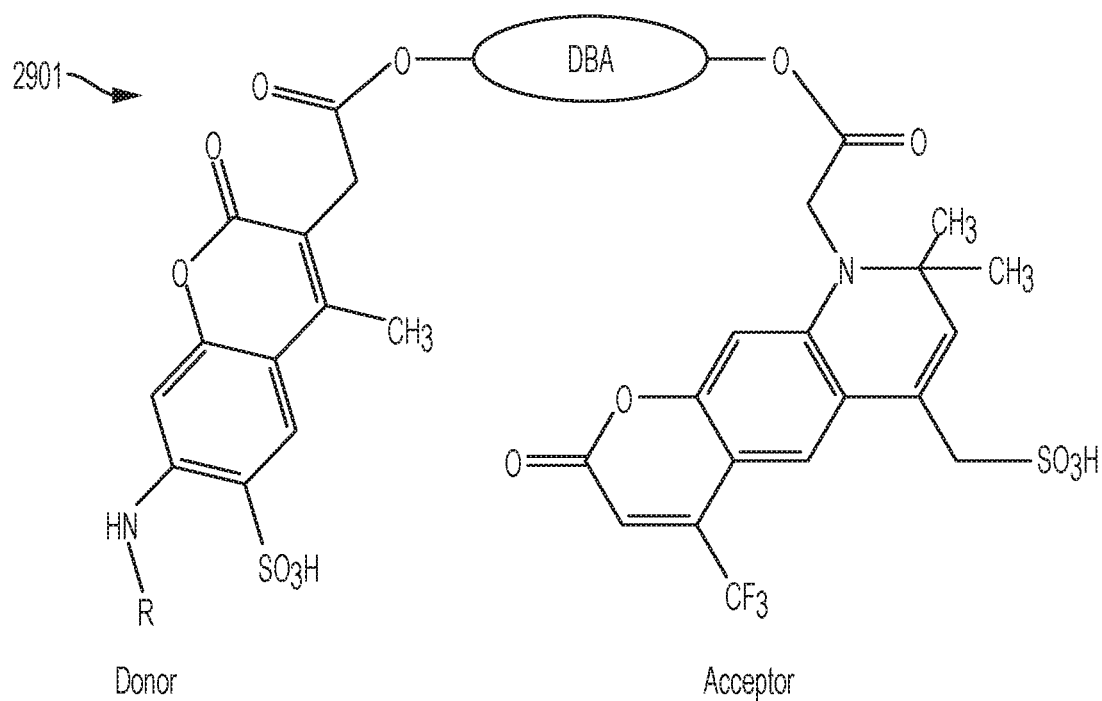
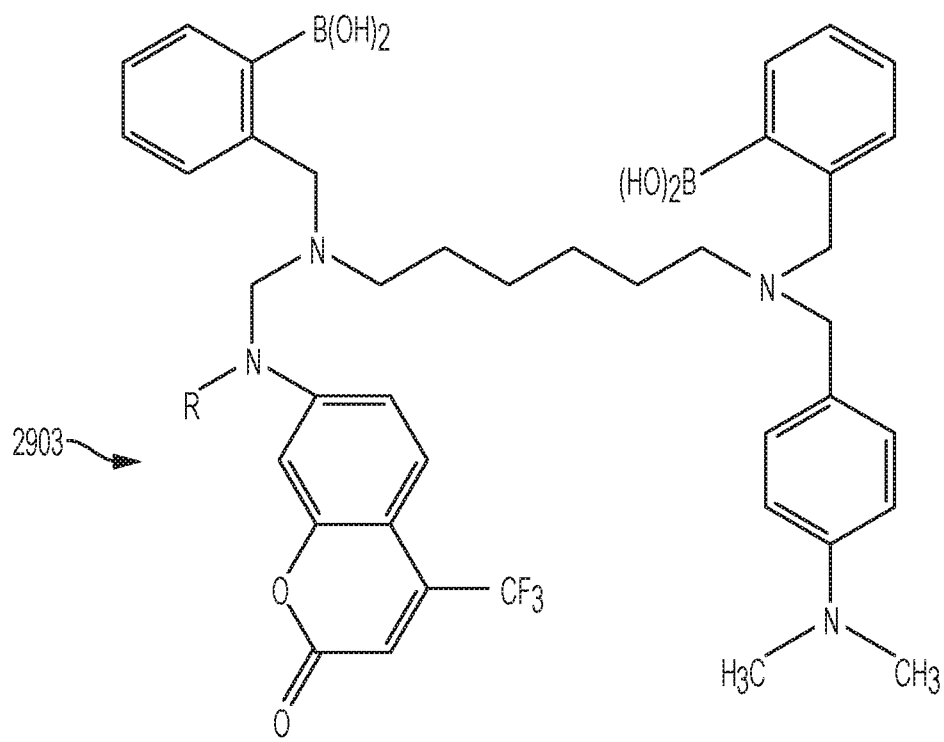

SILICONE HYDROGEL BASED FLUORESCENT ASSAY AND CONTACT LENS

CROSS-REFERENCE TO RELATED APPLICATIONS

This application is a 371 national stage application of PCT Application No. PCT/US2017/043087 filed Jul. 20, 2017 which claims benefit of Provisional Appln. 62/364,444, filed Jul. 20, 2016, and claims benefit of Provisional Appln. 62/451,824, filed Jan. 30, 2017, the entire contents of each of which are hereby incorporated by reference as if fully set forth herein, under 35 U.S.C. § 119(e).

STATEMENT OF GOVERNMENTAL INTEREST

This invention was made with government support under Grant Numbers EB006521, EB018959, GM107986 and OD019975 awarded by the National Institutes of Health. The government has certain rights in the invention.

BACKGROUND

For some conditions, such as dry eye, keratitis and diabetes, it is useful to detect the presence or concentration of analytes, such as electrolytes, biomolecules, or glucose, in tear fluid. However, at the present time there are limited practical ways to measure tear analytes because the irritation caused by sample collection disturbs the stationary analyte concentrations in tear fluid. Current in situ methods to measure these analytes, including using a contact lens with an electronic sensor come with costs involving instability, inefficiency, complexity or expense, or some combination.

SUMMARY

Techniques are provided for silicone hydrogel based fluorescent assays that can be used in a microfluidic device, wearable contact lens, a DNA or protein array, clinical assay on any solid substrate (preferably with optical transparency), or by immersion assays whereby the target molecules bind to the target-specific silicone hydrogel. As used herein, the term "concentration" refers to determining a numerical value for the amount (weight or volume) of an analyte in a volume of a fluid, including a binary determination whether the amount is above some measurable threshold, i.e., is present, in a sample.

In a first set of embodiments, a probe composition includes a hydrophobic portion, a hydrophilic portion, an analyte-binding portion and a fluorophore portion. The analyte-binding portion is configured to bind to an analyte in an aqueous solution. The fluorophore portion is configured to change an optical property of fluorescent light emitted in response to incident excitation light when the probe composition changes between a first state in which the analyte is not bound to the analyte-binding portion and a second state in which the analyte binds to the analyte-binding portion.

In a second set of embodiments, a material includes the probe composition and a silicone hydrogel substrate having a hydrogel network that allows flow of aqueous solution through the solution and a silicone network that occupies interstices of the hydrogel network.

In a third set of embodiments, a system includes the material and a remote monitor subsystem configured to detect the change of the optical property of the fluorescent light emitted in response to the incident excitation light without mechanically contacting the material.

In a fourth set of embodiments, a method includes obtaining a silicone hydrogel substrate and contacting the substrate with an aqueous solution that comprises the probe composition as recited above to form a probe-substrate material. The method also includes contacting the probe-substrate material with an aqueous sample solution. Further, the method includes illuminating, using a light source, the probe-substrate material in contact with the sample solution. Yet even further, the method includes measuring a value of a property of the fluorescent light emitted by the probe-substrate material in contact with the sample solution in response to the illuminating. Even further still, the method includes determining a value of a concentration of the analyte in the aqueous sample solution based on the value of the property of the fluorescent light.

In a fifth set of embodiments, a non-transitory computer-readable medium is configured to cause a system to perform one or more steps of the above method.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 7A is a chemical diagram that illustrates an example synthesis scheme for a probe composition for use to measure and detect pH in a contact lens, according to an embodiment;

FIG. 7B is a set of images that illustrates how an example Quin C-18 probe fluoresces at various pH levels when exposed to UV light, according to an embodiment;

FIG. 8 is a graph that illustrates an example excitation spectra (left) and emission spectra (right) of 6-OH—N—C18H37-QBr in Biofinity™ contact lens in water, according to an embodiment;

FIG. 28 is a set of chemical diagrams that illustrate diboronic acid ICT Glu-SFs for binding at interfaces in SiHG lenses, according to an embodiment;

FIG. 29 is a set of chemical diagrams that illustrate Glu-SF structures using a diboronic acid on a C6 linker with FRET mechanism, according to an embodiment and a Glu-SF structures using a diboronic acid on a C6 linker with a collisional quenching mechanism, according to an embodiment;

DETAILED DESCRIPTION

Figure 1A:
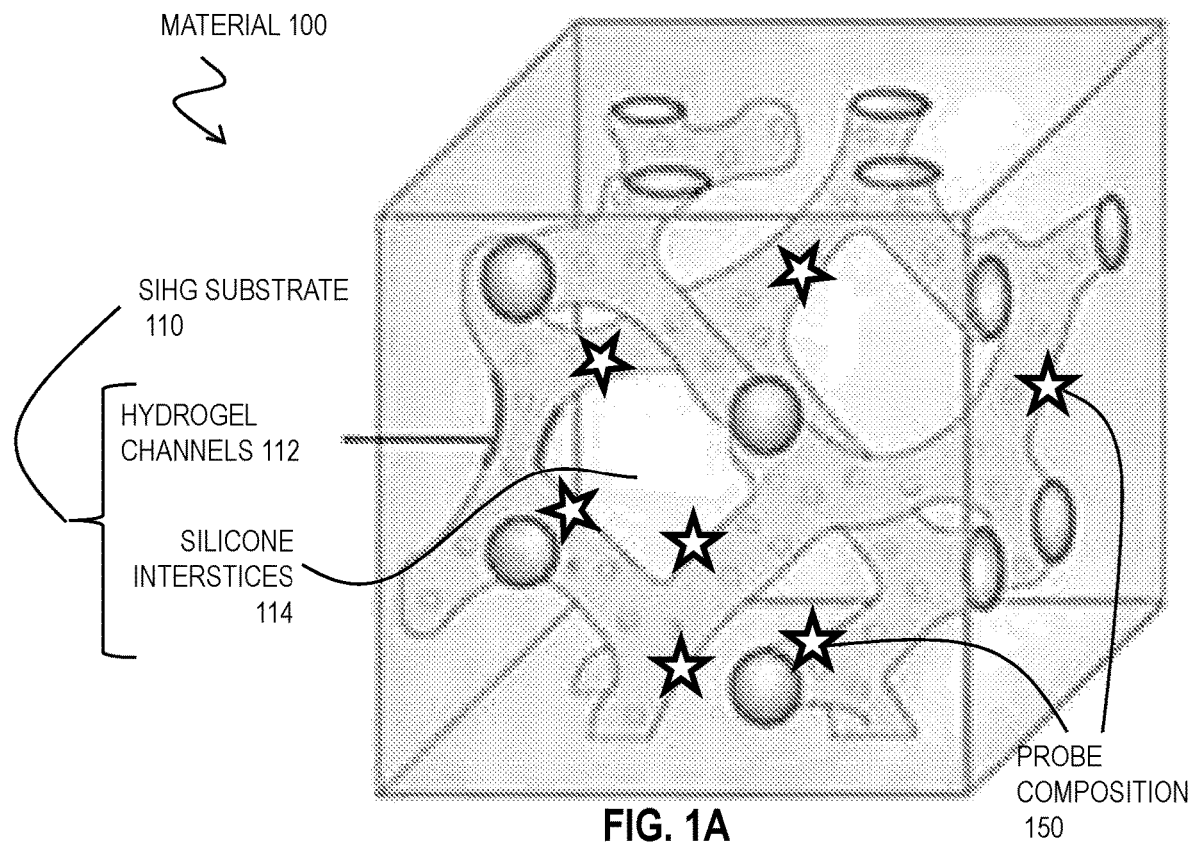
FIG. 1A and FIG. 1B are block diagrams that illustrate an example probe-substrate material, according to an embodiment.

A composition, material, method, apparatus and system are described for a silicone hydrogel based assay and contact lens. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of contact lenses made of a material that includes a silicone hydrogel substrate and fluorescent probes attracted to a water-silicone interface of the substrate, for which fluorescence is measured remotely. However, the invention is not limited to this context. In other embodiments the material is part of a microfluidic device or other medical device that comes in contact with one or more fluids of a subject, or the fluorescent measurement is performed by a subsystem embedded in the substrate or mechanically in contact with the substrate. In embodiments, the invention is used with surface-based testing such as DNA and protein arrays, or clinical assays on substrates or by immersion of silicone hydrogel into the sample followed by such measurements.

1. Overview

Here are described new techniques for fluorescent assays that take advantage of the structure of silicone hydrogels to affix assay specific fluorescent probes (also referred to as "probe compositions") to the silicone interstices between hydrogel nanochannels that allow the flow of aqueous sample solutions with analyte past the fixed probes. The probes require at least a hydrophobic portion to be attracted to the silicone interstices, a hydrophilic portion to maintain contact with the aqueous sample solution, an analyte-binding portion to capture an analyte from the sample solution, and a fluorophore portion that will change at least one measureable property of its fluorescent emissions when an analyte binds to the analyte-binding portion. In some embodiments, the fluorophore portion is made up of several separate sub-portions. In some embodiments one or more spacer portions are included in the probe to ensure that the analyte-binding portion and fluorophore portion have the proper spatial relationships to interact and demonstrate the desired functionality. Because the probe need not be a single molecule, the probe is also called a probe composition herein.

These techniques enable the determination of concentration of analytes in tear fluid of a subject's eye using a low cost commercial contact lens as a substrate and readily available imaging technology as a remote monitoring subsystem. For at least these reasons, the new techniques are superior to previous approaches. In addition, the new techniques can be used in a microfluidic device deployed inside or outside the eye of a subject to measure other fluids in addition to, or instead of, tear fluid, of the same or different subjects. As used herein a subject is an animate or inanimate object including a geological formation, a machine, or a living organism including a plant or an animal, the later including a human.

Specific analytes of interest that have been the target of previous approaches to determine the concentration in tear fluid include: glucose for a subject with diabetes; electrolyte imbalance for Dry Eye Syndrome (DRY, also known as Dry Eye Disease, DED); and defensins and other biomarkers for infection. (Defensins are small peptides with 29 to 42 amino acids that are constrained into folded forms by six conserved cysteine residues.)

One attempt to avoid tear collection and thus minimize eye irritation is electrochemical detection of tear glucose in situ using a specially fabricated contact lens called the GLUCOLENS™ being developed by the Google X project of Alphabet, Inc, (Mountain View, Calif.). The GLUCOLENS™ includes electronic components and glucose sensors to allow continuous glucose measurements, and is powered by an induction coil also embedded in the lens and placed to circle a pupil of a subject wearing the lens. The operating principle of glucose self-testing kits and the GLUCOLENS™ is based on the same principle as in the first glucose electrodes and present glucometers; i.e. glucose oxidase and electrochemical $H_2O_2$ detection. The need for complex embedded electronics increases the cost of the approach and may prevent this approach from becoming a daily use product. A daily use product is preferred for use, especially in developed countries, for reasons of safety and patient choice. The suitability of the approach for analytes and biomarkers has not been demonstrated and is likely to be hindered again by the cost of the embedded electronics.

Contact lenses were initially made from glass, then polymethylmethacrylate (PMMA) was found to have higher optical clarity than glass and less costly to manufacture. PMMA lenses were used from the 1940s to the 1970s. These hard contact lenses could not be worn for long periods of time because corneas obtain most of their oxygen from the air, and these hard contact lenses were not permeable to oxygen. Oxygen permeable soft contact lenses were developed using hydrogel polymers such as cross-linked polyhydroxy-methmethacrylate (HEMA). The oxygen permeability of hydrogels is expressed by their Dk value and pure water has a Dk value near 80. Dk values below 22 are too low and result in cornea hypoxia. Dk values above 66 are suitable for daily or continuous wear. The Dk values of hydrogel polymers could be increased with less cross-linking, but the lenses became fragile and the Dk values could not be increased above that of pure water.

Attempts to use fluorophores that respond to analyte concentrations within commercial contact lenses have been hindered by the inability to fix the fluorescent probes in the contact lens and the changes in analyte dependent fluorescence when in the contact lens chemical environment. Furthermore, typical probes have failed to respond in HEMA-type contact lenses.

For example, most publications on glucose sensing focus on boronic acid probes (as an alternative to glucose oxidase used in the current electrochemical glucometers) in which boronic acids bind reversibly to glucose. This binding alters the fluorescence spectral features obtained from several fluorophores, which can be correlated to the glucose levels in a sample of interest. With one exception, none of the previous boronic acid (BA) fluorescent probes developed for glucose sensing in buffer conditions were able to respond to the glucose levels within a contact lens. The one exception is a probe based on quinolinium derivatives which gave a small response to glucose in contact lens using a hydrogel polymer (Nelfilcon A) and washed out of the contact lens. Many other boronic acid probes provided no response to glucose in the hydrogel lenses.

Designing a suitable glucose sensitive fluorophore (Glu-SF), for inclusion in a glucose sensitive contact lens (Glu-CL) and for remote optical measurements of tear glucose, has met several barriers. Known Glu-SFs required ultraviolet (UV) or near-UV excitation and practical, portable light sources did not yet exist at the time of those previous attempts. Glu-SFs for longer wavelengths excitation were either not available or displayed minimal spectral changes. A barrier to the design of Glu-SFs was the rapidly changing polymer chemistry for contact lenses. A Glu-SF which responds in poly-hydroxyethyl-methacrylate (HEMA) hydrogels (HGs) from the 1990s may not respond in the current lenses based on silicone hydrogels (SiHGs) emerging after 2000.

Figure 4:
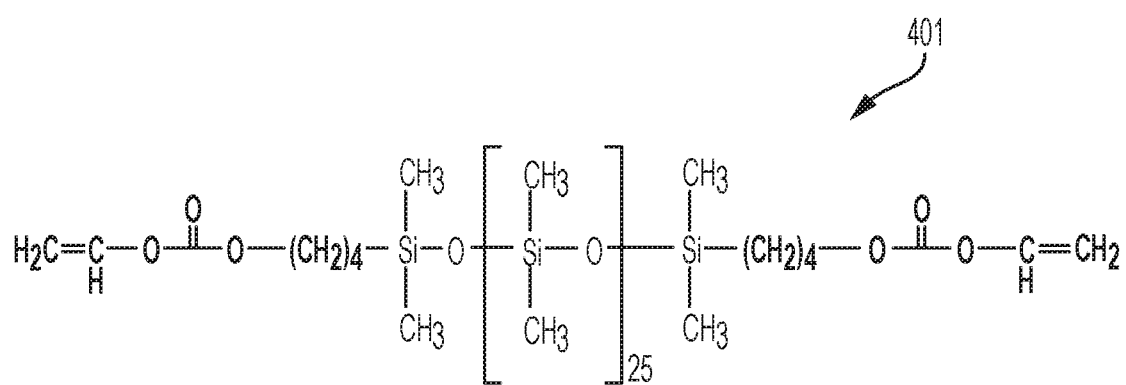
FIG. 4 is a monomer present in a SiHG contact lens, according to an embodiment.

This problem of hydrogel contact lenses, that they are fragile and the Dk values could not be increased above that of pure water, was solved by the use of silicone hydrogels (SiHG). A typical monomer is shown in FIG. 4 and contains a long silicone backbone and carbon-containing reactive groups at the ends for polymerization. Many different monomer combinations are used. These soft contact lenses contain variable proportions of cross-linkers to control the water content and structural rigidity. The most important feature of silicone hydrogels (SiHGs) is that the Dk values for oxygen transport are dramatically increased compared to non-silicone HGs. The Dk values are now about 3-fold larger than a comparable thickness of water. The first commercial SiHG lens (appearing in 1998) was popular with patients because of comfort and softness, but some patients described problems of eye dryness and inflammation. These adverse effects were discovered to be due to the hydrophobicity of silicone and interference with the tear layer. These problems were solved by making the lens surfaces hydrophilic using chemical or plasma surface oxidation. The resulting lenses found acceptance by a high proportion of the patients. Such lenses are approved for daily or long-term wear. Now, over 70% of new prescriptions for contact lenses are for SiHG lenses (SiHG-CL). Because of mass production, such SiHG-CL have become very inexpensive. As a consequence, in developed countries, one day use-and-disposal has become the preferred mode of use—even with extended wear lenses.

By including fluorophores in the contact lens, and using remote electronics to determine concentration of analyte, the cost of a Glu-CL can be reduced to be comparable with a plain SiHG-CL.

1.1 Overview of Probes and Materials

Figure 1B:
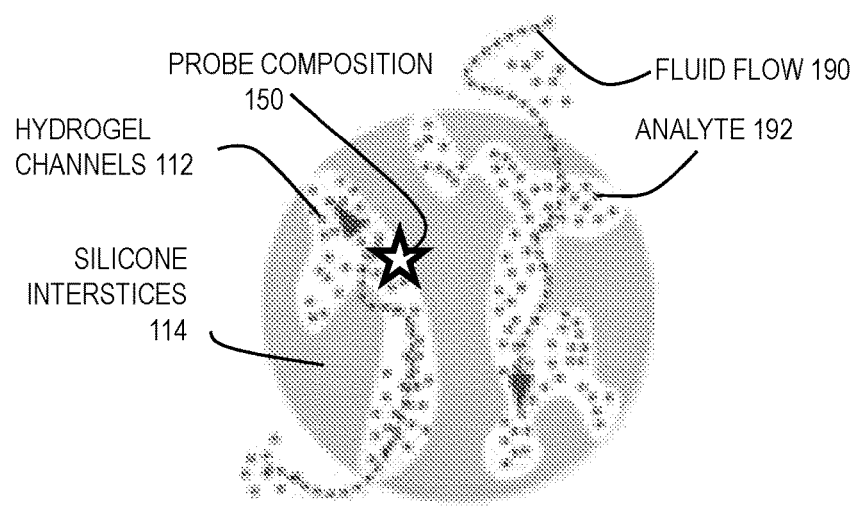

FIG. 1A and FIG. 1B are block diagrams that illustrate an example probe-substrate material 100, according to an embodiment. The probe-substrate material 100 (also called material for simplicity hereinafter) includes a SiHG substrate (SiHG) 110 and a probe composition 150 represented by a star symbol, preferably at a concentration that is observable at a remote monitor subsystem when an analyte is present in desirable quantities in a fluid contacting the material. The SiHG substrate 110 inherently includes a network of hydrogel channels 112 that allow the flow of aqueous solutions and a silicone backbone filling the interstices of the network of channels 112, called silicone interstices 114 hereinafter. The hydrogel channels are on the nanoscale, with widths that vary between about 10 nanometers (nm, 1 nm=$10^{-9}$ meters) and about 100 nm in some SiHG, and in other SiHG between 5-75 nm. It should be noted that because this range of channel sizes is smaller than the wavelength of light used in making measurements described herein, there is no scattering of light. The circles and ovals represent the cross sections of the channels 112 as they intersect the faces of a cube of depicted material 100. There may be many probe compositions 150 in an embodiment, or different probe compositions 150 to detect different analytes, as further described below. Note that each of the probe compositions 150 includes a hydrophilic part and a hydrophobic part so that the probe compositions 150 are found on a boundary (also called interface or silicone-water interface) between the hydrogel channels 112 and the silicone interstices 114. FIG. 1B is a close up cross section of such an interface, showing a fluid flow 190 represented by the dotted arrows through the hydrogel channels 112 and an analyte 192 within the fluid, each copy of the analyte 192 represented by a dot. Here the silicone interstices 114 are indicated with a gray fill. Note that the depicted probe composition 150 is disposed on the interface between a silicone interstices 114 and the fluid flow 190 and analytes 192 in a hydrogel channel 112. Although shown to illustrate the configuration during operation, the fluid flow 190 and included analyte 192 are not part of the material 100.

Figure 1C:
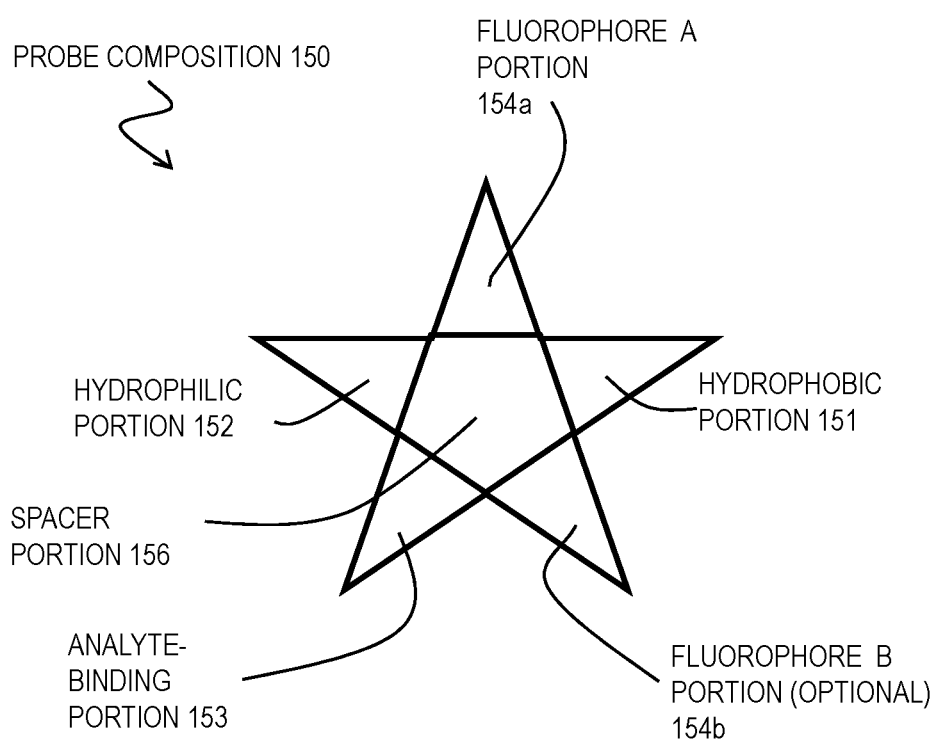
FIG. 1C is a block diagram that illustrates an example probe composition, according to an embodiment.

FIG. 1C is a block diagram that illustrates an example probe composition 150, according to an embodiment. The probe composition (also called a probe 150) comprises several portions, each portion comprising one or more atoms. The probe 150 includes a hydrophobic (non-polar) portion 151 that prefers to be with the non-polar regions of silicone interstices and a hydrophilic (polar) portion 152 that prefers to be among other polar molecules, such as water in the hydrogel channels 112. Because of this dual attraction, the probe compositions tend to reside at the interface of the hydrogel channels 112 and silicone interstices 114 and not to pass freely though the channels and flush out of the material 100 with the fluid flow 190. This means that the material substrate 110 can be loaded with the probe composition 150 to form material 100; and then the material 100 remains stable as the material 100 is used in a different sample fluids that flow through the hydrogel channels without dislodging many of the probes 150.

For use in an assay, the probe composition also includes at least one analyte-binding portion 153 to capture and bind a molecule of the analyte 192 in the fluid flow 190, if any. In addition, the probe 150 includes at least one fluorophore portion 154a that is configured to change a value of a property of its emitted fluorescent light when an analyte is bound to the analyte-binding portion 153 compared to a value of the property of its emitted fluorescent light when an analyte is NOT bound to the analyte-binding portion 153. In some embodiments, to ensure that the fluorophore portion 154a is properly spaced from the binding portion 153, a spacer portion 156 is included in the probe 150. In some embodiments, the change in property of fluorescence depends on the interaction of the fluorophore portion 154a with one or more other fluorophores or other functional portions, such as an election donor portion or electron acceptor portion or photon quenching portion or FRET partner portion, called fluorophore B portion 154b hereinafter. In such embodiments the spacer portion also ensures that the fluorophore B portion 154b is properly spaced from the fluorophore A portion 154a or the analyte-binding portion 153 or both. However, fluorophore B is generally not limited to FRET. For example, fluorophore B portion can also refer to the other part of a PET pair, or a quencher of fluorescence.

Figure 1D:
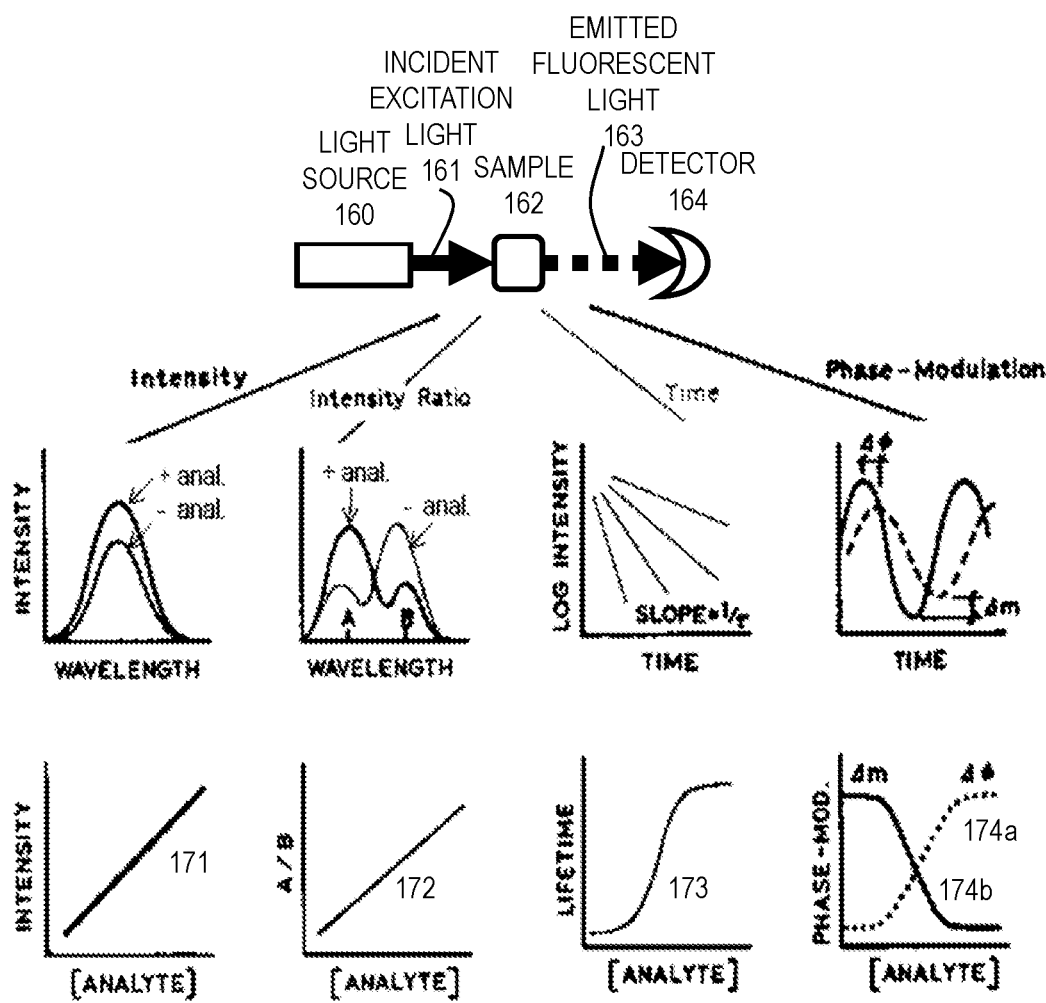
FIG. 1D is a block diagram that illustrates example fluorescent light properties that can be measured, according to various embodiments.

FIG. 1D are block diagrams that illustrates example fluorescent light properties that can be measured, according to various embodiments. In each embodiment, light 161 of a particular wavelength or wavelength band from a light source 160 is incident on a sample 162, such as material 100 with fluid 190 and analytes 192 therein. Fluorescent light 163 at a different wavelength or band is emitted in response and detected at an optical detector 164 that puts out a digital electrical signal or an analog electrical signal that can be digitized at an analog to digital converter (ADC). Although the emitted fluorescent light 163 is depicted in the same direction as the incident light for purposes of clarity of the diagram, the emitted fluorescent light 163 can be at a different angle than depicted. Example different properties of the emitted fluorescent light 163, among others known in the art, which can be measured include: intensity of the emitted light, represented by the column of graphs on the left; intensity ratio at two or more different wavelengths as indicated by the second column of graphs; intensity decay with time as indicated by the second column of graphs; and phase shift or modulation relative to the incident light The latter two properties both reflect the lifetime of the emitted fluorescent light 163 after the incident light is turned off., e.g., fluorescent lifetime after a pulse of incident light.

Referring now to the graphs of FIG. 1D, if any of the measurable properties from a probe composition 150 are found to depend on the concentration of the analyte 192 in the fluid 190 for a range of analyte concentrations of interest (e.g., glucose from 40 mg/mL to 300 mg/mL for a diabetic subject), then that probe composition 150 is suitable for forming material 100. The top graph in each column shows examples of different responses for two different concentrations of an analyte, assuming for purposes of illustration that there is a useful dependence of that property on concentration of analyte. The bottom graph in each column depicts calibration curves for each property assuming for purposes of illustration that there is a useful dependence of that property over a useful range of concentrations of analyte.

Still referring to the graphs of FIG. 1D, for example, the top graph on the left column shows that fluorescent intensity forms a peak in a wavelength band at low concentrations of analyte 192 (labeled as "− anal" in the graph). The same graph shows that fluorescent intensity forms a peak in the same wavelength band at high concentrations of analyte (labeled as "+ anal" in the graph); but, the graph shows the peak intensity value is greater for the high concentration than for the low concentration. If this relationship were to persist over the analyte concentration range of interest, the bottom graph in the column, with calibration curve 171, would result. Here the intensity of the peak increases with analyte concentration over a concentration range of interest. In this example, the intensity in the wavelength band is the property of the fluorescent light used to determine the concentration of the analyte.

Similarly, and still referring to the graphs of FIG. 1D the top graph on the second column from the left shows that fluorescent intensity forms peaks in two separate wavelength bands (called band A and band B in the graph) at low concentrations of analyte (labeled as "− anal" in the graph). The intensity of the first peak (band A) is less than the intensity of the second peak (band B). The same graph shows that fluorescent intensity peaks in the same two separate wavelength bands at high concentrations of analyte (labeled as "+ anal" in the graph); but, the intensity of the first peak (band A) is greater than the intensity of the second peak (band B). A ratio defined by dividing the intensity of the first peak (band A) by the intensity of the second peak (band B) is lower for low concentration of analyte and higher for the high concentration of analyte. If this relationship were to persist over the analyte concentration range of interest, the bottom graph in the column, with calibration curve 172, would result. Here the ratio of the intensities of the two peaks increases with analyte concentration over a concentration range of interest. In other embodiments, the ratio of the intensities of the two peaks decreases with analyte concentration over a concentration range of interest. In these examples, the ratio of the intensities in the two bands is the property of the fluorescent light used to determine the concentration of the analyte.

As another example from FIG. 1D, the top graph on the third column from the left shows that fluorescent intensity in a particular wavelength band decreases with time. The rate of decay is different for different concentrations of the analyte. The lifetime of the fluorescent response ($\tau$) is given by a reciprocal of a slope of a line in the graph of the log of the intensity in the wavelength band against time. The lifetime $\tau$ is lower for low concentration of analyte and higher for the high concentration of analyte 192. If this relationship were to persist over the analyte concentration range of interest, the bottom graph in the column, with calibration curve 173, would result. Here the lifetime ($\tau$) increases with analyte concentration over a concentration range of interest. In this example, the lifetime r is the property of the fluorescent light used to determine the concentration of the analyte.

In another example from FIG. 1D, the top graph on the fourth column from the left shows electric field changes in time associated with a modulation frequency f. The method uses intensity-modulated light at some modulation frequency f that is much less than the optical frequency. Light modulation frequencies f typically range from 10 megaHertz (MHz, 1 MHz=$10^6$ Hertz) to 300 MHz, but can be from 1 MHz to 10 gigaHertz (GHz, 1 GHz=$10^9$ Hz); while optical frequencies are in the range of terahertz (THz, 1 THz=$10^{12}$ Hertz). The solid curve shows the timing (phase, $\phi$) of the measured light modulations relative to that reference beam of light—with successive modulation peaks separated by $2\pi$ in phase for a wave period given by 1/f. The graph also shows an amplitude called a modulation for the wave which is related to the intensity. A measured field from emitted fluorescent light is given by the dashed curve and has a slightly different phase $\Delta\phi$ and modulation $\Delta m$ from the reference field. If the phase difference $\Delta\phi$ or the modulation difference $\Delta m$ from the reference changes with different concentrations of analyte 192, and if either or both were to persist over the analyte concentration range of interest, the bottom graph in the column would result. Here the phase difference $\Delta\phi$ given by the dotted line increases with analyte concentration over a concentration range of interest, providing calibration curve 174a; and, the modulation difference $\Delta m$ given by the solid line decreases with analyte concentration over a concentration range of interest, providing calibration curve 174b. In this example, either phase difference Δϕ or modulation difference Δm is the property of the emitted fluorescent light 163 used to determine the concentration of the analyte 192.

1.2 Overview of Method

Figure 2:
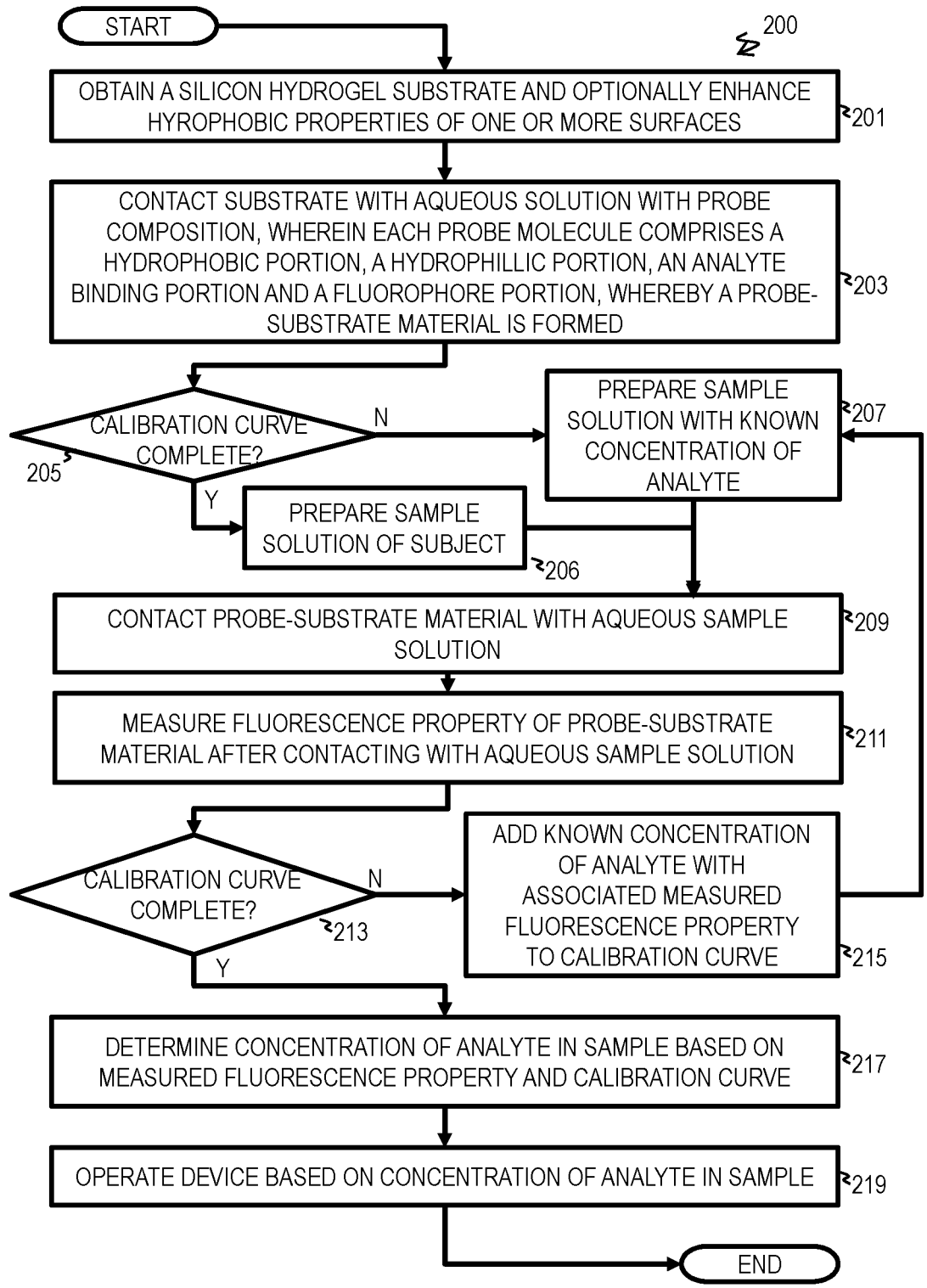
FIG. 2 is a flow chart that illustrates an example method for measuring the concentration of an analyte based on a probe-substrate material, as depicted in FIG. 1A, according to an embodiment.

FIG. 2 is a flow chart that illustrates an example method 200 for measuring the concentration of an analyte based on a material, as depicted in FIG. 1A, according to an embodiment. Although steps are depicted in FIG. 2 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 201, a silicone hydrogel substrate is obtained, such as SiHG-CL or a microfluidic device with the silicone hydrogel deposited in one or more sections of one or more channels or in one or more chambers or in one or more reservoirs, or some combination. In some embodiments, the surface of the substrate (e.g., the surfaces of a contact lens) has been treated to make it more hydrophilic, e.g., by oxidation. In some such embodiments, when it is desirable to have probes attach to one or more surfaces of the material instead or in addition to the internal interfaces between hydrogel channels and silicone interstices, the one or more surfaces are treated to enhance the hydrophobic properties of the surface. Examples of such treatment are described in more detail below with reference particular example embodiments. In some embodiments, step 201 includes forming a microfluidic device with the silicone hydrogel deposited in one or more portions of one or more channels or one or more chambers or one or more reservoirs, or some combination.

In step 203, the SiHG substrate is contacted with a aqueous solution with probe compositions 150 for a sufficient duration to obtain a target concentration of the probes in or on the material. The duration can be determined by experimentation for any particular application. As a result, a probe-substrate material 100 is formed. In some embodiments, step 203 involves soaking the material in the solution for the duration. In some embodiments, step 203 involves flushing the material or a microfluidic device including the material with the solution including the probes or otherwise agitating or heating the fluid to achieve the desired concentration of probes in the material within the available duration.

The step following step 205 depends upon whether there is a desired calibration curve for the desired analyte and fluorescent response from the probe, such as one or more of curves 171, 172, 172, 174a or 174b, described above, or some combination. Thus the method includes a branch point at step 205 to determine whether there is a completed calibration curve or one has to be generated or improved. If there is already a calibration curve of desired reliability that can be used, then control passes directly to step 206 described below. Otherwise, if there is no calibration curve or if an existing calibration curve is lacking in range or statistical convergence, then control passes first to step 207.

In step 207, an aqueous solution with known concentration of analyte is prepared as the sample solution. Any method can be used to produce the known concentration, such as adding a known amount to a known volume of blood or saline or artificial tears to emulate the fluid to be used as a sample from a subject. Control then passes to step 209, described below.

If there is already a calibration curve of desired reliability, then control passes to step 206 instead of step 207. In step 206, an aqueous sample solution is prepared. For example, a blood or urine sample is drawn. In embodiments in which the material is placed in situ, such as a contact lens into the tear fluid coating the subject's eye, then step 206 is omitted and control passes directly to step 209.

In step 209, the probe-substrate material is contacted with the aqueous sample solution (e.g., with known analyte concentration from step 207 or unknown analyte concentration from step 206). For example, in some embodiments the fluid sample is made to flow into a microfluidic device, under gravity, pressure or capillary action, or, in some embodiments, the material or microfluidic device including the material is submerged in the sample. In the example embodiments described below, a contact lens at least part of which is the probe-substrate material is inserted under the eyelids and in front of the cornea of the subject's eye.

In step 211, the calibration curve property of the fluorescent light emitted from the material in contact with the sample fluid is measured in response to excitation by the incident light. The system that excites fluorescence and determines and uses the value of the property related to analyte concentration is called herein a monitor subsystem. Any means known to excite, measure and use the property may be employed as the monitor subsystem, as described in the next section.

After step 211, the next step performed is based on whether there is already an adequate calibration curve, as indicated in step 213 that parallels step 205 described above. If the calibration curve is not complete, then the sample has a known concentration of the analyte and control passes to step 215 to add the measured property of the fluorescent light emitted from the sample and the associated known analyte concentration to the calibration curve. Control then passes back to step 207 to prepare the next sample solution with a known concentration of the analyte. After the loop represented by steps 207, 209, 211 and 215 is repeated enough times, the data converges on a calibration curve or trace that can be used to derive concentration of analyte from measurements of the property of the fluorescent light emitted from a sample with unknown analyte concentration, and the calibration curve is considered complete.

If the calibration curve is complete, then the sample is from a subject and has an unknown concentration of the analyte; and, control passes to step 217. In step 217, the concentration of the analyte in the sample is determined based on the calibration curve and the value of the property of the fluorescent light measured in step 21, described above.

In step 219 a device is operated based on the concentration of the analyte. For example, the value of the concentration of the analyte is presented on a computer or cell phone display device, as described below with reference to FIG. 31 or FIG. 33. In some embodiments, the value of the concentration is used to determine whether the subject has a condition, such as DED, keratitis, or diabetic hypoglycemia or hyperglycemia; and, to present data indicating the condition on the display device, or operate a device to administer remedial treatment, such as administering insulin to a subject with the condition of diabetic hyperglycemia. The device operated in step 219 is hereinafter called an analyte responsive device, or simply "responsive device."

1.3 Overview of Systems

Figure 3A:
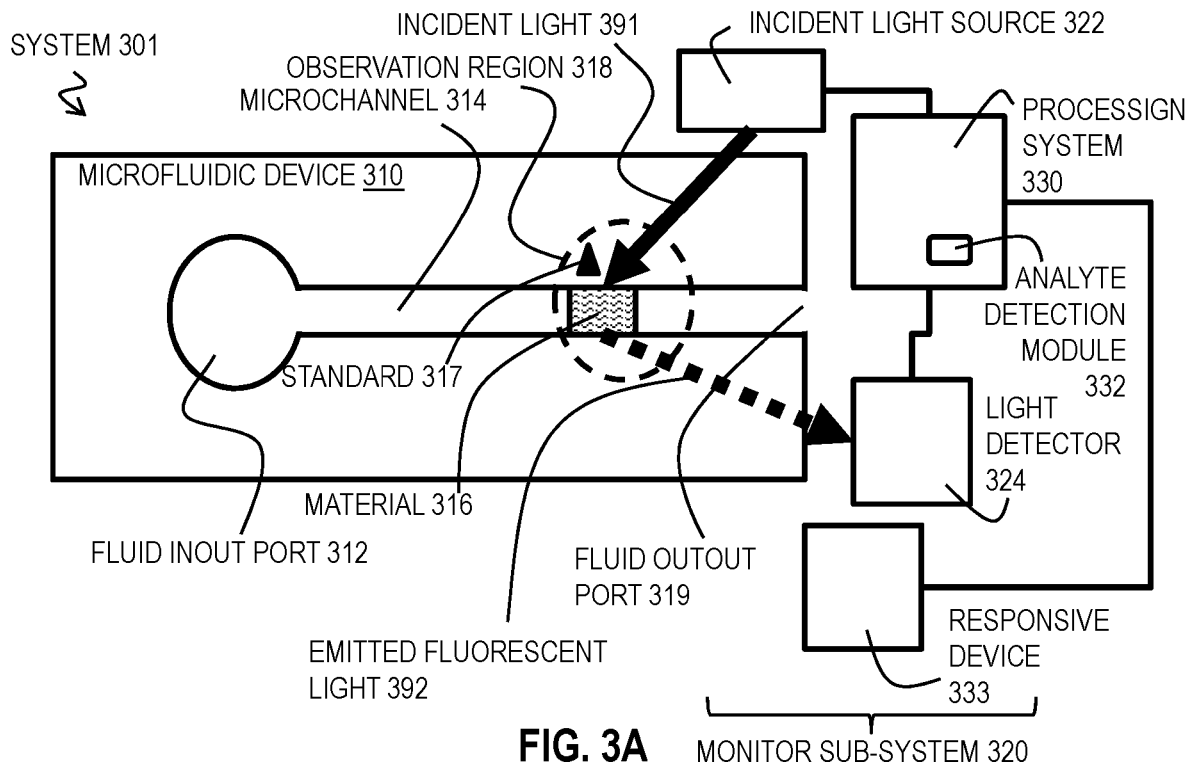
FIG. 3A and FIG. 3B are block diagrams that illustrate example systems that detect concentration of an analyte in fluid from a subject, according to some embodiments.
Figure 3B:
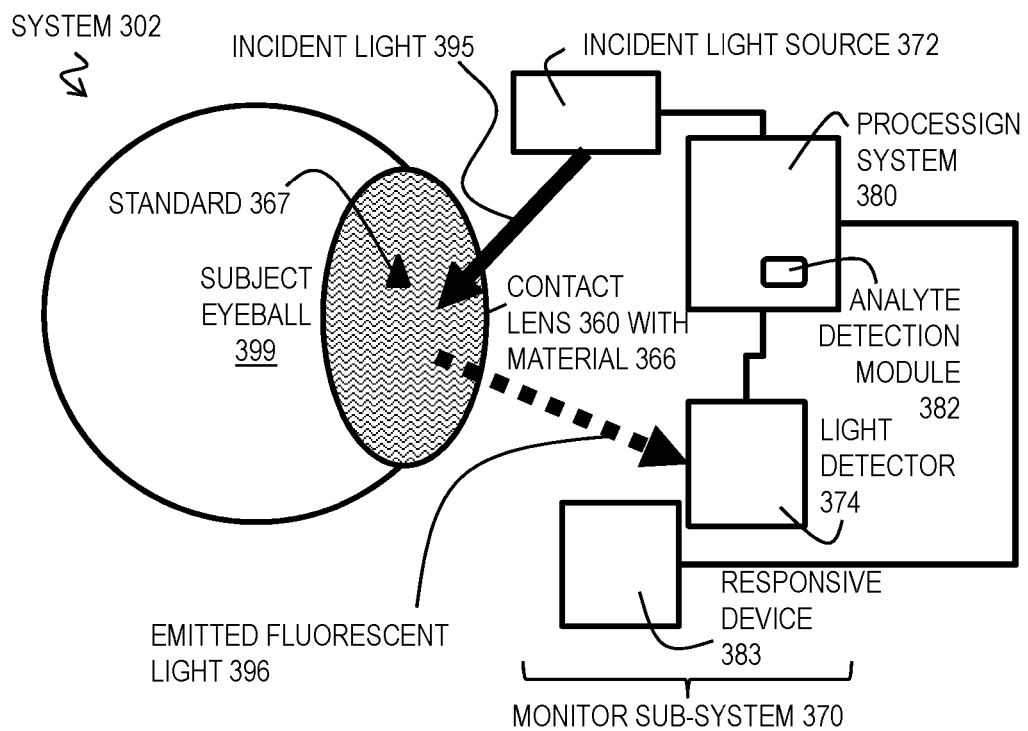

FIG. 3A and FIG. 3B are block diagrams that illustrate example systems that detect concentration of an analyte in fluid from a subject, according to some embodiments. FIG. 3A depicts an example system using a microfluidic device into which a sample solution is introduced; and, FIG. 3B depicts an example system using a contact lens placed in situ in the tear fluid of a subject's eye in front of the cornea and behind the closed eyelid.

FIG. 3A is a block diagram that illustrates an example microfluidic system 301 that detects concentration of an analyte in fluid from a subject, according to some embodiments, The system 301 includes a microfluidic device 310 and a monitor subsystem 320. The microfluidic device includes a non-hydrogel substrate, such as glass or PDMS into which is formed, by etching or injection molding or other process known, a fluid input port 312, a microchannel 314 having both width and depth in the range from 1 to 1000 micrometers (µm, also called microns, 1 micron $=10^{-6}$ meters), and a fluid output port 319, in fluid communication with a chamber or other basin or waste disposal (not shown). In a section called an observation region 318, a probe-substrate material 316, such as material 100, is disposed. In some embodiments, e.g. in some embodiments based on measuring fluorescence intensity with a calibration curve like 171, it is advantageous to include a standard 317 that has a known intensity in the fluorescent band of wavelengths. During operation, a sample solution is introduced at fluid input 312, flows through microchannel 324 and encounters the probe-substrate material 316.

Figure 31:
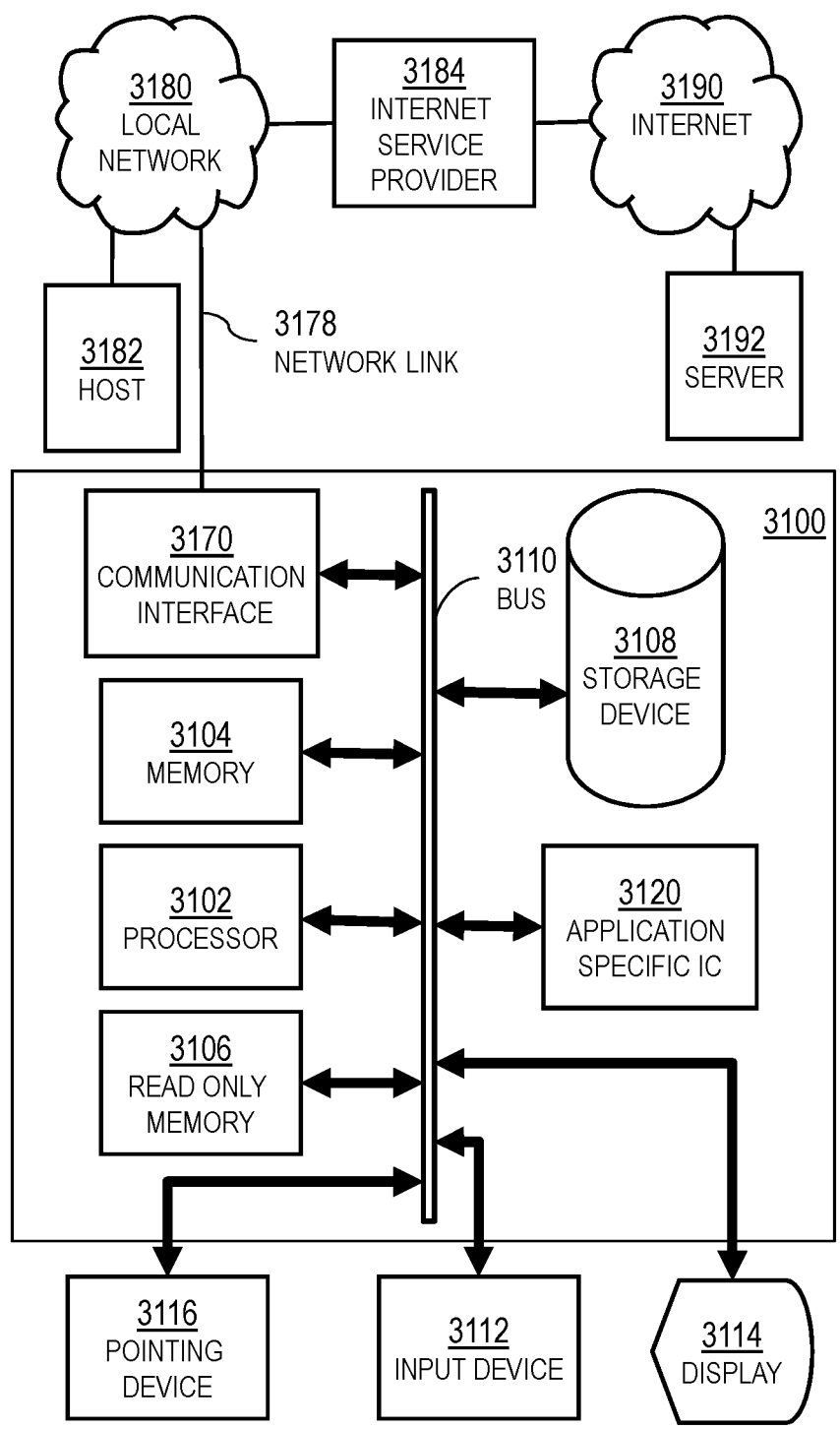
FIG. 31 is a block diagram that illustrates a computer system upon which an embodiment of the invention may be implemented.
Figure 32:
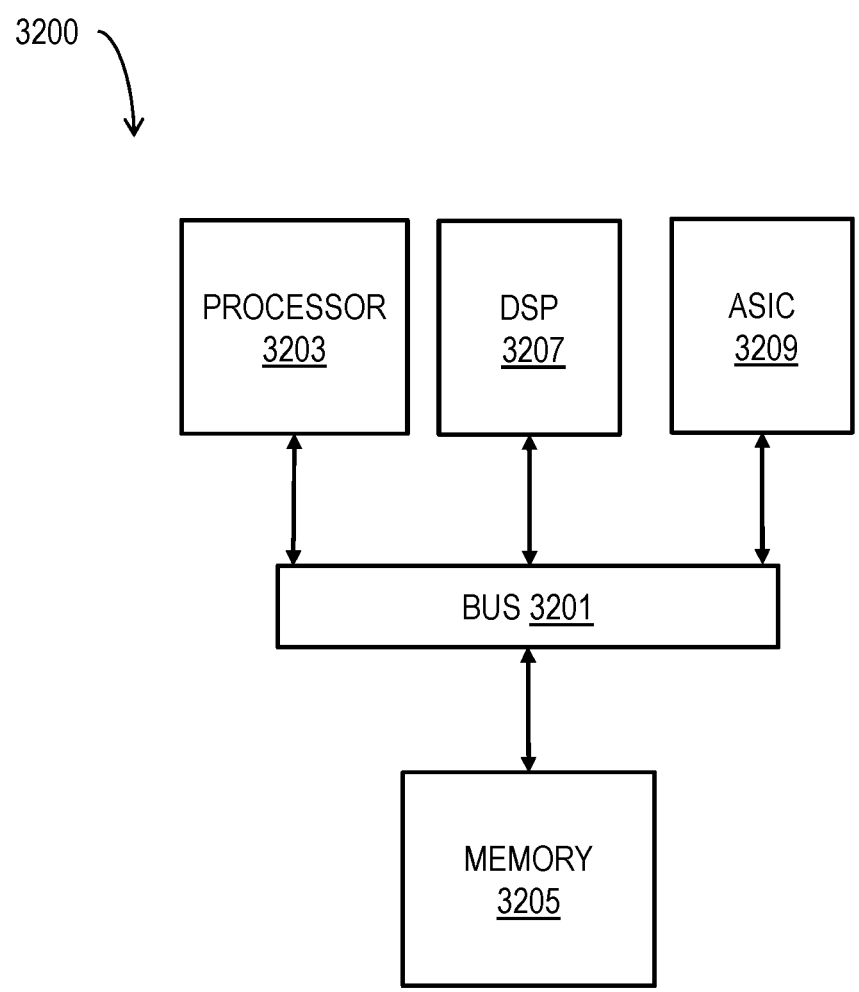
FIG. 32 illustrates a chip set upon which an embodiment of the invention may be implemented.
Figure 33:
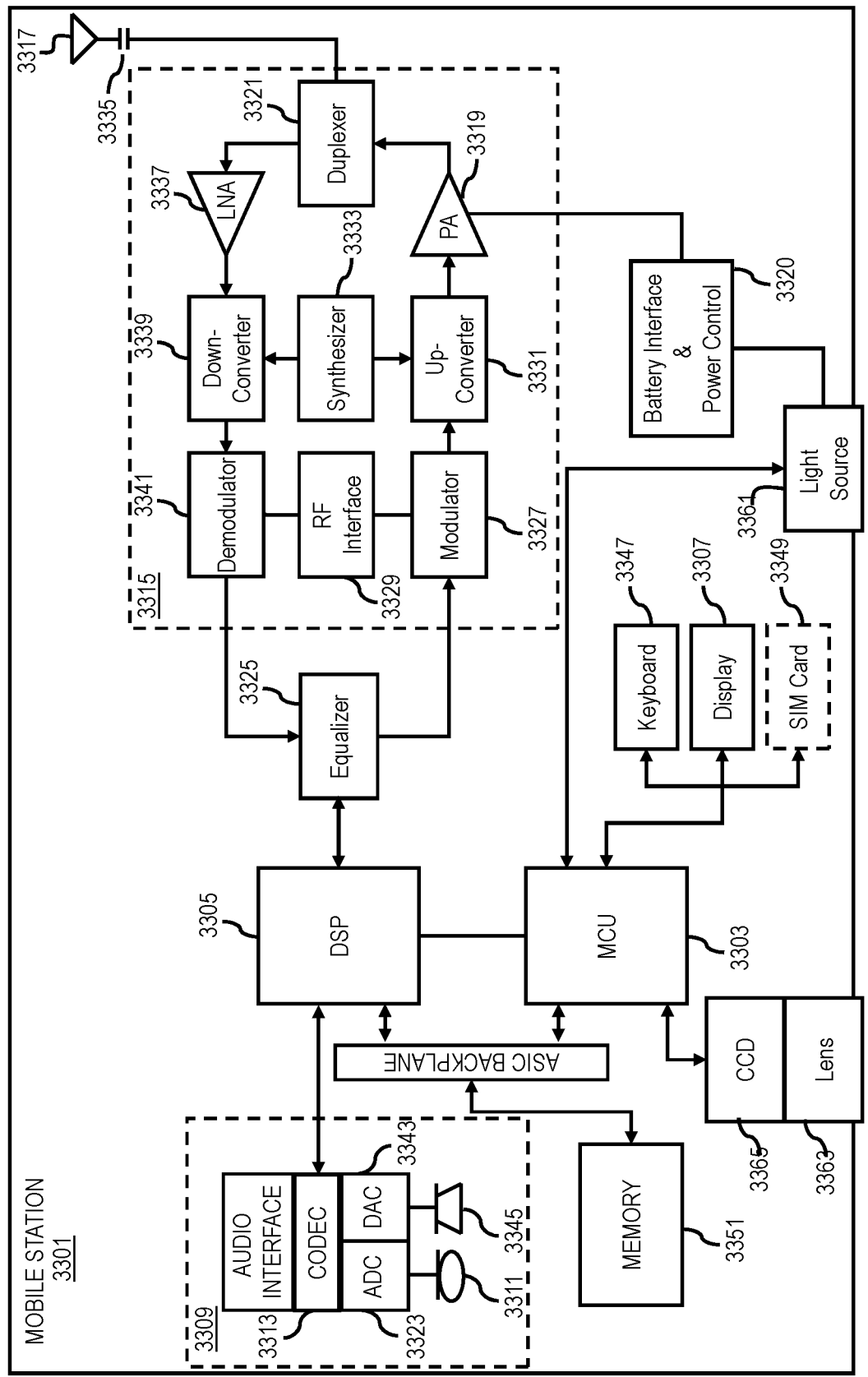
FIG. 33 is a diagram of exemplary components of a mobile terminal (e.g., cell phone handset) for communications, which is capable of operating in the system, according to one embodiment.

The monitor sub-system 320 provides the excitation light and makes the fluorescence measurements and determines the concentration of the analyte in the fluid passing through the material 316. To avoid contaminating the sample fluid, it is advantageous if no component of the monitor sub-system contacts the fluid in the microfluidic device 310. The monitor sub-system 320 includes incident light source 322, light detector 324, processing system 330 and responsive device 333. An analyte detection module 332 is implemented as hardware, firmware or software, or some combination, in processing system 330 to operate the processing system 330 and light source 322 and detector 324 and responsive device 333 as described in the method 200 of FIG. 2. Although incident light 391 and emitted fluorescent light 392 are depicted to illustrate operation of the subsystem, they are not part of the sub-system except during operation. In the illustrated embodiment, the processing system 330 is in communication with the incident light source 322, light detector 324 and responsive device 333 through one or more wired or wireless connections. In some embodiments, one or more of these components are included in a computer system as depicted in FIG. 31, chip set as depicted in FIG. 32, or mobile terminal or cell phone as depicted in FIG. 33.

The monitor sub-system 320, as noted above and depicted in FIGS. 31, 32, and 33, includes incident light source 322, light detector 324, processing system 330 and responsive device 333. The light source 322 includes a light source, such as a laser, light emitting diode (LED), pulsed laser diode (LD), UV LED, incandescent lamp, fluorescent lamp, including any ultraviolet (UV) source, and any optical couplers used to condition the light (e.g., to polarize, filter, modify wavelength, modify amplitude, modify phase or otherwise delay) and direct the light onto the material 316. Optical couplers include one or more of an optical filter, a polarization controller, an optical amplifier, a frequency doubler, injection locking, fiber-optical circulator, fiber coupler, and free-space optical components (e.g., mirrors, lenses, polarizers, open space, vacuum space, etc.) individually or collectively. The light detector 324 includes one or more optical couplers and single, paired or one or two dimensional arrays of single or paired detectors that output analog or digital electrical signals, along with any analog to digital converter (ADS), filters or other electronic components useful to condition the electrical data for processing by the processing system 330. The processing system includes one or more of the computer system depicted in FIG. 31, chip set depicted in FIG. 32, or smart cell phone depicted in FIG. 33. The analyte detection module 332 is configured to: operate the light source 322 to produce desired properties of the incident light to direct onto the material 316, including operating any motors or actuators to point or tune the light; to determine the duration and frequency of measurements to be made at the detector 324; to condition the data after the data is received from the detector 324, including determining the property of the fluorescent light; to use or construct the calibration curve; to determine the analyte concentration; and to operate the responsive device 333 based on the value of the concentration of the analyte.

FIG. 3B is a block diagram that illustrates an example in situ system 302 that detects concentration of an analyte in fluid from a subject, according to some embodiments, The system 302 includes a monitor sub-system much as described above for system 301 and, instead of a microfluidic device 310, a contact lens 360 with at least a part including a probe-substrate material 366. For example, in some embodiments based on measuring fluorescence intensity with a calibration curve like 171, it is advantageous to include a standard 367 that has a known intensity in the fluorescent band of wavelengths. During operation, the contact lens 360 is inserted in front of a cornea of an eyeball 399 of a subject typical of contact lens locations when the eyelids are closed. In situ tear fluid makes up the sample solution. The monitor sub-system 370 is made up of an incident light source 372, light detector 374, processing system 380, responsive device 383 and analyte detection module 382 configured for operation with the material 366 of contact lens 360, but otherwise analogous to those items 320, 322, 324, 330, 333 and 332, respectively, described above. Similarly, the incident light 395 and emitted fluorescent light 396 are particular to the material 366 of contact lens 360, but otherwise analogous to the incident light 391 and emitted fluorescent light 392 described above.

Although processes, equipment, and data structures are depicted in FIG. 3A and FIG. 3B as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts. For example, in some embodiments, the light source 322 is in autonomous mode and operated independently of the processing system 330, so that the communication connection between them is omitted.

2. Example Analyte Embodiments

Recent developments in silicone hydrogel contact lens (SiHG-CL) and fluorescent probes provide an opportunity to perform measurements of electrolyte concentrations with specially labeled (probe composition-infused) contact lenses for detection of dry eye disease. One of these developments, as mentioned earlier in this disclosure, is the existence of hydrogel channels or nanochannels (silicone interstices) within the silicone hydrogel allowing the flow of aqueous solutions through the lens. Embodiments disclosed below include probe compositions that may be anchored within the silicone interstices yet still have a portion exposed to aqueous flow through these nanochannels useful for measuring one or more analytes. Note that one of the analytes 192 which may be measured is glucose, and these embodiments are discussed more fully in Section 3 below.

The two main forms of dry eye disease are aqueous deficient dry eye (ADDE) and Evaporative dry eye (EDE). ADDE and EDE are highly correlated with an electrolyte imbalance in tears. High electrolyte concentrations is regarded as the most accurate and objective biomarker for DED. For this reason, probe compositions 150 have been developed for detecting various electrolyte concentrations for use in a SiHG-CL.

Figure 5A:
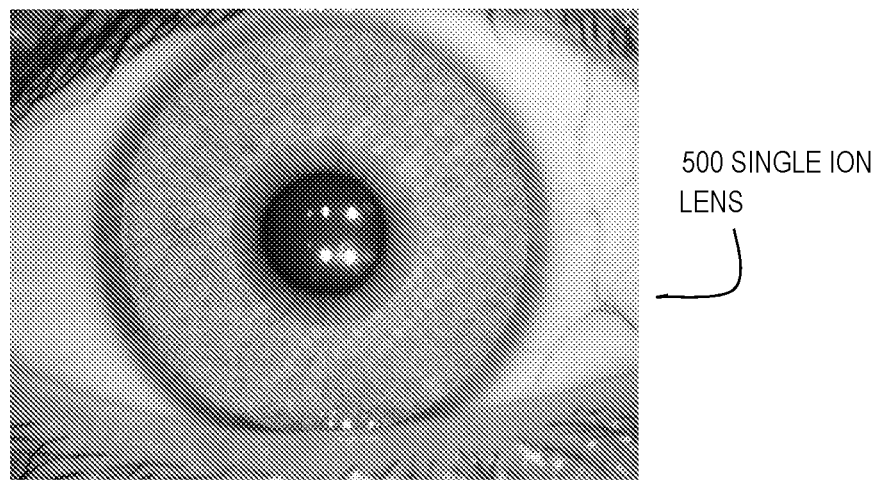
FIG. 5A and FIG. 5B are images that illustrate a contact lens that can be crafted using materials containing probe compositions to detect one or more various analytes, including glucose, according to various embodiments.
Figure 5B:
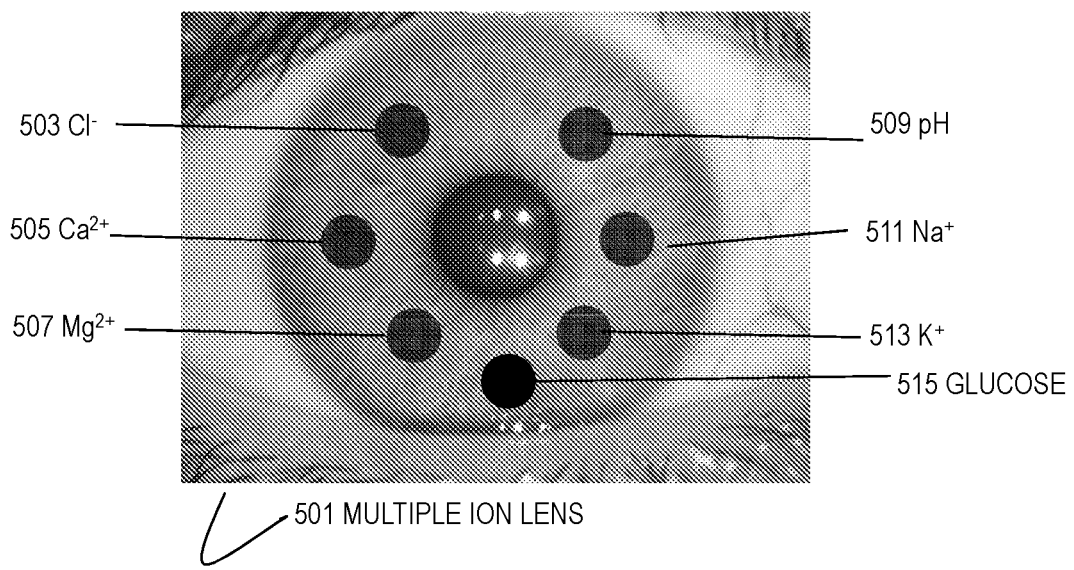

FIG. 5A and FIG. 5B are images that illustrate a contact lens that can be crafted using materials containing probe compositions to detect one or more various analytes such as the ones shown, including glucose, according to various embodiments. A multiple ion lens is one of the disclosed embodiments herein, and it uses a material incorporating various probe compositions disclosed herein such that the concentrations of one or more of the following electrolytes can be detected: pH (concentration of $H^+$) using probe composition 509, $Na^+$ using probe composition 511, $K^+$ using probe composition 513, $Ca^{2+}$ using probe composition 505, $Mg^{2+}$ using probe composition 507, $Cl^-$ using probe composition 503, and glucose using probe composition 515. A lens with the ability to detect one or more of these electrolytes may be constructed using a material having embedded therein probe compositions 150 designed to detect the concentration of these electrolytes.

Below are specific embodiments of probe compositions for detecting various electrolytes.

2.1. Probe Compositions Useful for Measuring pH Based on SNARF Probes

As mentioned in the discussion of FIG. 1C, embodiments of probe compositions 150 disclosed for measuring pH levels in tears include at least a hydrophilic portion 152, hydrophobic portion 151, an analyte binding portion 153.

Figure 6A:
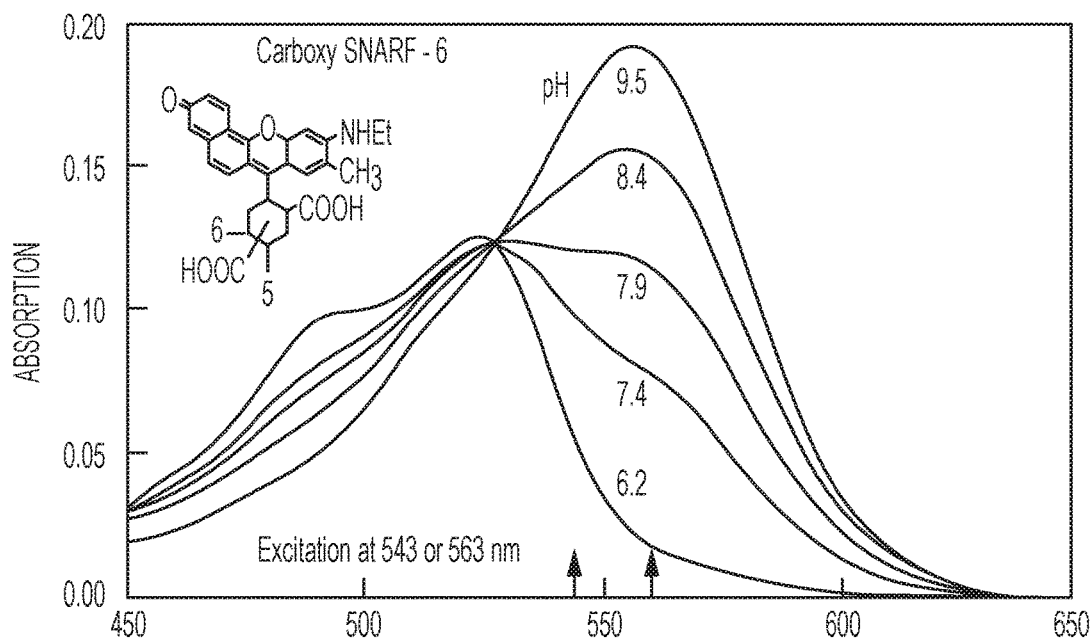
FIG. 6A is graph that illustrates an example carboxy SNARF-6 absorption spectra and effect of pH on the spectra, according to an embodiment.
Figure 6B:
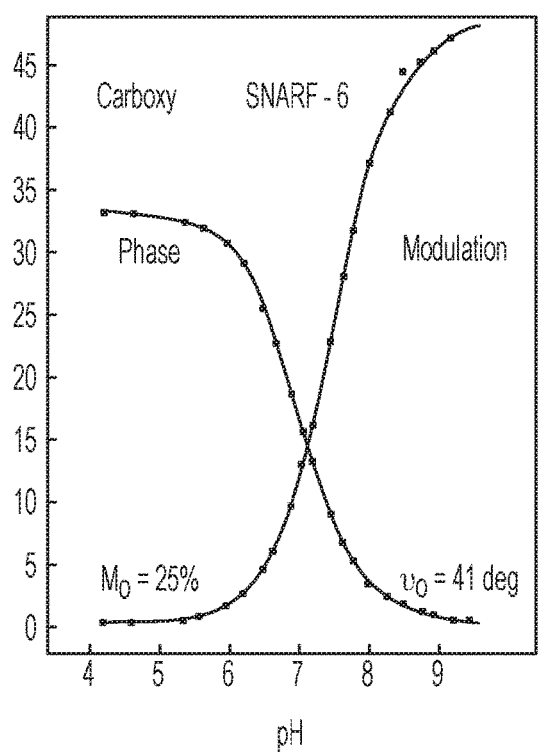
FIG. 6B and FIG. 6C are graphs that illustrate example time dependent decays recovered from full frequency-domain measurements and analysis at a pH where the total steady state intensities are close to equal, according to an embodiment.
Figure 6C:
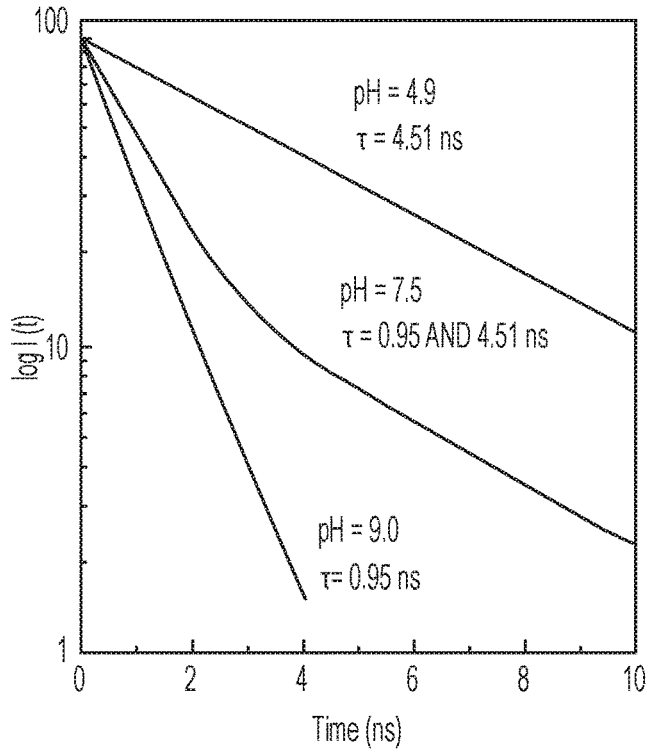

Embodiments of probes for use in SiHG-CL's may include known pH probes of the seminaphto-fluorescein (SNAFL) and seminaphtorhodafluors (SNARF) series. SNARF and SNAFL probes display changes in their absorption and emission spectra and also display changes in lifetime on pH-induced ionization. Embodiments are disclosed of probe compositions having hydrophobic alkyl side chains attached to or in chemical communication with SNARF-based probes capable of binding to the silicone rich region of the lenses. The SNARF family probes are themselves useful components of these probe compositions containing said side chains. FIG. 6A is graph that illustrates an example carboxy SNARF-6 absorption spectra and effect of pH on the spectra, according to an embodiment. FIG. 6B and FIG. 6C are graphs that illustrate example time dependent decays recovered from full frequency-domain measurements and analysis at a pH where the total steady state intensities are close to equal, according to an embodiment. FIG. 6A through FIG. 6C simply demonstrate that a SNARF family of probe, known commercially as carboxy-SNARF-6, is a useful component of a probe composition embodiment. As can be seen in FIG. 6A, the absorption spectral peak amplitude or wavelength varies widely with varying levels of pH (traces shown for pH values of 9.5, 8.4, 7.9, 7.4 and 6.2, respectively). For this reason probe compositions synthesized with this component are useful for determining pH using excitation-ratiometric or emission-ratiometric measurements. FIG. 6B shows a there is a pH-dependent change in average lifetime, which was recovered from full frequency-domain using a single modulation frequency. This change in phase angle shows that the mean decay time changes from 4.51 nanoseconds (ns) at low pH to 0.95 ns at high pH.

For this reason, these differences are exploited for use in correlating these changes to a given pH level in tears. The addition of a hydrophobic carbon side chain to these probes results in a probe composition 150 embodiment useful for Si-HG contact lenses (SiHG-CL).

2.2. Alternate pH Detecting Probe Compositions

In addition to modified SNARF probe compositions mentioned above, quinolinium based (e.g., hydroxyquinoline) probe compositions may be used for detecting pH. FIG. 7A is a chemical diagram that illustrates an example synthesis scheme for a probe composition for useful to measure and detect pH in a contact lens, according to an embodiment. FIG. 7B is a set of images that illustrates how an example Quin C-18 probe fluoresces at various pH levels when exposed to UV light, according to an embodiment. It was discovered that a 8-18 alkyl or allyl side chain is useful for binding the probe composition in the particular silicone interstices of the SiHG contact lens. In the embodiment of FIGS. 7A and 7B, an 18-carbon side chain was used.

FIG. 7A shows a synthesis scheme 701 for embodiments of probe compositions used to measure and detect pH (concentration of hydrogen ion, $H^+$) in a contact lens. Hydroxyquinoline 703 was reacted with 1-bromo-octadecane to form probe composition 150 forms 705, 707, 709. As used herein, 705, 707, 709 are collectively referenced as "6OH—N—C18H37-QBr" or HQ-C18.

Structures 705, 707, and 709 differ based on the level of ionization of the oxygen in the hydroxyl group. Depending on the pH, the hydroxyl group will be in the form $OH^-$ (705), $O^-$ (707), or OH (709). FIG. 7B shows how the probe 150 fluoresces differently at various pH levels when exposed to UV light. Image 711 indicates a clear lens in ambient light at a pH of 4.0. Image 715 indicates a yellow tint in ambient light at a pH of 10.0. Image 717 indicates a yellow glow in UV light at a pH of 10.0. Image 713 indicates a blue glow in UV light at a pH of 4.0.

The 6OH—N—C18H37-QBr probe composition has been shown to be useful for detecting pH changes in a SiHG-CL. This probe composition 150 displays change in both the absorption and emission spectra. Because both emission and absorption spectra change, the pH can be measure using either the excitation or emission intensity ratios. FIG. 8 is a graph that illustrates an example excitation spectra (left) and emission spectra (right) of 6-OH—N—C18H37-QBr in Biofinity™ contact lens in water, according to an embodiment. Because of the differences in the spectra at various pH levels, the probe composition 150 is suitable for the detection of pH in a SiHG-CL because it not only responds to changes in pH, but due to its hydrophobic side chain, it will not wash out of the contact lens. The probe composition bound strongly to a SiHG-CL and could not be washed out by repeated rinsing.

Figure 9:
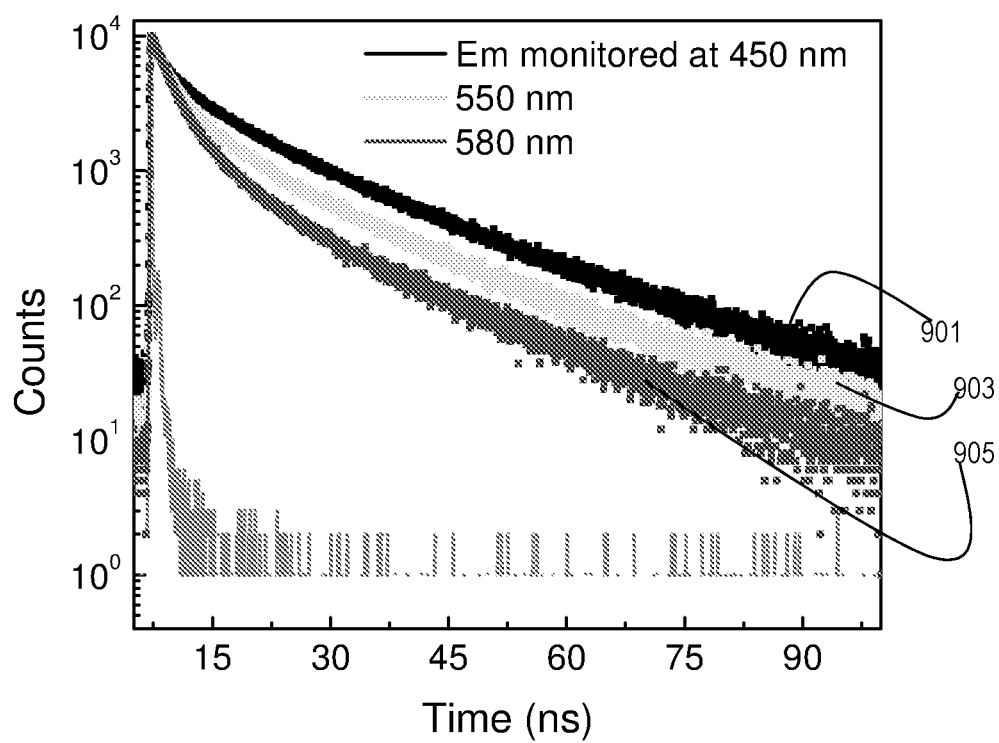
FIG. 9 is a graph that illustrates example intensity decay of 6OH—N—C18H37-QBr in a Biofinity™ contact lens in water, according to an embodiment.

Not only does the embodiment probe composition, 6OH—N—C18H37-QBr, display changes in spectral shifts at varying pH levels, but there is also a significant effect of pH on lifetime of the fluorescence intensity. FIG. 9 is a graph that illustrates example intensity decay of 6OH—N—C18H37-QBr in a Biofinity™ contact lens in water, according to an embodiment. Point clusters 901, 903, and 905 represent the emission monitored at 450 nm, 550 nm, and 580 nm, respectively.

An alternate structure which may be used as a pH probe is 6OH—N-Allyl-QBr or HQ-C3, below:

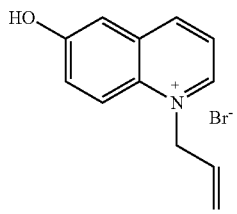

Figure 10:
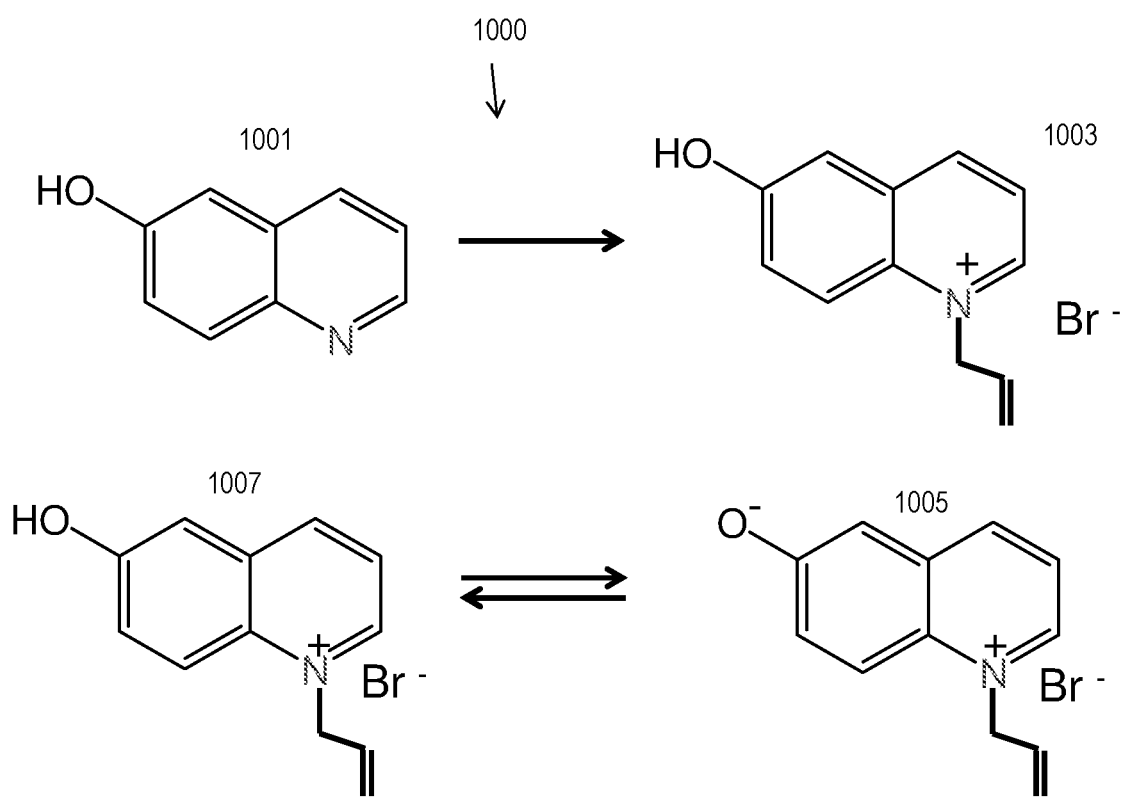
FIG. 10 is a chemical diagram that illustrates an example synthesis scheme for 6-OH—N-Allyl-QBr, according to an embodiment.

FIG. 10 is a chemical diagram that illustrates an example synthesis scheme for 6-OH—N-Allyl-QBr, according to an embodiment. This synthesis scheme is similar to the one shown in FIG. 9. Hydroxyquinoline 1001 is reacted with a three carbon hydrocarbon to form three forms of 6-OH—N-Allyl-QBr, existing in equilibrium with one another. These are represented as structures 1003, 1005, and 1007, and are collectively known herein as 6-OH—N-Allyl-QBr. As with The 6OH—N—C18H37-QBr, the 6-OH—N-Allyl-QBr probe composition has been shown to be useful for detecting pH changes in a SiHG-CL. This probe composition displays change in both the absorption and emission spectra. Because both emission and absorption spectra change, the pH can be measure using either the excitation or emission intensity ratios.

Figure 11:
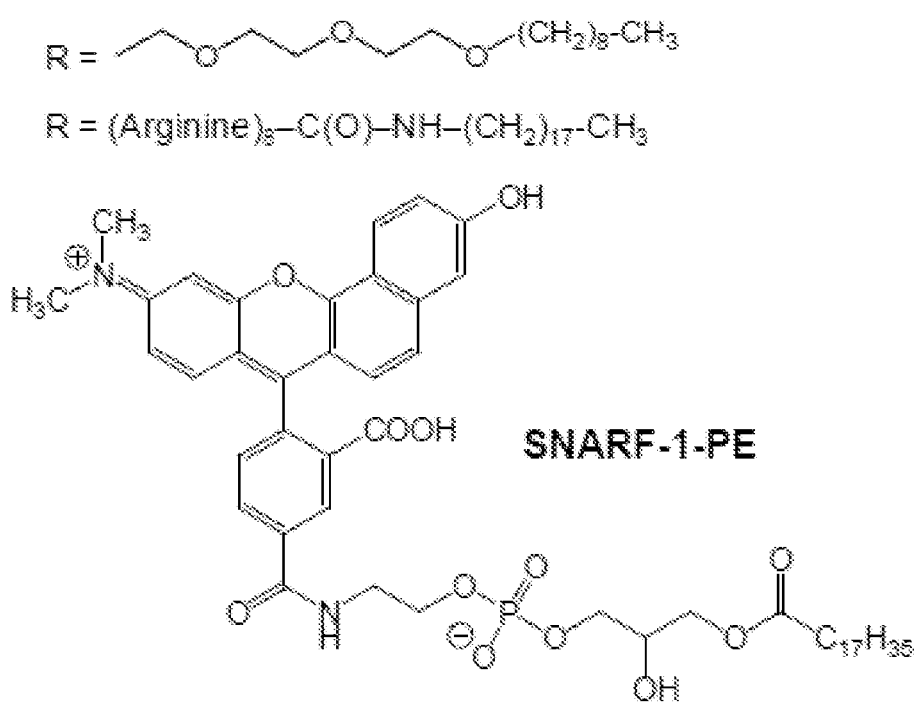
FIG. 11 is a chemical diagram that illustrates example hydrophobic side chains which may be incorporated into a certain pH-detecting probe compositions disclosed, such that the hydrophobic portion binds the probe composition at an interface in SiHG lens, as well as an example pH probe having a hydrophobic side chain, according to an embodiment.

FIG. 11 is a chemical diagram that illustrates example hydrophobic side chains which may be incorporated into a certain pH-detecting probe compositions disclosed, as well as an example pH probe having a hydrophobic side chain, such that the hydrophobic portion binds the probe composition at an interface in SiHG lens, according to an embodiment. The R groups of FIG. 11 are hydrophobic side chains which may be incorporated into a certain pH-detecting probe compositions disclosed, such that the hydrophobic portion binds the probe composition at an interface in SiHG-CL. In this embodiment, the side chains contain separating units of polyethylene glycol or arginine peptide. The main molecule shown in FIG. 11 is a probe composition consisting of SNARF-1 bound to lyso-phosphophatidylcholine (lyso-PE). This embodiment of a probe composition is referred to as SNARF-1-PE herein. This structure is formed by coupling a commercially available active ester of SNARF-1 with lyso-PE. Advantages of this embodiment are that it may be more easily and spontaneously bound to the SiHG-CL. Lyso-PE is charged and so the probe composition therefore is unlikely to fully enter the silicone regions of the lenses. This is useful, as the probe compositions advantageously straddle the channels such that the analyte binding portions are exposed to the aqueous environment. If the probe composition is wholly soluble in the silicone portions of the SiHG-CL, then it would not be available to bind (and therefore detect) various analytes. Another advantage of the SNARF-1PE probe composition is that the lyso-PE micelles are approximately 4 nm in diameter, which is small enough to enter the nanochannels of various SiHG-CL (which are about 50 nm in width).

2.3 Example $Na^+$ and $K^+$-Detecting Probe Compositions

There is speculation that $K^+$ has specific effects in DED because, in contrast to other electrolytes, $K^+$ has an approximate 5-fold higher concentration in tears than in blood serum. It is also believed that the $Na^+$ concentration may affect the severity of the DED condition. For this reason, probe composition embodiments can detect these analytes. As with earlier probe compositions, these embodiments are tailored for suitability in a contact lens or a similar material.

Figure 12:
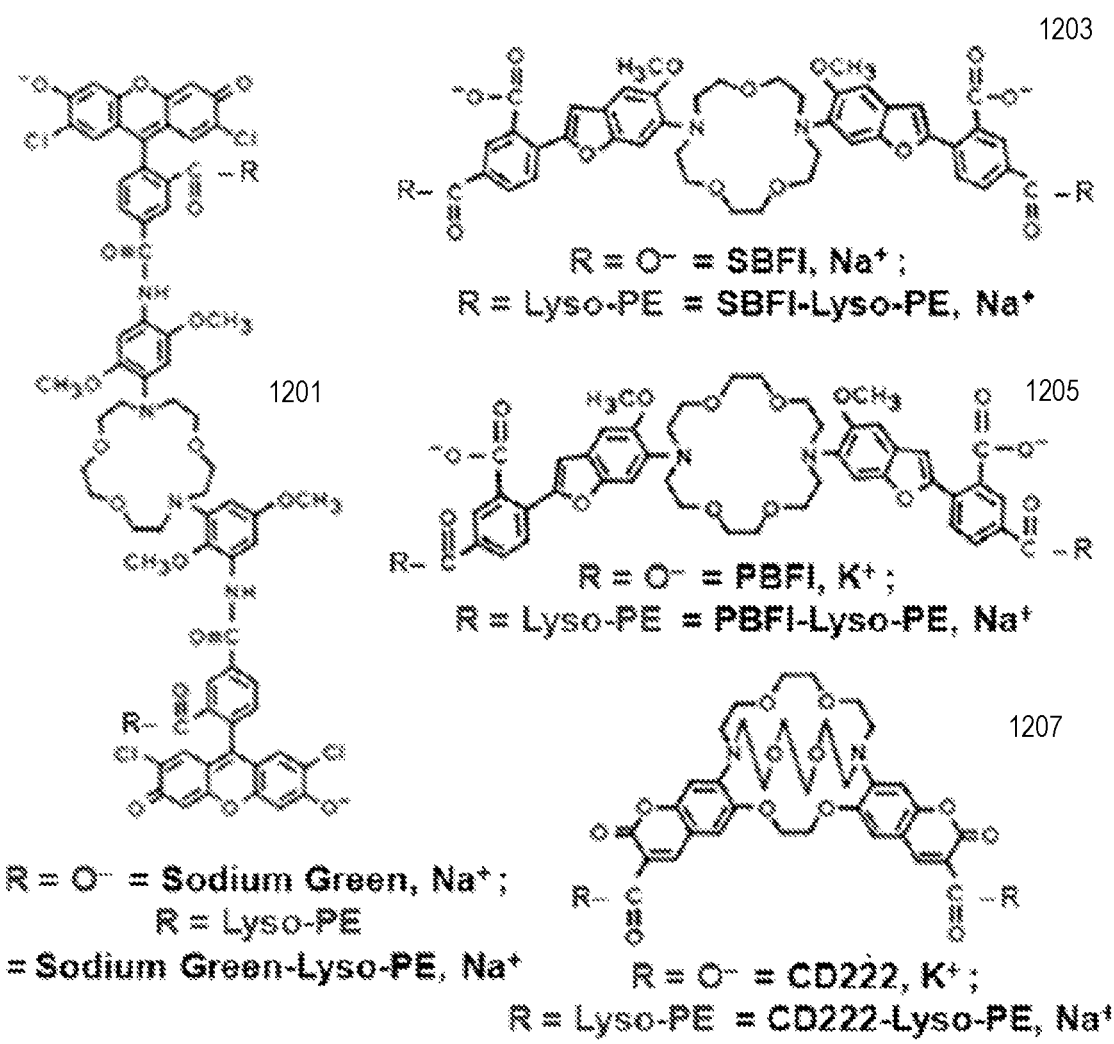
FIG. 12 is a set of chemical diagrams that illustrate example chemical structures of an $Na^+$ probe and ultraviolet (UV) analogues (i.e. SBFI), for use with UV light, according to various embodiments.

Fluorescent probes for $Na^+$ and $K^+$ are based on azacrown ethers attached to fluorophores using the nitrogen atoms. FIG. 12 is a set of chemical diagrams that illustrate example chemical structures of an $Na^+$ probe and ultraviolet (UV) analogues for use with UV light (SBFI), according to various embodiments. Structure 1201 is a visible wavelength $Na^+$ probe composition based on a Sodium Green base, but where the R groups may be lyso-PE. As with the above, the purpose of the lyso-PE would be to keep the probe composition partially exposed to the aqueous environment, and not wholly submerged within the hydrophobic portions of the contact lens. Structures 1203 and 1205 are yet other embodiments of probe compositions and comprise a sodium-binding benzofuran isophthalate (SBFI) molecule (for detecting $Na^+$) and a potassium-binding benzofuran isophthalate (PBFI)(for detecting $K^+$), respectively, modified with lyso-PE at the respective R groups. Another embodiment of a probe composition for detecting $K^+$ consists of the commercially available coumarin-based probe known as CD222 modified with a lyso-PE side chains in the "R" position (structure 1207) as shown in FIG. 12.

Figure 13A:
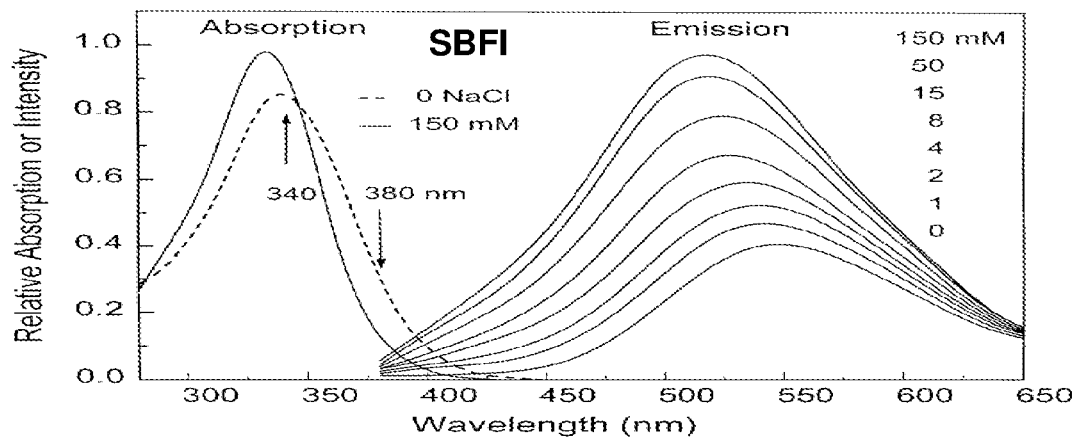
FIG. 13A is a graph that illustrates example $Na^+$ and $K^+$ dependent emission spectra of SBFI, according to various embodiments.
Figure 13B:
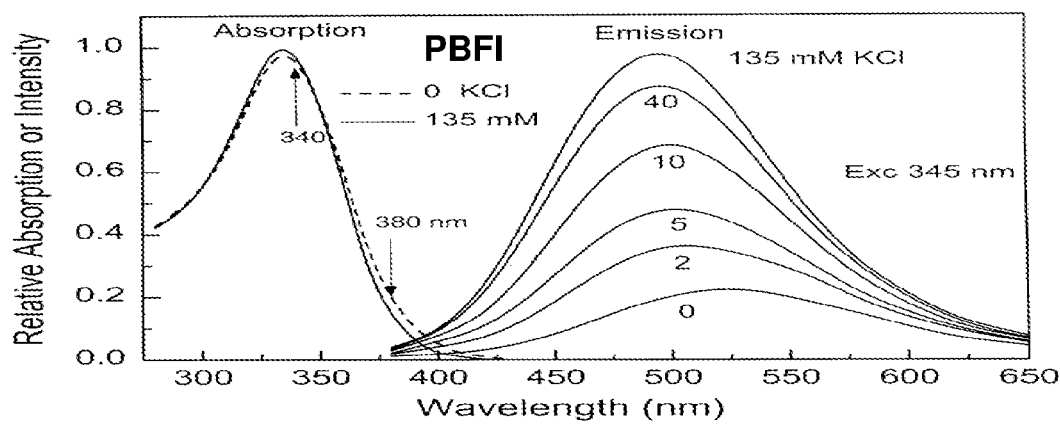
FIG. 13B is a graph that illustrates example $Na^+$ and $K^+$ dependent emission spectra of PBFI, according to an embodiment.

Correspondingly, FIGS. 13A and 13B show that the emission spectra of SFBI and PBFI, respectively. FIG. 13A is a graph that illustrates example $Na^+$ and $K^+$ dependent emission spectra of SBFI, according to various embodiments. FIG. 13B is a graph that illustrates example $Na^+$ and $K^+$ dependent emission spectra of PBFI, according to an embodiment. As can be seen, the emission spectra vary based on varying levels of concentration, which is indicated in the graph in various (mM) levels. As such, these probe compositions would be useful for correlating spectra with concentration levels.

2.4 Example $Mg^{2+}$ and $Ca^{2+}$-Detecting Probe Compositions

It is not yet known for certain the role of $Mg^{2+}$ and $Ca^{2+}$ in DED because means for measuring these ions has not been previously available. However, it has been suggested increased $Ca^{2+}$ concentrations could indicate some form of ocular defect because calcium levels in tears is typically 5-fold lower in tears than blood. In the likelihood that means for detecting is $Mg^{2+}$ and $Ca^{2+}$ ions in tears becomes necessary for any reason, embodiments of probe compositions have been developed that are useful for detecting concentrations of these elements. As with the previous embodiments, the probe compositions are developed so that they traverse the silicone-hydrogel interface in a SiHG-CL with a hydrophobic portion anchored in the silicone interstices and the analyte binding portion in the hydrogel nanochannels to detect analytes in the aqueous flow.

Figure 14:
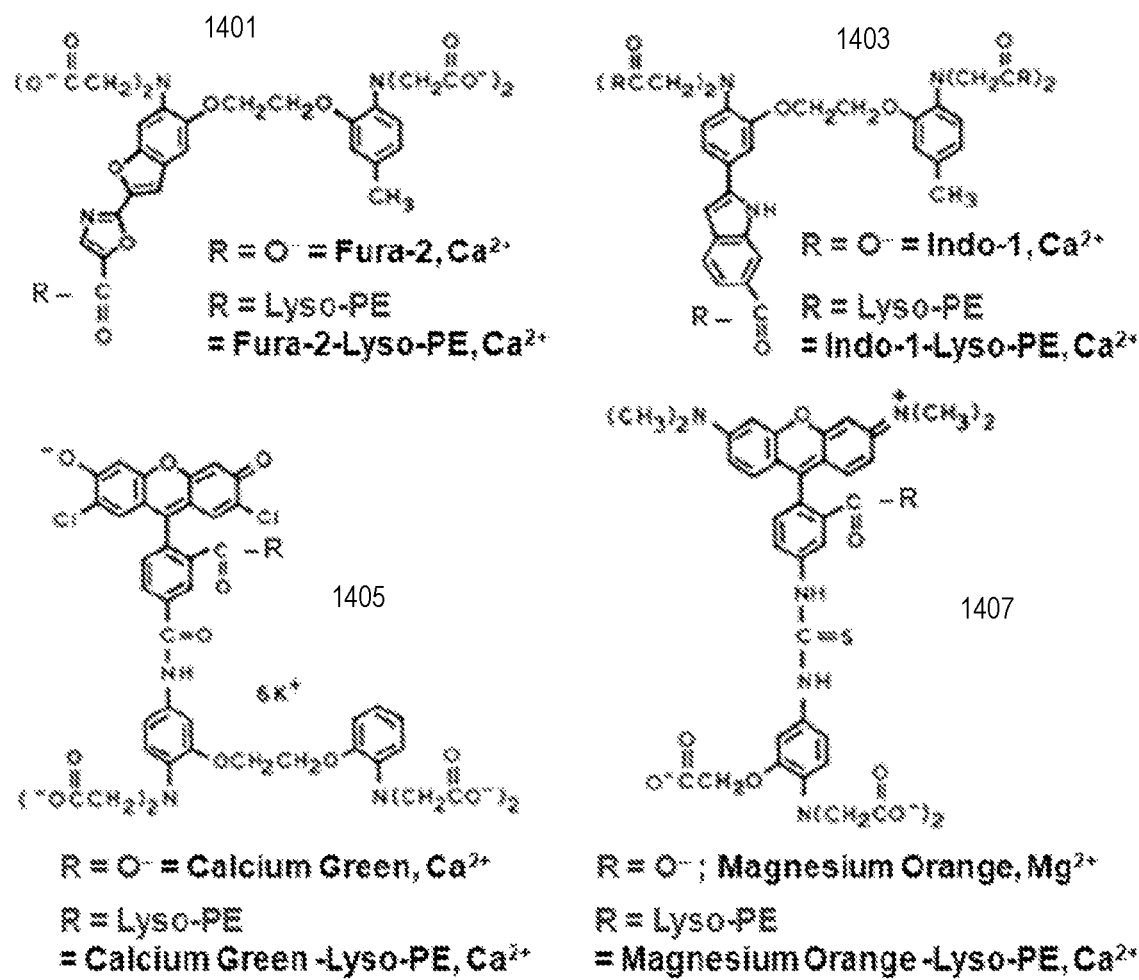
FIG. 14 is a set of chemical diagrams that illustrate example structures of calcium and magnesium ion-detecting probe compositions and proposed lyso-PE derivatives for binding the probe composition into a contact lens, according to various embodiments.

FIG. 14 is a set of chemical diagrams that illustrate example structures of calcium and magnesium ion-detecting probe compositions and proposed lyso-PE derivatives for binding the probe composition into a contact lens, according to various embodiments. FIG. 14 shows four structures 1401, 1403, 1405, and 1407 for detecting these ions. Structures 1401, 1403, and 1405 detect calcium levels and structure 1407 detects $Mg^{2+}$. As with the probe composition embodiments above, lyso-PE is added to various probes in the location corresponding to the R group in FIG. 14. It should be noted that structure 1401 may also be modified by adding an 8-18 alkyl side chain in place of the lyso-PE.

Figure 15A:
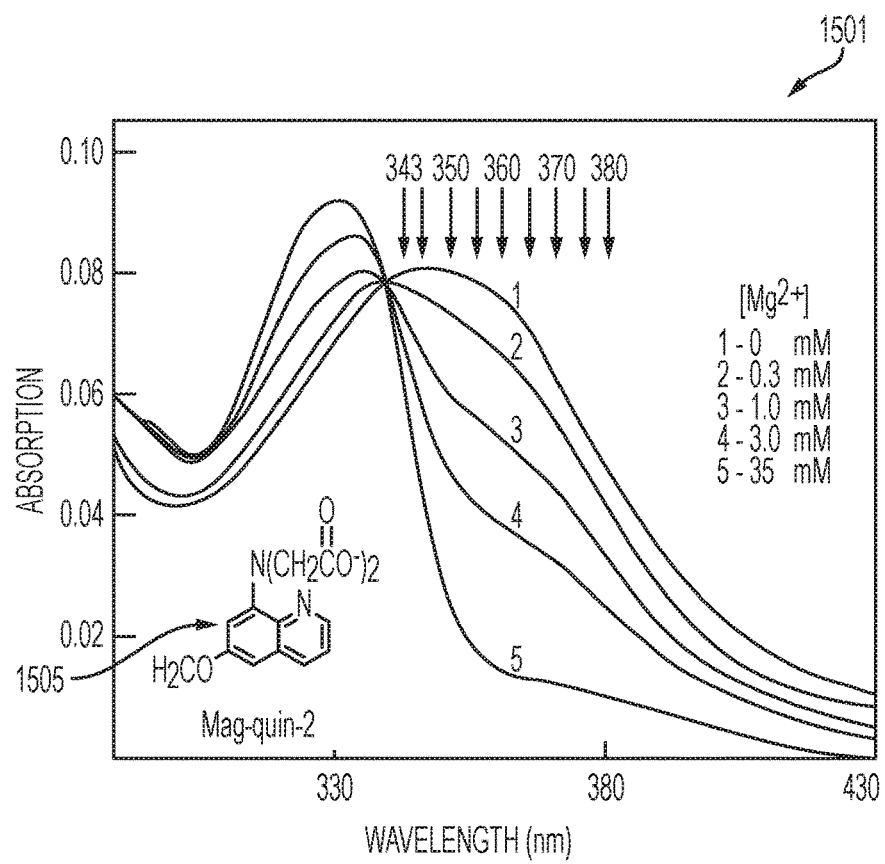
FIG. 15A and FIG. 15B are graphs that illustrate example absorption and emission response, respectively, to magnesium as well as a structure for a magnesium-detecting probe composition, according to an embodiment.
Figure 15B:
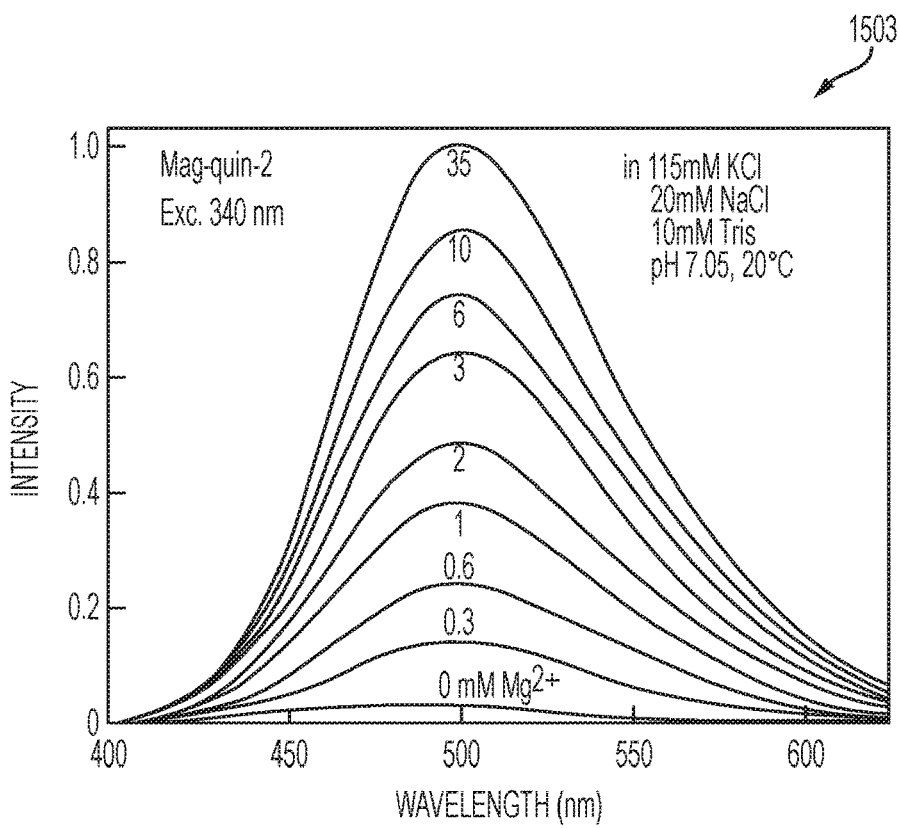

FIG. 15A and FIG. 15B are graphs that illustrate example absorption and emission response, respectively, to magnesium as well as a structure for a magnesium-detecting probe composition, according to an embodiment. FIG. 15A includes an inset that shows another embodiment of a probe Mag-quin-2 1505 for detecting $Mg^{2+}$. This probe may be modified by adding a hydrophobic side chain (such as an alkyl group having between 8-18 carbons) or lyso-PE group so that it is capable of binding at a silicone-water interface. The absorption spectra 1501 and emission spectra 1503 show that a modified version of Mag-quin-2 can be used as an excitation wavelength ratiometric probe for the same reason as other probes compositions disclosed. Another advantage is that the binding constant can be changed from 0.2 mM to 20 mM by changing the excitation wavelength from 340 to 365 nm. This effect is valuable in making a magnesium sensitive contact lens; if the binding at the silicone-hydrogel interface changes the magnesium affinity outside the physiological range, the apparent binding constant can be shifted to the most magnesium sensitive range by using LEDs with different wavelengths.

2.5 Example—Detecting Probe Compositions

It is important to be able to determine chloride ion concentrations in tears as these concentrations are needed to calculate the total osmolarity of a patient's tears. Detection of the chloride ion by a typical probe occurs by the process of collisional quenching. Collisional quenching is discussed in reference to FIG. 22 below, but essentially means a probe in the excited state returns immediately to the ground state without emitting a photon, upon contact with chloride ion due to diffusion. The probe is not destroyed by the quenching process and remains available for further excitation.

Figure 16:
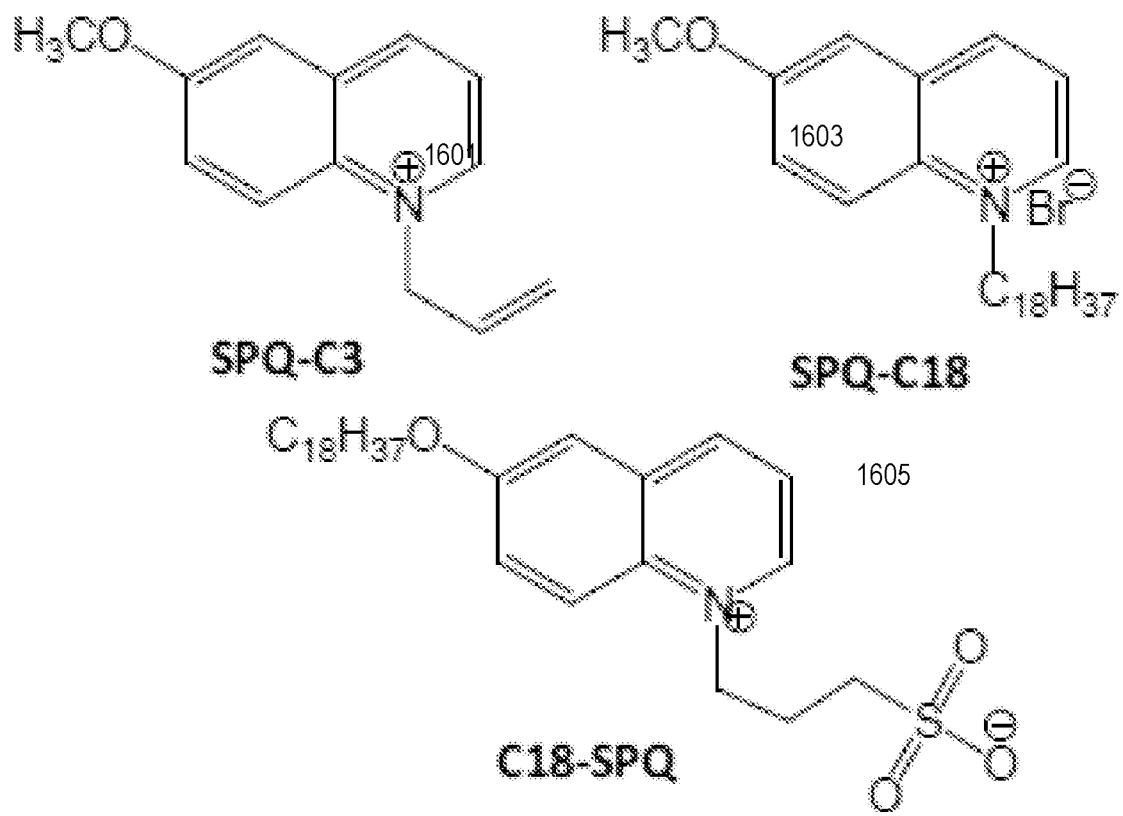
FIG. 16 is a chemical diagram that illustrates example probe composition structures for detecting chloride ions, according to an embodiment.
Figure 17A:
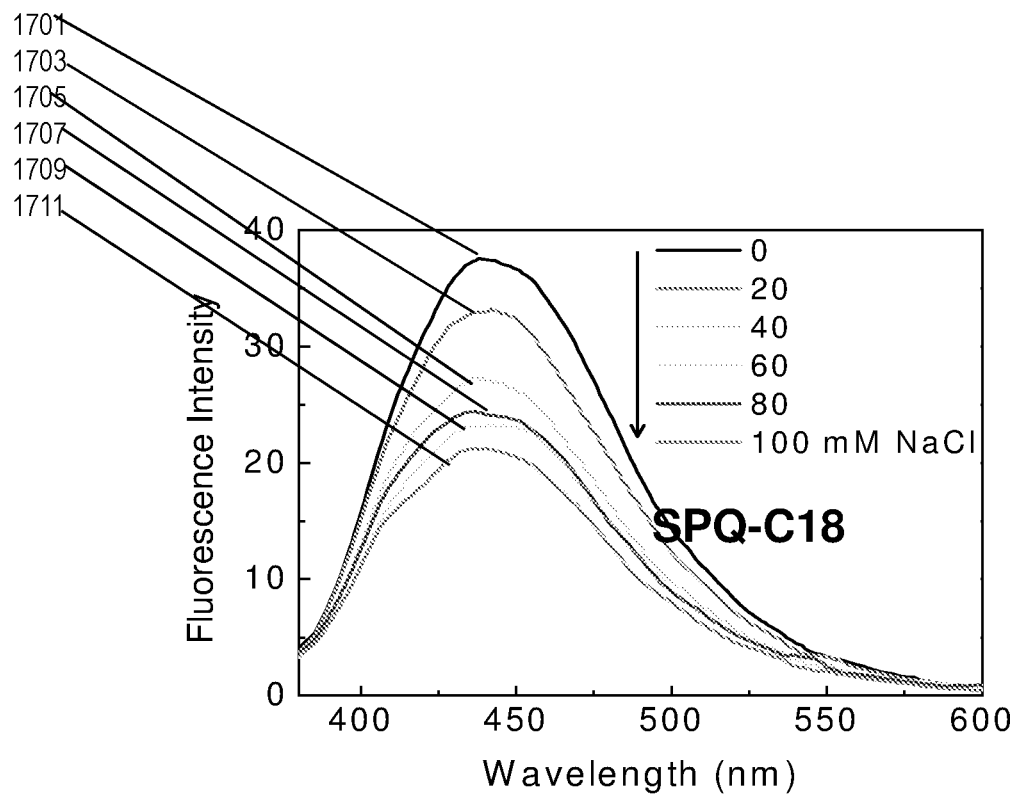
FIG. 17A is a graph that illustrates an example emission spectra for SPQ-18 in an Stenfilcon (Aspire™) contact lens, according to an embodiment.

Previously known reported chloride probes would not work as components in probe compositions for use in a SiHG-CL. FIGS. 16 and 17A demonstrate various chloride probes and their various properties. FIG. 16 is a chemical diagram that illustrates example probe composition structures for detecting chloride ion, according to an embodiment. In FIG. 16, probe SPQ-3 1601 is too sensitive to chloride ions because it is almost completely quenched at concentrations that are lower than the typical eye concentration of chloride ion. This is a problem because it would not be possible to get an accurate read of actual chloride ionconcentrations in tears in this situation. To develop a chloride ion probe that would be less sensitive to quenching, it was recognized that the addition of a carbon side chain (preferably 8-18 carbons in length), as in probe composition embodiment 1603 (SPQ-C18) would reduce the quenching sensitivity of the probe to chloride ions.

Figure 18:
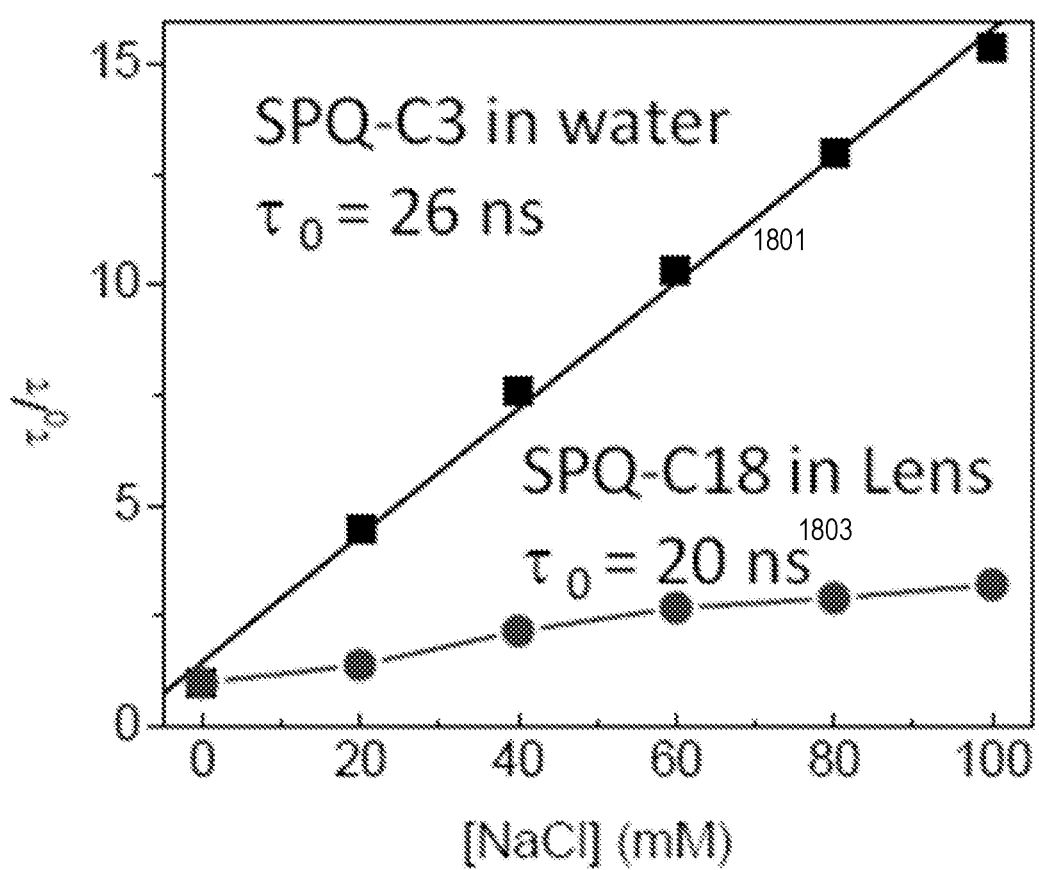
FIG. 18 is a graph that illustrates an example comparison of lifetime Stern-Volmer traces for SPQ-C3 in water and SPQ-C18 in a Stenfilcon (Aspire™) contact lens, according to an embodiment.

When tested, SPQ-C18 1603 exhibited a 7-fold reduction in quenching sensitivity when bound to a SiHG-CL. FIG. 17A is a graph that illustrates an example emission spectra for SPQ-18 in an Stenfilcon (Aspire™) contact lens, according to an embodiment. As shown in FIG. 17A, the fluorescence intensity at various concentrations of chloride ion (from NaCl salt ranging from 0-100 mM) ranged from around 20-40% at 450 nm (see traces 1711 and 1701, respectively). In contrast, the fluorescence intensity SPQ-C3 ranged from around 20-100% at 450 nm for concentrations ranging from 0 to 100 mM (not shown). This is a problem because the normal chloride ion concentration in tears is about 118-138 mM. Therefore, unlike SPQ-C31601, SPQ-C18 1603 is only about 50% quenched at typical chloride ionconcentration in tears, leaving remaining ability to detect if there are abnormally elevated chloride ion concentrations in an eye. This reduction in quenching renders the disclosed probe composition suitable for its intended purpose, and is also demonstrated by the comparison of lifetime Stern-Volmer plots for SPQ-C3 v. SPQ-C18 in FIG. 18. FIG. 18 is a graph that illustrates an example comparison of lifetime Stern-Volmer traces for SPQ-C3 in water and SPQ-C18 in a Stenfilcon (Aspire™) contact lens, according to an embodiment.

Figure 17B:
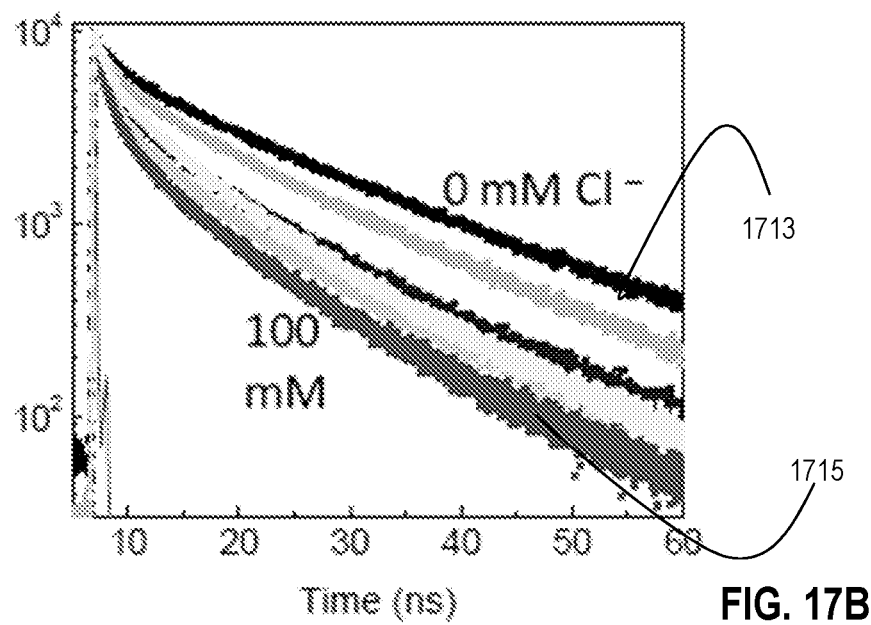
FIG. 17B is a graph that illustrates an example time-dependent decay of SPQ-18 in the presence of the chloride ion, according to an embodiment.

It should be noted that these measurements were taken with the probes in a Stenfilcon A(Aspire™) contact lens, a typical SiHG-CL. FIG. 17B is a graph that illustrates an example time-dependent decay of SPQ-18 (1603) in the presence of the chloride ion, according to an embodiment. FIG. 17B is included to show that this spectral property of this probe composition embodiment 1603 is also useful for correlation with various concentrations of chloride ions. For instance, 0 mM chloride ion (trace 1713) is distinct from trace 1715 which was taken at 100 mM concentration.

In addition, probe composition embodiment C18-SPQ 1605 has an additional water soluble sulfonic acid group, which allows for more chloride ion sensitivity, since this portion of the probe composition would orient in the aqueous nanochannels where chloride ion would be present.

Recent developments in silicone hydrogel contact lens (SiHG-CL) and fluorescent probes also provide an opportunity to perform measurements of biomarker concentrations with specially labeled (probe composition-infused) contact lenses for detection of keratitis. Keratitis is an eye infection associated with wearing contact lenses. Over the past 40 years there have been many changes in the composition of contact lenses, from glass, to PMMA, to HEMA polymers, SiHG and SiHG with increased oxygen transport. Even with all these changes, the incidence of contact lens-induced keratitis has remained constant. This result suggests that keratitis originates with chemical changes occurring in the tear layer surface between the inner surface of the contact lens and the outer layers of the cornea. There are no typical ways to perform measurements in this region which has a volume much smaller than the tear volume of an eye, and is inaccessible to any type of sample collection without disturbing the sample itself.

The water channels in the nanoporous polymer networks (NPN) of the hydrogel are probably too small for penetration of large proteins such as lysozymes, bacteroferrin and IgA. However, the water channels may be large enough to admit smaller molecules such as defensins, which are typically small peptides with 29 to 42 amino acids and are constrained into folded forms by six conserved cysteine residues. Human beta-defensin-2 [HBD-2] is produced rapidly following stimulation of epithelial cells and increased concentrations of HBD-2 is often the earliest sign of infections, even before the infection is visible to an ophthalmologist. The strong resistance of corneal epithelial to infection is most likely due to HBD-2 which is rapidly produced in response to some bacteria (e.g., P. aeruginosa) and specific lipopolysaccharides. Defensins could be detected by aptamers or peptide aptamers which are much smaller than antibodies and could be incorporated into a SiHG-CL, either in the NPN or on the lens surface.

3. Example Glucose Embodiments in Contact Lens

Recent developments in silicone hydrogel contact lens (SiHG-CL) and fluorescent probes provide an opportunity to perform measurements of glucose concentrations with specially labeled (probe composition-infused) contact lenses for detection of diabetic hyperglycemia for disease control and diabetic hypoglycemia due to overdose of insulin.

Figure 19:
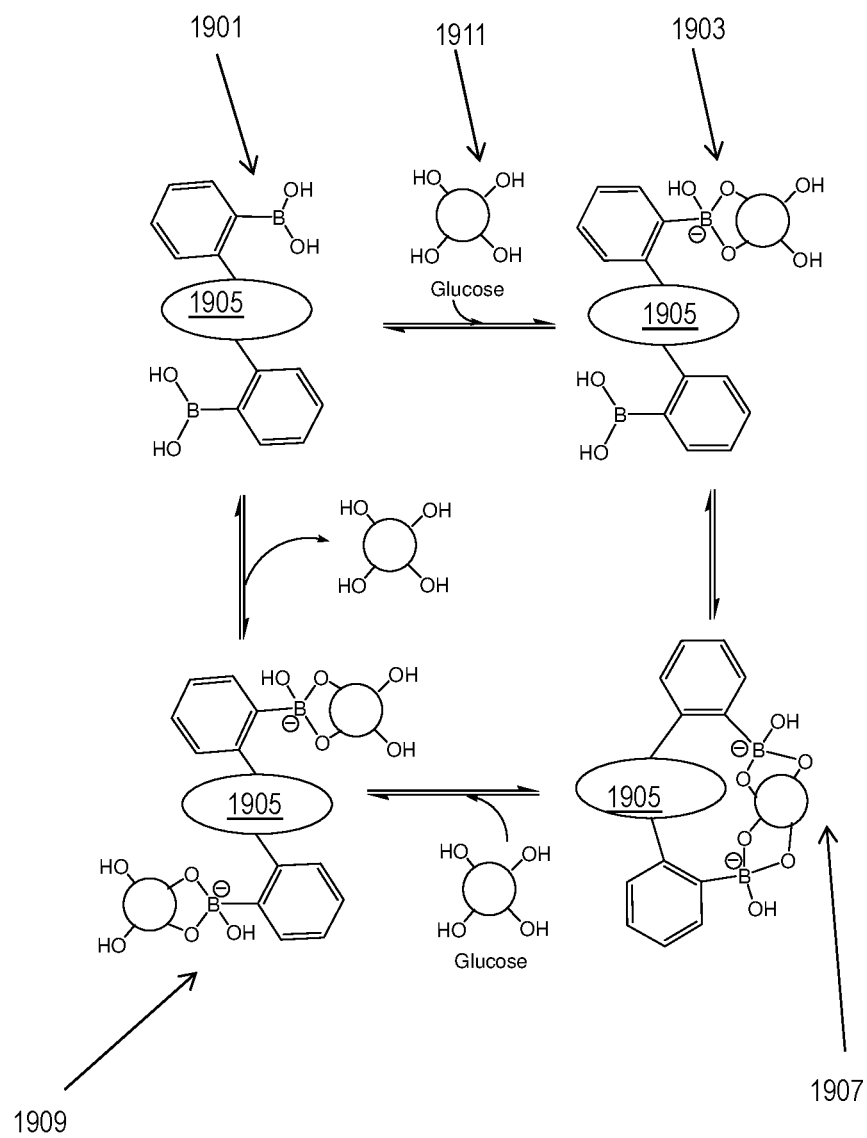
FIG. 19 is a chemical diagram that illustrates an example generic diboronic acid molecule in the sugar-bound and sugar-unbound conformations, according to an embodiment.

As mentioned previously in this disclosure, Glu-SFs are based on molecules containing boronic acid in which boronic acids binds reversibly to glucose. FIG. 19 is a chemical diagram that illustrates an example generic molecule containing diboronic acid moieties in the sugar-bound and sugar-unbound conformations, according to an embodiment. FIG. 19 shows a generic molecule containing two boronic acid moieties 1901. FIG. 19 is included to show the boronic acid conformation in a sugar-bound state 1903, 1905, 1909 versus a sugar-unbound state 1901. (The term "sugar" in this figure may represent a molecule of glucose).

This generic composition is the probe composition 150 in some embodiments, in which case, the R group 1905 is a combination of the fluorophore portion 154a and/or 154b, together with the spacer portion 156 (if appropriate), the hydrophobic portion 151, and the hydrophilic portion 152. In that case, the boronic acid moieties 1901, 1903 would be the analyte binding portion 153.

In this example, the analyte to be bound is glucose. As is shown in FIG. 19, boronic acid moiety 1901 is in the trigonal (sugar-unbound) form. Boronic acid moiety 1903 is in the tetrahedral conformation when in the sugar-bound form. These structures can change confirmation between structure 1907 (the sugar bound to both boronic acid moieties, or structure 1909 with the addition of another glucose, two molecules of glucose can be bound—one for each boronic acid.

Glucose binding changes the electron donating-accepting (Lewis base-acid) ability of boronic acid which in turn affects the adjacent fluorophore portion 1905. This binding of glucose to the boronic acid moieties of any of the embodiments disclosed herein alters the fluorescence spectra, intensity or lifetimes of nearby fluorophores by different mechanisms These fluorescence features can be correlated to the glucose levels in a sample of interest.

Figure 20:
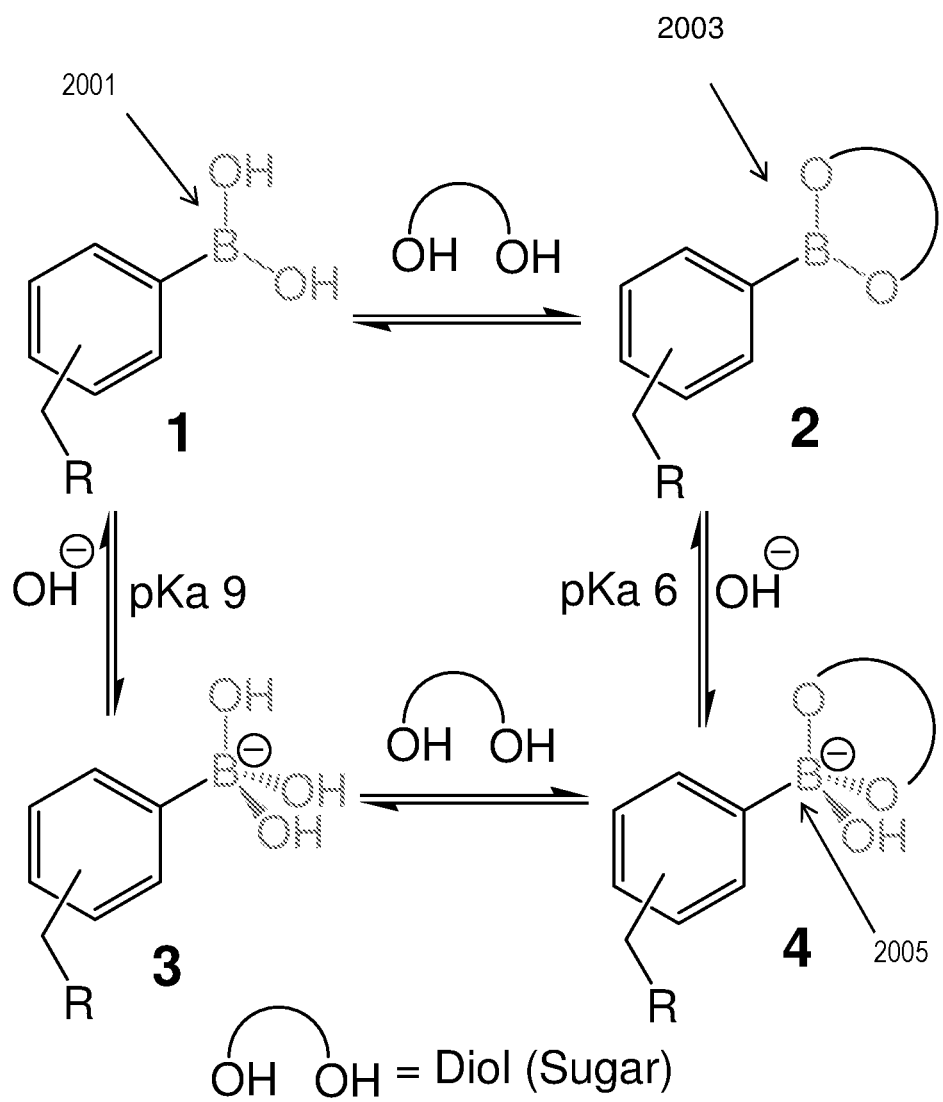
FIG. 20 is a chemical diagram that illustrates a more detailed example reaction scheme showing the binding of boronic acids to sugars, showing different forms of the various boronic acid moieties, according to an embodiment.

Glu-SFs typically have one or more boronic acid moiety which binds to glucose (although one is shown in FIG. 20 for illustrative purposes, probe compositions have been prepared with more than one boronic acid moiety). When binding occurs, the trigonal geometry of the boron changes to a tetrahedral geometry with more electron density on the boronic acid moiety.

Figure 22:
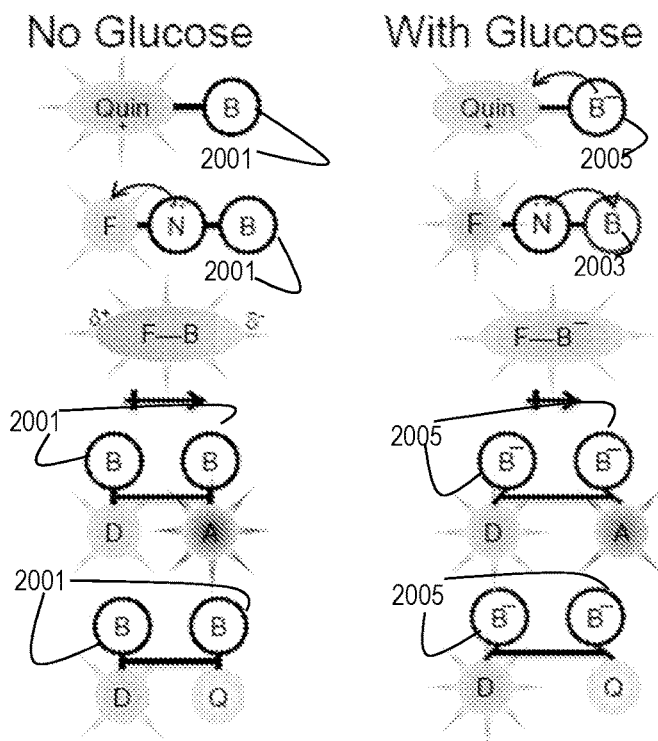
FIG. 22 is a set of diagrams that illustrate various example mechanisms by which changes in geometry of a boronic acid moiety can affect the spectra, intensity, or lifetimes of nearby fluorophores.

This change in geometry and/or electron density can affect the spectra, intensity or lifetimes of nearby fluorophores by different mechanisms, which are summarized in FIG. 22. Note that FIG. 20 shows a boronic acid structure, but embodiments of probe compositions 150 herein employ a diboronic acid. Depending on the fluorophore portion used in the probe composition, one or more of these properties (spectra, intensity or lifetimes) is affected. For example, collisional quenching processes may result in changes in intensity without significant effects to the emission spectrum. Intensity measurements are useful and simple for relating a concentration of an analyte to the intensity of fluorescence, however, generally speaking, shifts in wavelength of spectral peak is a preferable property to measure over intensity. While intensity measurements are simple and straightforward, they may be inadequate at times in real world situations due to for example, the turbidly of a sample, non optical surfaces may be misaligned, dependence on measurement geometry, and, generally, intensity-based sensing is not particularly sensitive to small changes in intensity. Finally, lifetime-based sensing measures changes in lifetime of fluorophores in response to analytes, and is advantageous in that fewer probes display spectral shifts, but a wide variety of quenchers and/or molecular interactions result in changes in the lifetimes of fluorophores.

One of the objectives was to design probe compositions which can be used to detect various analyte concentrations, but using these various types of properties and through different mechanisms of electron density affects.

FIG. 22 is a set of diagrams that illustrate various example mechanisms by which changes in geometry of a boronic acid moiety can affect the spectra, intensity, or lifetimes of nearby fluorophores FIG. 22 shows five different mechanisms by which the various probe compositions disclosed display their given spectral properties to be detected (thereby correlating to a given analyte concentration). These photophysical mechanisms include quenching (e.g., FRET or collisional quenching), photo-induced electron transfer (PET), and intramolecular charge transfer (ICT) which can result in changes in lifetime and spectral shifts due to the different electronic distributions when bound to glucose. In the SiHG-CL, these photophysical processes will occur at the water-silicone interface within the SiHG-CL, and require different amounts of molecular motion.

It should be noted here that the various encircled B symbols in FIG. 22 are the various forms of the boronic acid shown in the preceding FIG. 20. Also, it should be noted FIG. 20 shows a boronic acid structure for the purpose of showing the binding of boronic acids to sugars and to show different forms of the various boronic acid moieties can take. However, embodiments of probe compositions 150 herein employ a diboronic acid, for example a diboronic acid shown in FIG. 19. Therefore, reference to FIG. 20 and FIG. 22 together is appropriate. Below is a summary of the various mechanisms through which probe compositions 150 described herein operate.

Turning to the first mechanism represented in FIGS. 20 and 22, Quinoline mechanism 2201 occurs with certain quinolinium based probe compositions and simply refers to the electron donor-acceptor interactions that take place in quinolinium based probe compositions disclosed when glucose binds to the boronic acid moiety. The boronic acid in this type of probe composition is in the form 2001 in the unbound form. When bound to glucose, the boronic acid moiety acquires the additional hydroxyl group and takes the form 2005. The electron movement in this mechanism proceeds by a shift in charge density from the bound form of boronic acid moiety 2005 moving to the quinolinium structure. Note that FIG. 22 refers to Mechanism 1 as "Quinoline," however, this shall be understood to mean the mechanism for "quinolinium" based probe compositions disclosed below.

The second mechanism, shown in FIGS. 20 and 22, 2203 is photoinduced electron transfer (PET). PET is an excited state electron transfer process by which excited electron is transferred from donor to acceptor. In the example 2203, the electron donor is the amino group, represented as the encircled "N." Upon the binding of glucose, the diagram shows the electrons are taken from the nitrogen and that the boronic acid moiety takes the conformation 2003. Some Glu-SFs display intensity changes due to PET quenching. These Glu-SFs typically contain an aromatic fluorophore with a nearby amino group. Specific examples of probe compositions which work via this mechanism are given following this discussion on mechanisms generally. The amino group transfers an electron to the excited state fluorophore resulting in quenching because the exciplex is usually non-fluorescent. However, quenching is not a necessary consequence of PET. Electron transfer can result in formation of an excited state complex called an exciplex. An exciplex can display strong emission in non-polar solvents. Exciplex emission may occur in some SiHGs, but to a much lesser extent (or not at all) in HG lenses.

Still referring to FIGS. 20 and 22, mechanism 3, intramolecular charge transfer (ICT) 2205 refers to a molecule having intramolecular electron transfer which occurs in a push-pull electronic structure of the excited state, resulting in positive and negative charge separation process in the molecule. Generally, ICT-based probe molecules typically include an electron donative group (hydroxyl group, amino group, etc.), and an electron withdrawing group (aldehyde group, benzothiazole, etc.) connected together. In the example shown, the "no Glucose" form of the probe composition has a longer dipole moment than the bound form. As provided in further detail below, a probe composition has been designed which will cause the overall charge distribution of the fluorophore portion to change upon the binding of glucose.

Mechanisms 2207 and 2209 in FIG. 22 refer to FRET and Collisional Quenching mechanisms, respectively. Both are quenching processes. "Quenching" refers to any process which decreases the fluorescence intensity of light emitting molecules. A variety of processes can result in quenching, such as excited state reactions, energy transfer, complex-formation and collisional or dynamic quenching. The chloride ion is a well known quencher for quinine fluorescence.

Typical fluorescence microscopy techniques rely upon the absorption by a fluorophore of light at one wavelength (excitation), followed by the subsequent emission of secondary fluorescence at a longer wavelength. FRET involves a donor fluorophore in an excited electronic state, which may transfer its excitation energy to a nearby acceptor. One advantage of FRET mechanism 2207 that is it is independent of immediate environment of the Donor (D) and Acceptor (A) pair.

Collisional quenching is similar to FRET and not dependent on the local chemical environment. In contrast to FRET, collisional quenching requires direct molecular contact between the fluorophore and quencher. Because of the short interaction distances, collisional quenching usually requires some diffusive motions to bring the molecules into contact.

FRET is due to a through-space interaction which occurs over distances from 1 to 10 nm. Molecular contact between the donor and acceptor is not necessary. FRET also depends on the absorption and emission spectra of the donor and acceptor. Mechanism 2209 shows that collisional quenching requires molecular contact of the probe with the quencher, at distances less than 0.5 nm. FRET requires an acceptor which absorbs at the donor emission wavelength. A quencher does not need to have absorption which overlaps the probe, and typically does not have such absorption.

3.1 Development of Polarity-Sensitive Probes

One issue in the development of the disclosed probe compositions is that they are designed to most frequently reside in the water-silicone boundary. If the probe composition were too soluble in water, it would wash out of the lens and not work for extended analyte monitoring. At the same time, the probe composition should not have so much nonpolar character that it was highly soluble in the silicone-based interstices of the contact lens material. Unless the probe composition resides at the water-silicone boundary, it would not both come into contact with the aqueous analytes and persist in place as the aqueous solution flows by.

Figure 21A:
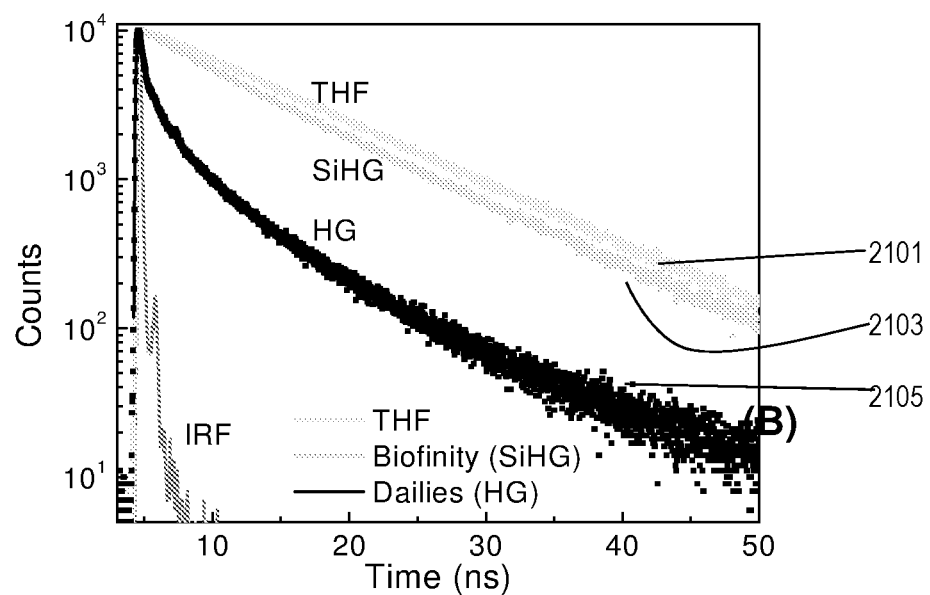
FIG. 21A and FIG. 21B are graphs that illustrate example intensity decays and anisotropy decays in THF and Biofinity™ contact lens, respectively, according to an embodiment.
Figure 21B:
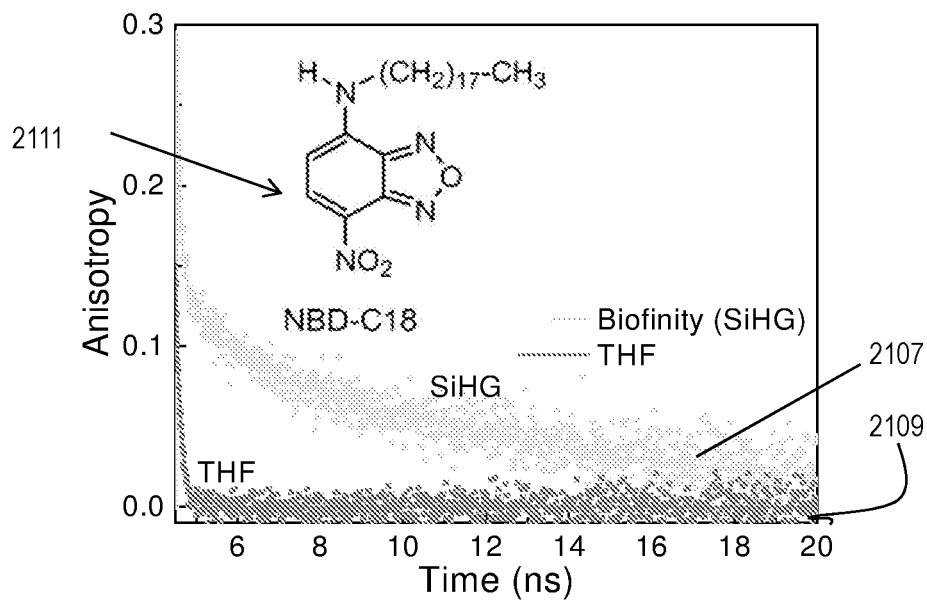

FIG. 21A and FIG. 21B are graphs that illustrate example intensity decays and anisotropy decays in THF and Biofinity™ lens, respectively, according to an embodiment. In this embodiment, Biofinity™ SiHG lenses are used with a small water-soluble probe nitrobenz-oxa-diazole (NBD) linked to a C18 chain 2111. It is known that if fluorophores bind to the silicone-rich regions this will be detected by their long correlation times. In the Biofinity™ SiHG (2103) lens, this probe displayed a single long decay time consistent with a non-polar environment (nonpolar environment shown using THF 2101). In the non-silicone HG lens, the emission intensities were very weak (trace 2105) and the decays were strongly non-exponential which is believed due to weak and/or heterogeneous binding to the HG lenses. The anisotropy decay in the SiHG lens shown in FIG. 21 showed a correlation time near 6 ns, which is comparable to those found for fluorophores in cell membranes.

Consistent with the above data, it was also confirmed that NBD-C18 2111 was completely bound and would not wash out. This was shown by the absence of signal outside the lens indicating no detectable fluorophore present in the surrounding solution. For this reason, a single C18 side chain is adequate for complete binding of a Glu-SF to a SiHG lens.

3.2 Quinolinium Glu-SFs

Figure 23:
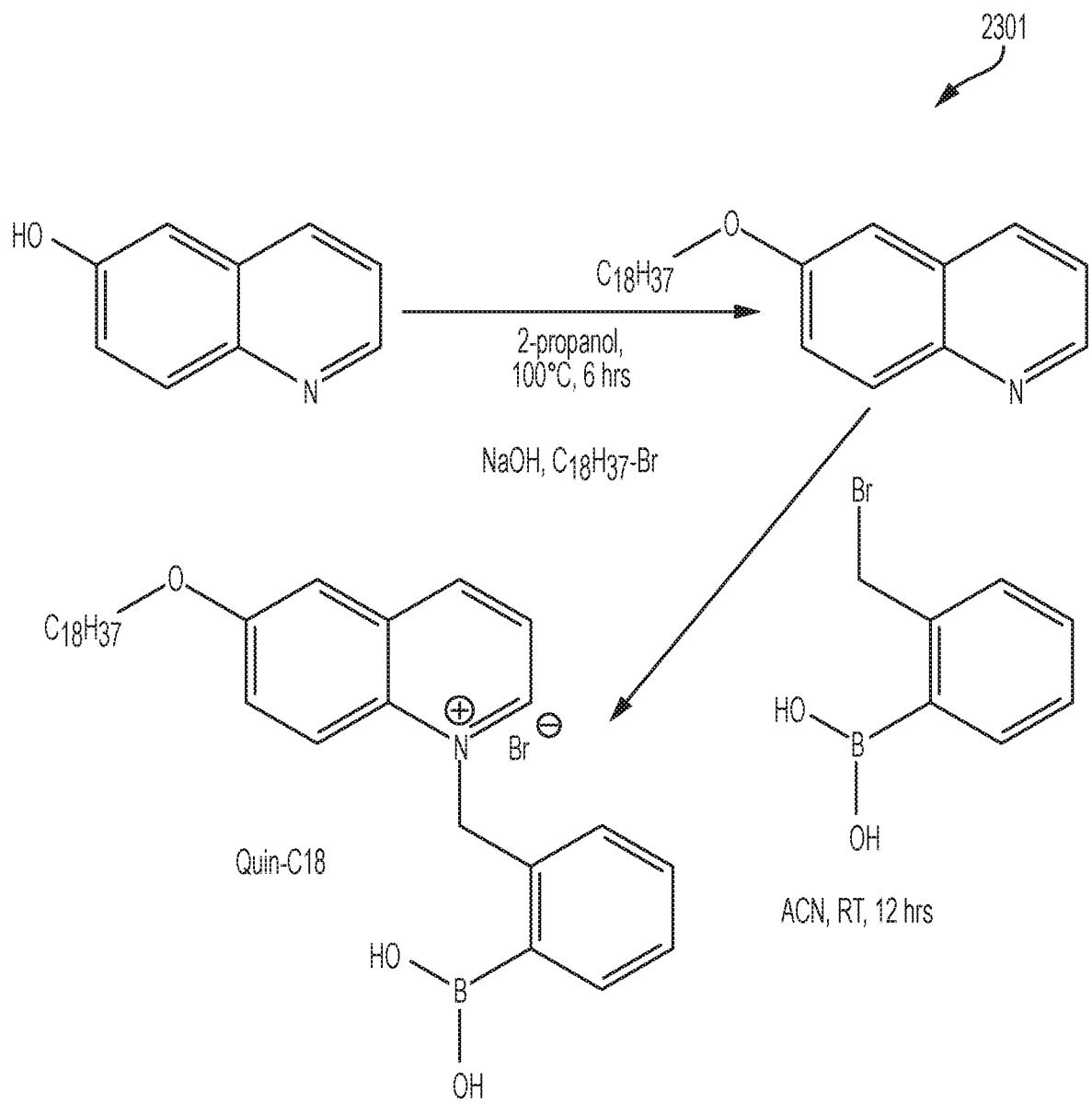
FIG. 23 is chemical diagram that illustrates an example reaction scheme for the preparation of probe composition Quin C-18, according to an embodiment.
Figure 25:
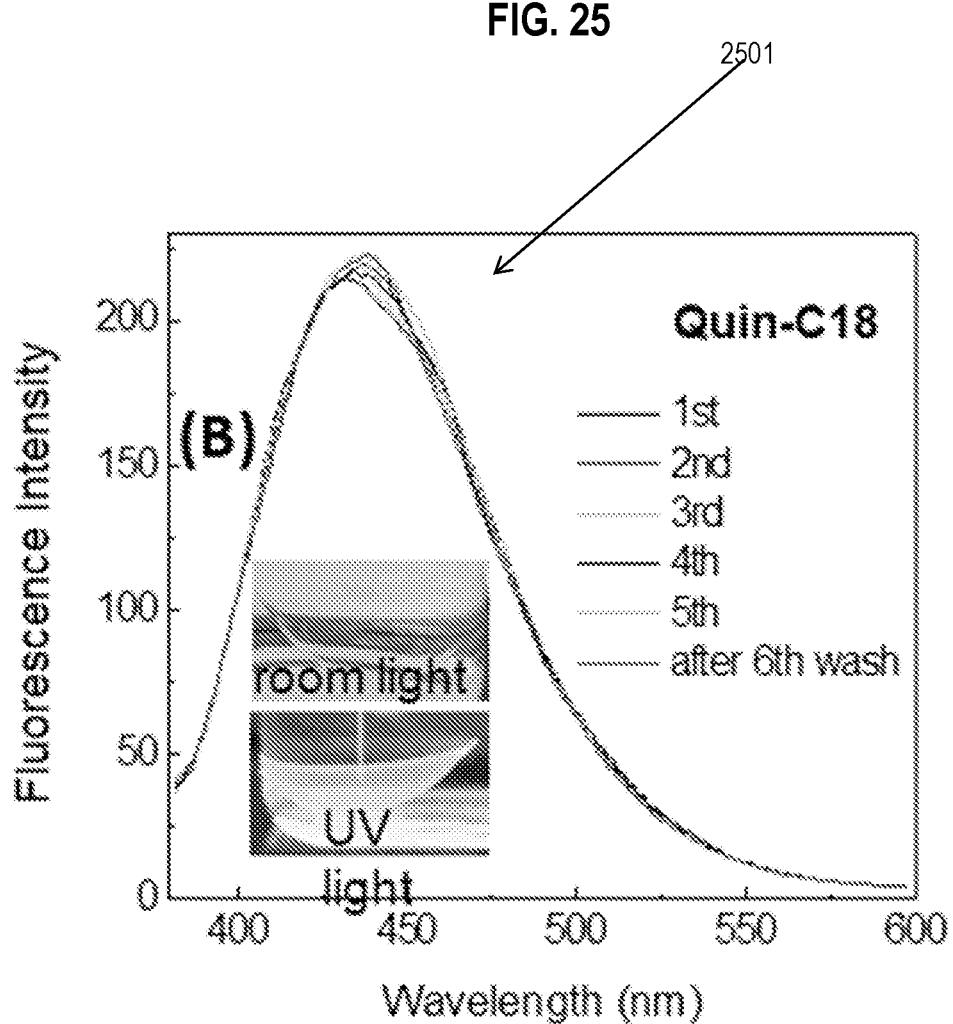
FIG. 25 is a graph with image inset that illustrates example persistence of fluorescent probe in SiHG contact lens after washing by showing the emission spectra of Quin-C-18 after repeated washing, and a photograph of the lens in room light and with UV incident light, according to an embodiment.

A standard quinolinium probe displays a useful spectra change in response to excitation with light, however it would not work for the intended purpose because it is too easily washed out of a contact lens. FIG. 23 is chemical diagram that illustrates an example reaction scheme for the preparation of probe composition Quin C-18 2301, according to an embodiment. Quin C-18 is hydroxyquinoline which has been modified to include a C18 alkyl side chain. In contrast to Quinoline alone, Quin-C18 could not be washed out of a SiHG lens even after repeated washings. FIG. 25 is a graph with image inset that illustrates example persistence of fluorescent probe in SiHG contact lens after washing by showing the emission spectra of Quin-C-18 after repeated washing, and a photograph of the lens in room light and with UV incident light, according to an embodiment. The repeated washings are shown in FIG. 25, which shows that the fluorescence intensity remained relatively unchanged even after 6 washes. The blue emission from Quin-C18 in the lens can be easily seen in room light with a UV hand lamp as the cloudy lens in the lower insert image of FIG. 25. Binding of Quin-C18 also did not change the visual appearance of the lens.

Figure 24A:
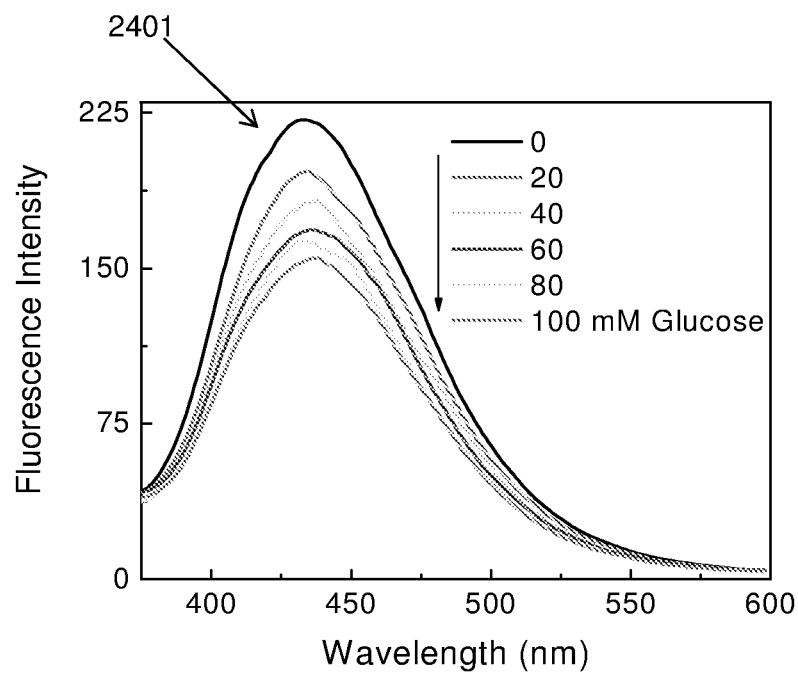
FIG. 24A is graph that illustrates an example glucose-dependent emission spectra of Quin-C18 within a Biofinity™ SiHG contact lens, according to an embodiment.
Figure 24B:
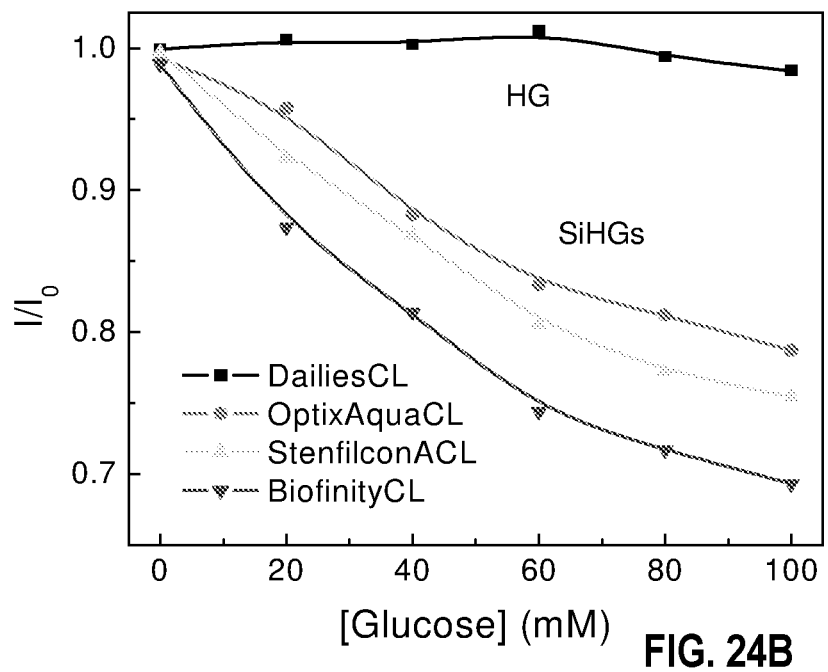
FIG. 24B is a graph that illustrates example normalized intensities in a Dailies (HG) lens and in three SiHG, Biofinity™, Stenfilcon A (Aspire™ 1 day) and Optix-Aqua™ lenses, according to an embodiment.

FIG. 24A is graph that illustrates an example glucose-dependent emission spectra of Quin-C18 within a Biofinity™ SiHG lens, according to an embodiment. FIG. 24B is a graph that illustrates example normalized intensities in a Dailies (HG) lens and in three SiHG, Biofinity™, Stenfilcon A (Aspire™ 1 day) and Optix-Aqua™ lenses, according to an embodiment. The Quin-C18 was tested in four types of CL polymers, 3 SiHG lenses, and 1 standard HG. Addition of glucose resulted in a decreased intensity for Quin-C18 in the 3 SiHG lenses, but the weak emission intensity was unchanged in the standard HG lens (FIG. 24B). This result proves that Glu-SFs can be designed to bind to the water-silicone interface and remain functional to glucose.

3.3 Photo-Induced Electron Transfer Glu-SFs

A known probe for detecting and binding glucose is called ANDBA, shown below.

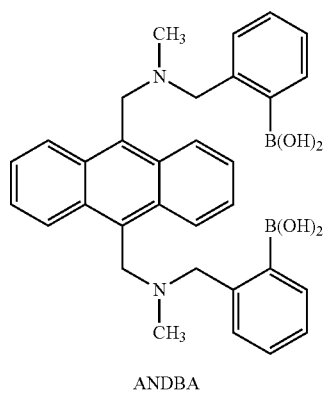

(A)

ANDBA

This probe has a strong response to glucose concentrations, but it was determined that these ANDBA probes did not respond to glucose in the HG or SiHG lenses.

Figure 26:
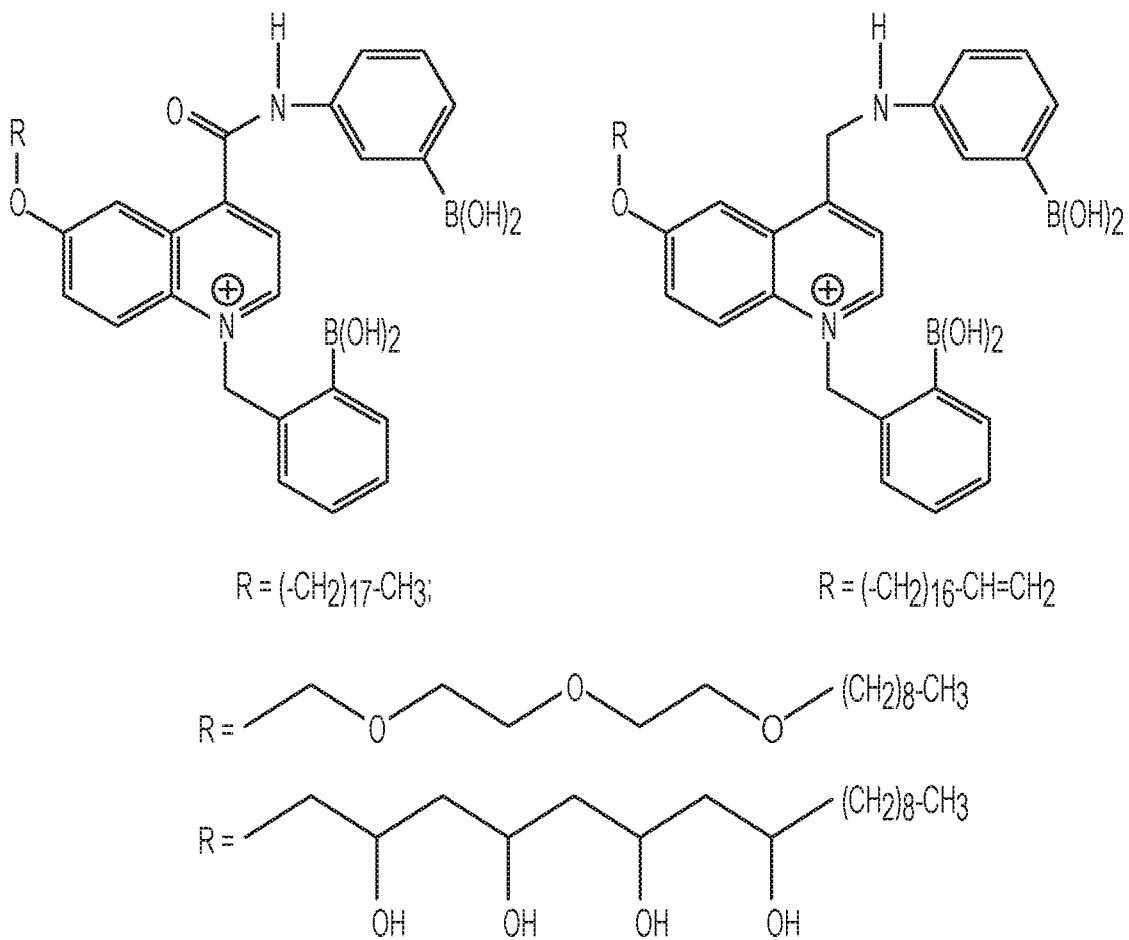
FIG. 26 is a chemical diagram that illustrates example diboronic acid Glu-SFs structures using a quinolinium nucleus for binding at an interface in SiHG contact lens, according to an embodiment.

To remedy this, ANDBA-like probe compositions are synthesized. The differences include that these ANDBA-like probe compositions include alkyl side chains which tend to orient the diboronic acid moiety towards the aqueous phase. These probe composition embodiments are shown (FIG. 26). FIG. 26 is a chemical diagram that illustrates example diboronic acid Glu-SFs structures using a quinolinium nucleus for binding at an interfaces in SiHG lenses, according to an embodiment. These side chains contain spacer portions of polyethylene glycol or hydroxyl groups.

Figure 27:
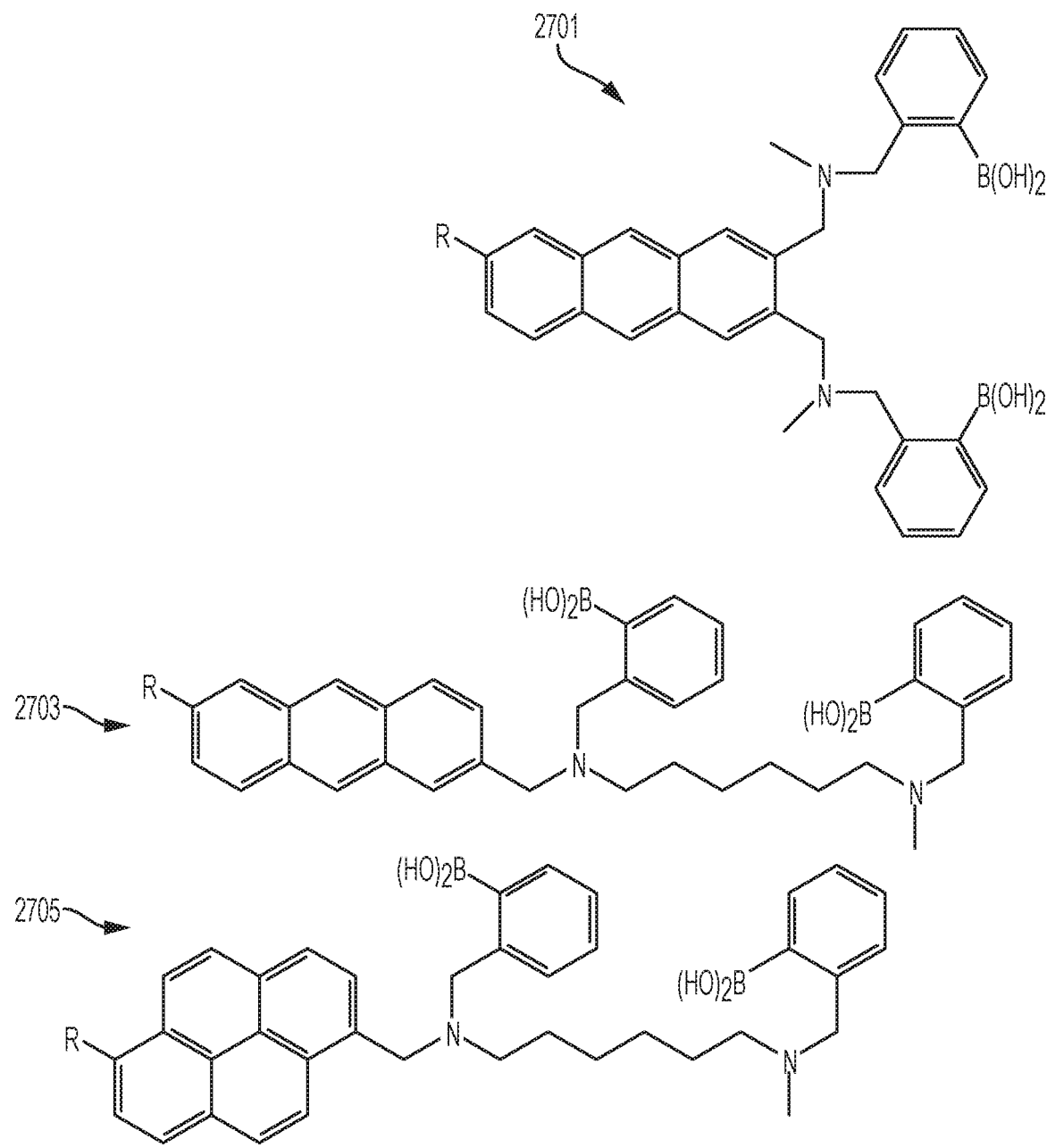
FIG. 27 is a chemical diagram that illustrates example diboronic acid PET Glu-SFs for binding at interfaces in SiHG lenses, in which the lower two structures are to displace the diboronic acid (DiBA) more into the water phase, according to an embodiment.

These embodiment probe compositions may also include further groups, such as polar or charged side chains. These side chains would also be added to ANDBA or the other PET probes of FIG. 26. Hydrophobic side chains with hydrophilic regions close to the anthracene are designed to expose the diboronic acid region more fully to the aqueous phase. The glucose response of ANDBA may have been restricted because the boronic acid groups are too far apart. FIG. 27 is a chemical diagram that illustrates example diboronic acid PET Glu-SFs for binding at an interfaces in SiHG lenses, in which the lower two structures are to displace the diBA more into the water phase, according to an embodiment. In this embodiment, the structure is modified so that the side chains are closer on the anthracene ring—depicted as structure 2701. Alternatively, the phenyl rings could contain polar or charged side chains to keep this region in the water phase. Positively charged side chains are likely to increase the glucose affinity because of the negative charges on the boronate groups when bound to glucose. The affinity for glucose can also be increased by electron withdrawing groups on the phenyl rings.

Additional structures for PET base probe compositions 2703 and 2705 are shown in FIG. 27. These probe compositions contain a six carbon chain linker but the fluorophores are still close to nitrogen to allow PET to occur. The C6 linker is known to provide the optimal distance between the boronic acid groups for high glucose specificity and affinity.

ANDBA did not display exciplex emission, which prevents its use as a wavelength-ratiometric probe. If exciplex emission is needed, or if PET quenching does not occur in the SiHG, the structure can be altered to contain moieties which increase the tendency for PET. For example, the rates of electron transfer can be increased by the addition of halogens (Cl or Br) to the electron-accepting fluorophore or by using carbazole as an electron donor. Numerous alternative structures such as fluorenes can be used to develop Glu-SFs for use in SiHG lenses.

In contrast to the Quin-based probes, the response of PET probes probably requires more flexing to move the phenyl side chains towards a central fluorophore. The desirable amount of probe motion is probably larger for the structures with a C6 linker (2703, 2705) than for the structure 2701. This suggests the probe response depends on the microviscosity at the water-silicone interface. If this interface is too viscous for the 7 ns decay time of anthracene, then a pyrene nucleus can be used which has a decay time near 200 ns and thus provides more time for the exciplex to form.

FIG. 27 shows diboronic acid PET Glu-SFs for binding at interfaces in SiHG lenses. The lower two structures are introduced to displace the diBA more into the water phase. R is a long alkyl chain which may be the R chains shown in FIG. 26 or similar.

FIG. 28 is a set of chemical diagrams that illustrate diboronic acid ICT Glu-SFs for binding at interfaces in SiHG lenses, according to an embodiment. R is a long alkyl chain which may be the R chains shown in FIG. 26 or similar. FIG. 29A shows Glu-SF structures using a diboronic acid on a C6 linker with FRET mechanism. R is a long alkyl chain which may be the R chains shown in FIG. 26 or similar.

3.4 ICT Probe Composition Embodiments

A number of Glu-SFs undergo intramolecular charge transfer (ICT) upon excitation. The extent of charge transfer depended upon glucose binding to the boronic acid, which changes its electron affinity. These probes were designed based on the known properties of diphenylpolyenes and the electronegativity of groups at each end of the molecule. These probes displayed large spectral peak wavelength shifts when bound to glucose in buffers. However, no such spectral shift was observed when the ICT probes were put into a conventional HG (not shown). For use in an SiHG-CL, these compounds are synthesized to include a hydrophobic side chain for use in an SiHG-CL. FIG. 28 shows diboronic acid ICT Glu-SFs for binding at interfaces in SiHG lenses which may be synthesized for this use. Glucose-dependent spectral shifts will occur because the overall charge of the probe changes upon binding glucose, so its position relative to the interface will change. If the emission spectrum is comparable to the spectrum in water, a more hydrophobic moiety on the nitrogen is added in some embodiments to shift its location towards the interface. Molecular flexing of the ICT probes is not needed for a glucose response. The immediate environment around the probe reorients in response to the new charge distribution of the probe.

3.4 Quenching Probe Composition Embodiments (FRET and Collisional Quenching Mechanisms)

FIG. 29 is a set of chemical diagrams that illustrate Glu-SF structures using a diboronic acid on a C6 linker with FRET mechanism, according to an embodiment and a Glu-SF structures using a diboronic acid on a C6 linker with a collisional quenching mechanism, according to an embodiment. FRET based Glu-SF is shown in FIG. 29 as structure 2901. The linkers may be six carbons long which is known to be optimal length for glucose selectivity and changes in FRET upon glucose binding have been demonstrated for this linker. The use of an aliphatic linker instead of an aromatic linker may also be employed and will allow the D-A distance to be modified for use in various SiHGs. In some embodiments, coumarins are used as donors and acceptors because they have two aromatic rings and contain various polar groups, which keeps the probes in the water-rich regions of the SiHGs. A large number of coumarins are available covering a wide range of wavelengths. At least two types of FRET probe compositions are suitable for this purpose in various embodiments. In one embodiment a Glu-SF with a fluorescent acceptor is used as a wavelength ratiometric probe with emission near 460 and 560 nm. In some embodiments, a Glu-SF with a non-fluorescent acceptor is used as a lifetime-based sensor using the donor emission (not shown). The donor lifetimes are a more reliable measurement of FRET than the intensity ratios. FRET is sensitive to background emission and other potential artifacts such as donors without an acceptor; or incomplete separation of the D and A emission spectra. The donor decay time measurement has the advantage of providing the most reliable measurement of the FRET efficiency.

For the FRET based Glu-SF, the donor and acceptor (D and A) are in close proximity so D-A pairs with small Ro values are an advantage. D-A pairs with Ro values, ranging from 6 to 33, using only a single donor are suitable The $R_o$ values can be decreased using acceptors with less spectral overlap. An additional opportunity provided by the use of coumarin probes is their high sensitivity to local polarity. The donor or acceptor emission may change in response to glucose binding due to relocation of the D or A, and thus provide a wavelength-ratiometric response. FIG. 29 at 2903 shows Glu-SF structures using a diboronic acid on a C6 linker with a collisional quenching mechanism. R is a long alkyl chain which may be the R chains shown in FIG. 26, or similar chains.

Figure 34:
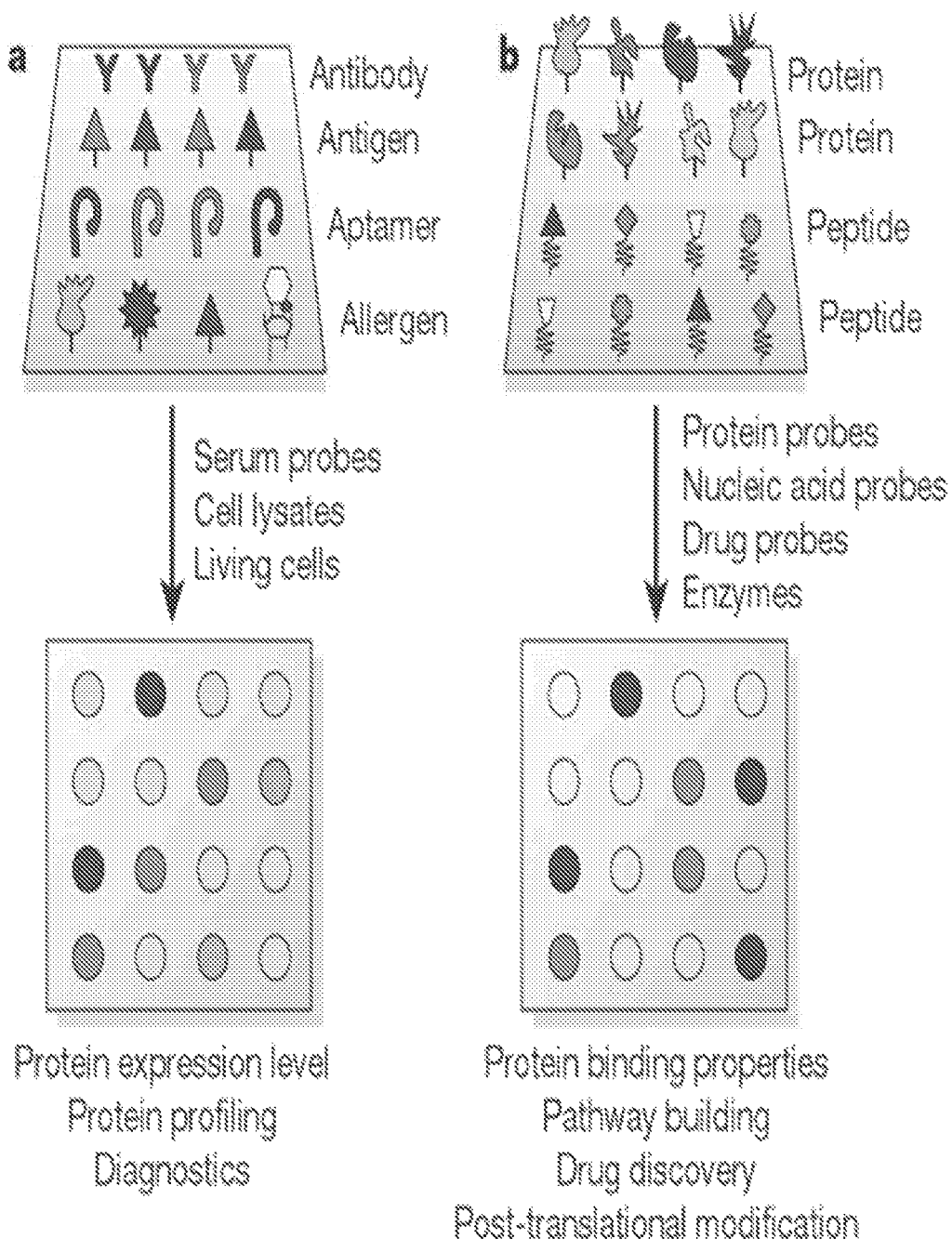
FIG. 34 is a diagram showing probes (which are embodiments of probe compositions herein) which may be used as shown for surface-based testing such as DNA and protein arrays, immunoassays, or other clinical assays, according to an embodiment.

Alternate pairs which may be used as donors and acceptors and which would be suitable for creating a probe composition based on FRET include the following pairs (Donor sub-portion listed first, followed by the acceptor sub-portion:

Naphthalene paired with Dansyl;
Dansyl paired with fluorescein-5-isothiocyanate (FITC);
Dansyl paired with octadecylrhodamine (ODR);
1-N6-ethenoadenosine (E-A) paired with NBD;
IAF paired with tetramethylrhodamin (TMR);
Pyrene paired with coumarin;
FITC paired with TMR;
5-(2-((iodocetyl)amino)ethyl)amino)naphthalene-1-sulfonic acid (IAEDANS) paired with FITC;
IAEDANS paired with 5-iodoacetamidofluorescein (IAF);
IAF paired an enzyme immunoassay (EIA) (See FIG. 34);
carboxyfluorescein, succinimidyl ester (CF) paired with Texas Red (TR);
4,4-difluoro-4-bora-3a,4a-diaza-s-indacene (Bodipy) paired with Bodipy;
B-phycoerythrin (BPE) paired with a cyanine dye (Cy);
Terbium paired with Rhodamine;
Europium paired with Cy; and
Europium paired with allophycocyanin (APC).

3.5 Fluorescence Measurement System

Figure 30:
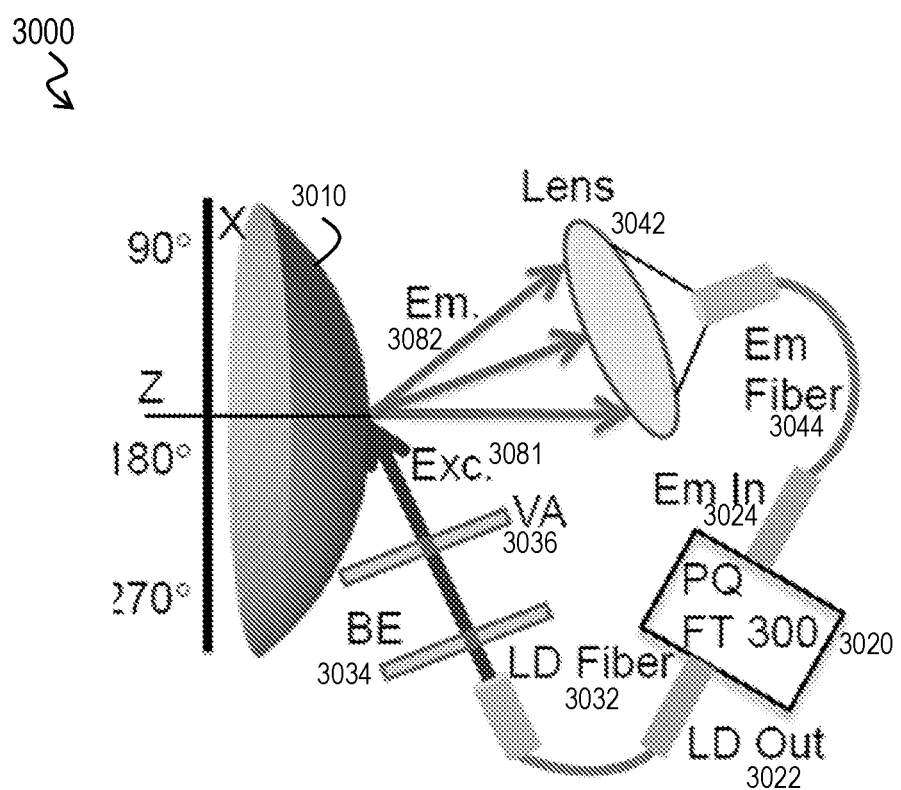
FIG. 30 is a block diagram that illustrates an example measurement system, according to an experimental embodiment.

FIG. 30 is a block diagram that illustrates an example measurement system 3000, according to an experimental embodiment. The system 3000 includes the probe material contact lens 3010 disposed on the cornea of a subject, with an axis of rotational symmetry defining the z direction, and the positive x direction at 90 degrees counterclockwise from the z axis. Tear fluid from the subject penetrates the contact lens 3010 and any analyte binds to the probe composition at the interface between the hydrogel channels and the silicone interstices.

An optical analyzer 3020, such as PicoQuant instrument (PQ FT 300 from PicoQuant Photonics International of West Springfield, Mass.) includes a pulsed laser diode (LD) that is energized to produce an laser diode (LD) source light that passes through LD output port 322 through optical fiber 3032 and optical couplers, such as beam expander (BE) and variable aperture (VA) 3036 to produce directional excitation light 3081 that impinges on the contact lens 3010. For example, the incident angle is selected to illuminate the contact lens 3010 at an angle to avoid direct incidence into the eye of the subject. The VA 3036 is used to illuminate part of the iris (1-2 mm diameter), the center outer surface of the pupil (1-2 mm), or the entire iris (about 10 mm) to obtain a maximal signal with minimal background.

The fluorescent emitted light, if any, emerges from the contact lens 3010 and is focused by an optical coupler, such as lens 3040, into the emission optical fiber 3044 where it is fed into the optical analyzer 3020 at optical input port 3024. The analyzer 3020 includes an LED source and control circuits, as well as an optical detector, analog to digital converter and Fourier analyzer. For example, the emission is collected with a 1 inch lens positioned about 1 inch from the eye, and focused into an optical fiber. The observation angle is close to perpendicular from the eye or slightly off the z axis. The emission is directed to the PicoQuant instrument for measurements of intensities, emission spectra or lifetimes. One can use light reflected or scattered from the eye as the timing reference for the lifetime analysis.

A digital input port (not shown) provides a digital signal from a separate processing system 380, such as a processor in a computer system 3100, chip set 3200 or mobile terminal 3300, or some combination, to control those components. A digital output port (not shown) outputs a digital signal carrying data that indicates the power fed into the LED and the spectrum of the received light. That output signal is received at the separate processing system 380 such as a processor in a computer system 3100, chip set 3200 or mobile terminal 3300, or some combination. At the processing system, the digital signal is used to determine the concentration of analyte in the tear fluid of the subject using a calibration curve appropriate for the probe material and detection method, as described above.

4. Computational Hardware Overview

FIG. 31 is a block diagram that illustrates a computer system 3100 upon which an embodiment of the invention may be implemented. Computer system 3100 includes a communication mechanism such as a bus 3110 for passing information between other internal and external components of the computer system 3100. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 3100, or a portion thereof, constitutes a means for performing one or more steps of one or more methods described herein.

A sequence of binary digits constitutes digital data that is used to represent a number or code for a character. A bus 3110 includes many parallel conductors of information so that information is transferred quickly among devices coupled to the bus 3110. One or more processors 3102 for processing information are coupled with the bus 3110. A processor 3102 performs a set of operations on information. The set of operations include bringing information in from the bus 3110 and placing information on the bus 3110. The set of operations also typically include comparing two or more units of information, shifting positions of units of information, and combining two or more units of information, such as by addition or multiplication. A sequence of operations to be executed by the processor 3102 constitutes computer instructions.

Computer system 3100 also includes a memory 3104 coupled to bus 3110. The memory 3104, such as a random access memory (RAM) or other dynamic storage device, stores information including computer instructions. Dynamic memory allows information stored therein to be changed by the computer system 3100. RAM allows a unit of information stored at a location called a memory address to be stored and retrieved independently of information at neighboring addresses. The memory 3104 is also used by the processor 3102 to store temporary values during execution of computer instructions. The computer system 3100 also includes a read only memory (ROM) 3106 or other static storage device coupled to the bus 3110 for storing static information, including instructions, that is not changed by the computer system 3100. Also coupled to bus 3110 is a non-volatile (persistent) storage device 3108, such as a magnetic disk or optical disk, for storing information, including instructions, that persists even when the computer system 3100 is turned off or otherwise loses power.

Information, including instructions, is provided to the bus 3110 for use by the processor from an external input device 3112, such as a keyboard containing alphanumeric keys operated by a human user, or a sensor. A sensor detects conditions in its vicinity and transforms those detections into signals compatible with the signals used to represent information in computer system 3100. Other external devices coupled to bus 3110, used primarily for interacting with humans, include a display device 3114, such as a cathode ray tube (CRT) or a liquid crystal display (LCD), for presenting images, and a pointing device 3116, such as a mouse or a trackball or cursor direction keys, for controlling a position of a small cursor image presented on the display 3114 and issuing commands associated with graphical elements presented on the display 3114.

In the illustrated embodiment, special purpose hardware, such as an application specific integrated circuit (IC) 3120, is coupled to bus 3110. The special purpose hardware is configured to perform operations not performed by processor 3102 quickly enough for special purposes. Examples of application specific ICs include graphics accelerator cards for generating images for display 3114, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 3100 also includes one or more instances of a communications interface 3170 coupled to bus 3110. Communication interface 3170 provides a two-way communication coupling to a variety of external devices that operate with their own processors, such as printers, scanners and external disks. In general the coupling is with a network link 3178 that is connected to a local network 3180 to which a variety of external devices with their own processors are connected. For example, communication interface 3170 may be a parallel port or a serial port or a universal serial bus (USB) port on a personal computer. In some embodiments, communications interface 3170 is an integrated services digital network (ISDN) card or a digital subscriber line (DSL) card or a telephone modem that provides an information communication connection to a corresponding type of telephone line. In some embodiments, a communication interface 3170 is a cable modem that converts signals on bus 3110 into signals for a communication connection over a coaxial cable or into optical signals for a communication connection over a fiber optic cable. As another example, communications interface 3170 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 3170 sends and receives electrical, acoustic or electromagnetic signals, including infrared and optical signals that carry information streams, such as digital data.

The term computer-readable medium is used herein to refer to any medium that participates in providing information to processor 3102, including instructions for execution. Such a medium may take many forms, including, but not limited to, non-volatile media, volatile media and transmission media. Non-volatile media include, for example, optical or magnetic disks, such as storage device 3108. Volatile media include, for example, dynamic memory 3104. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 3102, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 3102, except for carrier waves and other signals.

Logic encoded in one or more tangible media includes one or both of processor instructions on a computer-readable storage media and special purpose hardware, such as ASIC 313120.

Network link 3178 typically provides information communication through one or more networks to other devices that use or process the information. For example, network link 3178 may provide a connection through local network 3180 to a host computer 3182 or to equipment 3184 operated by an Internet Service Provider (ISP). ISP equipment 3184 in turn provides data communication services through the public, world-wide packet-switching communication network of networks now commonly referred to as the Internet 3190. A computer called a server 3192 connected to the Internet provides a service in response to information received over the Internet. For example, server 3192 provides information representing video data for presentation at display 3114.

The invention is related to the use of computer system 3100 for implementing the techniques described herein. According to one embodiment of the invention, those techniques are performed by computer system 3100 in response to processor 3102 executing one or more sequences of one or more instructions contained in memory 3104. Such instructions, also called software and program code, may be read into memory 3104 from another computer-readable medium such as storage device 3108. Execution of the sequences of instructions contained in memory 3104 causes processor 3102 to perform the method steps described herein. In alternative embodiments, hardware, such as application specific integrated circuit 3120, may be used in place of or in combination with software to implement the invention. Thus, embodiments of the invention are not limited to any specific combination of hardware and software.

The signals transmitted over network link 3178 and other networks through communications interface 3170, carry information to and from computer system 3100. Computer system 3100 can send and receive information, including program code, through the networks 3180, 3190 among others, through network link 3178 and communications interface 3170. In an example using the Internet 3190, a server 3192 transmits program code for a particular application, requested by a message sent from computer 3100, through Internet 3190, ISP equipment 3184, local network 3180 and communications interface 3170. The received code may be executed by processor 3102 as it is received, or may be stored in storage device 3108 or other non-volatile storage for later execution, or both. In this manner, computer system 3100 may obtain application program code in the form of a signal on a carrier wave.

Various forms of computer readable media may be involved in carrying one or more sequence of instructions or data or both to processor 3102 for execution. For example, instructions and data may initially be carried on a magnetic disk of a remote computer such as host 3182. The remote computer loads the instructions and data into its dynamic memory and sends the instructions and data over a telephone line using a modem. A modem local to the computer system 3100 receives the instructions and data on a telephone line and uses an infra-red transmitter to convert the instructions and data to a signal on an infra-red a carrier wave serving as the network link 3178. An infrared detector serving as communications interface 3170 receives the instructions and data carried in the infrared signal and places information representing the instructions and data onto bus 3110. Bus 3110 carries the information to memory 3104 from which processor 3102 retrieves and executes the instructions using some of the data sent with the instructions. The instructions and data received in memory 3104 may optionally be stored on storage device 3108, either before or after execution by the processor 3102.

FIG. 32 illustrates a chip set 3200 upon which an embodiment of the invention may be implemented. Chip set 3200 is programmed to perform one or more steps of a method described herein and includes, for instance, the processor and memory components described with respect to FIG. 3131 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 3200, or a portion thereof, constitutes a means for performing one or more steps of a method described herein.

In one embodiment, the chip set 3200 includes a communication mechanism such as a bus 3201 for passing information among the components of the chip set 3200. A processor 3203 has connectivity to the bus 3201 to execute instructions and process information stored in, for example, a memory 3205. The processor 3203 may include one or more processing cores with each core configured to perform independently. A multi-core processor enables multiprocessing within a single physical package. Examples of a multi-core processor include two, four, eight, or greater numbers of processing cores. Alternatively or in addition, the processor 3203 may include one or more microprocessors configured in tandem via the bus 3201 to enable independent execution of instructions, pipelining, and multithreading. The processor 3203 may also be accompanied with one or more specialized components to perform certain processing functions and tasks such as one or more digital signal processors (DSP) 3207, or one or more application-specific integrated circuits (ASIC) 3209. A DSP 3207 typically is configured to process real-world signals (e.g., sound) in real time independently of the processor 3203. Similarly, an ASIC 3209 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 3203 and accompanying components have connectivity to the memory 3205 via the bus 3201. The memory 3205 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 3205 also stores the data associated with or generated by the execution of one or more steps of the methods described herein.

FIG. 33 is a diagram of exemplary components of a mobile terminal 3300 (e.g., cell phone handset) for communications, which is capable of operating in the system, according to one embodiment. In some embodiments, mobile terminal 3301, or a portion thereof, constitutes a means for performing one or more steps described herein. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 3303, a Digital Signal Processor (DSP) 3305, and a receiver/transmitter unit including a microphone gain control unit and a speaker gain control unit. A main display unit 3307 provides a display to the user in support of various applications and mobile terminal functions that perform or support the steps as described herein. The display 3307 includes display circuitry configured to display at least a portion of a user interface of the mobile terminal (e.g., mobile telephone). Additionally, the display 3307 and display circuitry are configured to facilitate user control of at least some functions of the mobile terminal. An audio function circuitry 3309 includes a microphone 3311 and microphone amplifier that amplifies the speech signal output from the microphone 3311. The amplified speech signal output from the microphone 3311 is fed to a coder/decoder (CODEC) 3313.

A radio section 3315 amplifies power and converts frequency in order to communicate with a base station, which is included in a mobile communication system, via antenna 3317. The power amplifier (PA) 3319 and the transmitter/modulation circuitry are operationally responsive to the MCU 3303, with an output from the PA 3319 coupled to the duplexer 3321 or circulator or antenna switch, as known in the art. The PA 3319 also couples to a battery interface and power control unit 3320.

In use, a user of mobile terminal 3301 speaks into the microphone 3311 and his or her voice along with any detected background noise is converted into an analog voltage. The analog voltage is then converted into a digital signal through the Analog to Digital Converter (ADC) 3323. The control unit 3303 routes the digital signal into the DSP 3305 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 3325 for compensation of any frequency-dependent impairments that occur during transmission though the air such as phase and amplitude distortion. After equalizing the bit stream, the modulator 3327 combines the signal with a RF signal generated in the RF interface 3329. The modulator 3327 generates a sine wave by way of frequency or phase modulation. In order to prepare the signal for transmission, an up-converter 3331 combines the sine wave output from the modulator 3327 with another sine wave generated by a synthesizer 3333 to achieve the desired frequency of transmission. The signal is then sent through a PA 3319 to increase the signal to an appropriate power level. In practical systems, the PA 3319 acts as a variable gain amplifier whose gain is controlled by the DSP 3305 from information received from a network base station. The signal is then filtered within the duplexer 3321 and optionally sent to an antenna coupler 3335 to match impedances to provide maximum power transfer. Finally, the signal is transmitted via antenna 3317 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 3301 are received via antenna 3317 and immediately amplified by a low noise amplifier (LNA) 3337. A down-converter 3339 lowers the carrier frequency while the demodulator 3341 strips away the RF leaving only a digital bit stream. The signal then goes through the equalizer 3325 and is processed by the DSP 3305. A Digital to Analog Converter (DAC) 3343 converts the signal and the resulting output is transmitted to the user through the speaker 3345, all under control of a Main Control Unit (MCU) 3303 which can be implemented as a Central Processing Unit (CPU) (not shown).

The MCU 3303 receives various signals including input signals from the keyboard 3347. The keyboard 3347 and/or the MCU 3303 in combination with other user input components (e.g., the microphone 3311) comprise a user interface circuitry for managing user input. The MCU 3303 runs a user interface software to facilitate user control of at least some functions of the mobile terminal 3301 as described herein. The MCU 3303 also delivers a display command and a switch command to the display 3307 and to the speech output switching controller, respectively. Further, the MCU 3303 exchanges information with the DSP 3305 and can access an optionally incorporated SIM card 3349 and a memory 3351. In addition, the MCU 3303 executes various control functions required of the terminal. The DSP 3305 may, depending upon the implementation, perform any of a variety of conventional digital processing functions on the voice signals. Additionally, DSP 3305 determines the background noise level of the local environment from the signals detected by microphone 3311 and sets the gain of microphone 3311 to a level selected to compensate for the natural tendency of the user of the mobile terminal 3301.

The CODEC 3313 includes the ADC 3323 and DAC 3343. The memory 3351 stores various data including call incoming tone data and is capable of storing other data including music data received via, e.g., the global Internet. The software module could reside in RAM memory, flash memory, registers, or any other form of writable storage medium known in the art. The memory device 3351 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 3349 carries, for instance, important information, such as the cellular phone number, the carrier supplying service, subscription details, and security information. The SIM card 3349 serves primarily to identify the mobile terminal 3301 on a radio network. The card 3349 also contains a memory for storing a personal telephone number registry, text messages, and user specific mobile terminal settings.

In some embodiments, the mobile terminal 3301 includes a digital camera comprising an array of optical detectors, such as charge coupled device (CCD) array 3365. The output of the array is image data that is transferred to the MCU for further processing or storage in the memory 3351 or both. In the illustrated embodiment, the light impinges on the optical array through a lens 3363, such as a pin-hole lens or a material lens made of an optical grade glass or plastic material. In the illustrated embodiment, the mobile terminal 3301 includes a light source 3361, such as a LED to illuminate a subject for capture by the optical array, e.g., CCD 3365. The light source is powered by the battery interface and power control module 3320 and controlled by the MCU 3303 based on instructions stored or loaded into the MCU 3303.

5. Alternatives and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

What is claimed is:

1. A probe composition having the structural formula

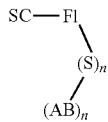

wherein Fl is a fluorophore portion configured to change an optical property of fluorescent light emitted in response to incident excitation light when the composition changes between a first state in which the analyte is not bound to the analyte-binding portion and a second state in which the analyte binds to the analyte-binding portion via a photophysical mechanism selected from the group consisting of quenching, photo-induced electron transfer (PET), and intramolecular charge transfer (ICT);

wherein AB is an analyte-binding portion comprising boronic aced or a diboronic acid that binds to an analyte in aqueous solution;

wherein S is a spacer group that provides sufficient spacing between AB and Fl such that when AB binds to an analyte, the fluorophore portion changes an optical property of fluorescent light emitted in response to incident excitation light when the probe composition changes between a first state in which the analyte is not bound to the analyte-binding portion and a second state in which the analyte binds to the analyte-binding portion;

wherein SC is a hydrophobic portion comprising a $C_8$-$C_{18}$ alkyl group and separating units of polyethylene glycol, hydroxyl groups, or arginine peptide; and wherein n is an integer from 1 to 20.

2. The probe composition of claim 1 wherein Fl includes an electron donor sub-portion and a separate electron acceptor sub-portion.

3. The probe composition of claim 2 wherein both said sub-portions participate in Forster resonance energy transfer (FRET).

4. The probe composition of claim 1 which is a modular composition wherein the donor sub-portion and the acceptor sub-portion are separate moieties connected by an aliphatic linker that includes a diboronic acid.

5. A probe composition of claim 1 wherein SC comprises a $C_{18}$ alkyl group.

6. The probe composition as recited in claim 1, wherein the analyte to be bound by the analyte binding portion is selected from a group comprising: glucose, cations of Group I and Group II metals, and anions of Group VIIA.

7. A composition comprising:
   (a) a silicone hydrogel substrate having interstices and a hydrogel network that allows flow of aqueous solution through the hydrogel network, wherein a silicone network occupies the interstices of the hydrogel network; and
   (b) the probe composition of claim 1, wherein SC is attracted to an interface between the hydrogel network and the silicone network.

8. The composition of claim 7 wherein the surface of the composition is treated to provide a stronger hydrophobic attraction than the untreated surface, whereby the concentration of the probe composition is greater on the treated surface of the composition than on the untreated surface or on the interior of the composition.

9. The composition of claim 7 which is incorporated into a contact lens.

10. The composition of claim 7 wherein the probe composition is a modular composition wherein the donor sub-portion and the acceptor sub-portion of Fl are separate pairs of species selected from the group consisting of:
   (a) quinolinium C-18 and 7-nitrobenz-2-oxa-1,3-diazol-4-yl (NBD) with a C18 side chain (NBD C-18);
   (b) naphthalene and dansyl;
   (c) dansyl and fluorescein-5-isothiocyanate (FITC);
   (d) dansyl and octadicylrhodamine (ODR);
   (e) 1-N6-ethenoadenosine (E-A) and NBD;
   (f) 5-iodoacetamidofluorescein (IAF) and tetramethylrhodamine (TMR);
   (g) pyrene and cumarin;
   (h) FITC and TMR;
   (i) 5-(2-((iodocetyl)amino)ethyl)aminonaphthalene-1-sulfonic acid (IAEDANS) and FITC;
   (j) IAEDANS and IAF;
   (k) IAF and enzyme immunoassay (EIA);
   (l) carboxylfluorescein succinimidyl ester (CF) and Texas Red (TR);
   (m) 4,4-difluoro-4-bora-3a, 4a-diaza-s-indacene (Bodipy) and Bodipy;
   (n) B-phycoerythin (BPE) and cyanine dye (Cy);
   (o) terbium and rhodamine;
   (p) europium and Cy; and
   (q) europium and allophycocyanin (APC).

11. The composition of claim 10 wherein the acceptor sub-portion further comprises one of a plurality of halogen groups.

12. The composition of claim 7 which has a longitudinal axis length between 2-8 nm when the analyte is not bound to the analyte-binding portion.

13. The composition of claim 4 wherein the probe composition has the structure

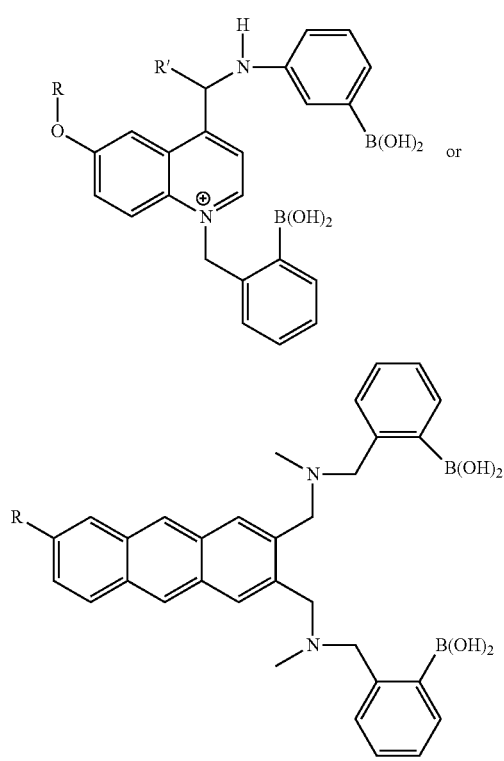

or wherein R is selected from the group consisting of:

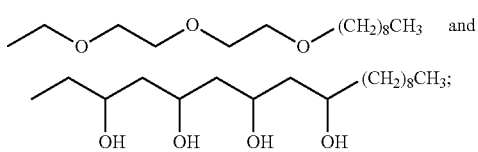

and wherein R', when present, is hydrogen or a ketone functional group.

14. The composition of claim 7 wherein the probe composition has a structure selected from the group consisting of

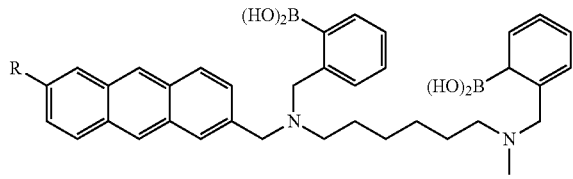

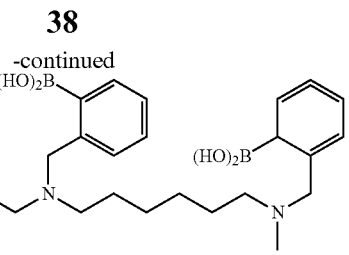

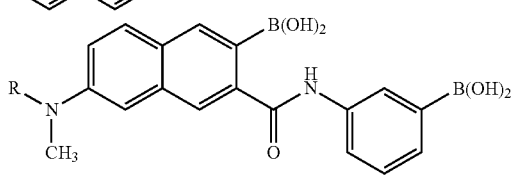

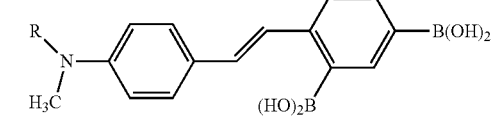

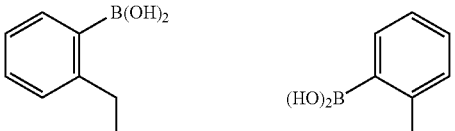

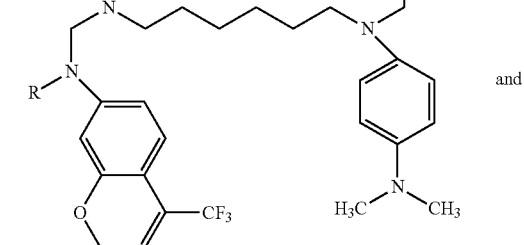

wherein R is

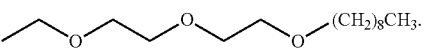

15. A system comprising:

(a) the composition of claim 7; and (b) a remote monitor subsystem configured to detect the change of the optical property of the fluorescent light emitted in response to the incident excitation light without mechanically contacting the material.

16. A system as recited in claim 15 wherein the material is fixed to a microfluidic device.

17. A system as recited in claim 15 wherein the material is incorporated into a contact lens.

18. A system as recited in claim 15, wherein the monitor subsystem further comprises:
an incident light source;
a light detector; and
a processing system, the processing system further comprising
at least one processor; and
at least one memory including one or more sequences of instructions,
the at least one memory and the one or more sequences of instructions configured to, with the at least one processor, cause the system to perform at least the following,
operate the incident light source to illuminate the material,
operate the light detector to obtain data that indicates the property of the emitted fluorescent light, and
determine a concentration of the analyte based on the data that indicates the property of the emitted fluorescent light.

19. The system as recited in claim 18 wherein the system further comprising an analyte response device; and the at least one memory and the one or more sequences of instructions are further configured to, with the at least one processor, cause the system to operate the analyte response device based on the concentration of the analyte.

20. A method comprising:
(a) obtaining a silicone hydrogel substrate;
(b) contacting the substrate with an aqueous solution that comprises the probe composition as recited in claim 1, wherein the composition is a probe, to form a probe-substrate material;
(c) contacting probe-substrate material with an aqueous sample solution;
(d) illuminating, using a light source, the probe-substrate material in contact with the sample solution;
(e) measuring a value of a property of the fluorescent light emitted by the material in contact with the sample solution in response to the illuminating; and
(f) determining a value of a concentration of the analyte in the aqueous sample solution based on the value of the property.

21. A method as recited in claim 20, wherein said step of determining the concentration of the analyte is performed automatically on a processor.

22. A method as recited in claim 20, further comprising operating an analyte response device based on the value of the concentration of the analyte in the aqueous sample solution.

23. A non-transitory computer-readable medium carrying one or more sequences of instructions, wherein execution of the one or more sequences of instructions by one or more processors causes the one or more processors to perform the steps of:
operating an incident light source to illuminate the material of claim 7,
operating a light detector to obtain data that indicates the property of fluorescent light emitted in response to operating the incident light source, and
determining a concentration of the analyte based on the data that indicates the property of the emitted fluorescent light.

24. A computer-readable medium as recited in claim 23, wherein execution of the one or more sequences of instructions by one or more processors further causes the one or more processors to perform the step of operating an analyte response device based on the concentration of the analyte.

* * * * *